(12) United States Patent
Pecor

(10) Patent No.: US 7,445,592 B2
(45) Date of Patent: Nov. 4, 2008

(54) CANNULAE HAVING REDUCED FLOW RESISTANCE

(75) Inventor: Robert Pecor, Aliso Viejo, CA (US)

(73) Assignee: Orqis Medical Corporation, Lake Forest, CA (US)

( * ) Notice: Subject to any disclaimer, the term of this patent is extended or adjusted under 35 U.S.C. 154(b) by 252 days.

(21) Appl. No.: 10/866,535

(22) Filed: Jun. 10, 2004

(65) Prior Publication Data

US 2005/0277803 A1 Dec. 15, 2005

(51) Int. Cl.
*A61N 1/362* (2006.01)

(52) U.S. Cl. ......................................... 600/16

(58) Field of Classification Search ................... 600/16, 600/485; 604/6.14, 507
See application file for complete search history.

(56) References Cited

U.S. PATENT DOCUMENTS

| | | | |
|---|---|---|---|
| 1,902,418 A | | 3/1933 | Pilgrim |
| 2,876,769 A | | 3/1959 | Cordova |
| 2,935,068 A | | 5/1960 | Donaldson |
| 3,017,885 A | | 1/1962 | Robicsek |
| 3,410,263 A | | 11/1968 | McGinnis |
| 3,592,184 A | | 7/1971 | Watkins et al. |
| 3,692,018 A | | 9/1972 | Goetz et al. |
| 3,835,864 A | | 9/1974 | Rasor et al. |
| 3,885,251 A | | 5/1975 | Pedrosa |
| 3,938,530 A | | 2/1976 | Santomieri |
| 3,939,820 A | | 2/1976 | Grayzel |
| 3,964,479 A | | 6/1976 | Boag et al. |
| 3,995,617 A | * | 12/1976 | Watkins et al. ................. 600/16 |
| 4,000,739 A | | 1/1977 | Stevens |
| 4,004,299 A | | 1/1977 | Runge |
| 4,016,864 A | | 4/1977 | Sielaff et al. |
| 4,034,742 A | | 7/1977 | Thoma |
| 4,047,849 A | | 9/1977 | Clay |
| 4,051,840 A | | 10/1977 | Kantrowitz et al. |
| 4,077,394 A | | 3/1978 | McCurdy |

(Continued)

FOREIGN PATENT DOCUMENTS

DE 91 11 200 U 11/1991

(Continued)

OTHER PUBLICATIONS

U.S. Appl. No. 11/417,917, filed May 3, 2006, Viole et al., including its associated file history.

(Continued)

*Primary Examiner*—George Manuel
(74) *Attorney, Agent, or Firm*—Knobbe, Martens, Olson & Bear, LLP

(57) ABSTRACT

A percutaneous cannula is provided for the exchange of blood within a patient's vasculature. The cannula includes a main cannula portion and a tip portion. The main cannula portion comprises a proximal portion, a distal portion, a first lumen, and a second lumen extending through the proximal portion. The tip portion extends from the main cannula portion to a distal end of the cannula. The tip portion comprises a discharge opening and a redirecting member. The redirecting member is configured to direct blood flow being discharged through the discharge opening proximally along the cannula. At least one of the first and second lumens is configured to reduce the effect of flow resistance therein.

31 Claims, 30 Drawing Sheets

U.S. PATENT DOCUMENTS

| | | |
|---|---|---|
| 4,080,958 A | 3/1978 | Bregman et al. |
| 4,134,402 A | 1/1979 | Mahurkar |
| 4,135,496 A | 1/1979 | Chazov et al. |
| 4,143,616 A | 3/1979 | Bible |
| 4,154,227 A | 5/1979 | Krause et al. |
| 4,167,046 A | 9/1979 | Portner et al. |
| 4,240,409 A | 12/1980 | Robinson et al. |
| 4,302,854 A | 12/1981 | Runge |
| 4,375,941 A | 3/1983 | Child |
| 4,384,829 A | 5/1983 | Colney et al. |
| 4,385,631 A | 5/1983 | Uthmann |
| 4,405,313 A | 9/1983 | Sisley et al. |
| 4,407,271 A | 10/1983 | Schiff |
| 4,411,655 A | 10/1983 | Schreck |
| 4,447,236 A | 5/1984 | Qiunn |
| 4,457,673 A | 7/1984 | Conley et al. |
| 4,459,977 A | 7/1984 | Pizon et al. |
| 4,464,164 A | 8/1984 | Troutner et al. |
| 4,522,195 A | 6/1985 | Schiff |
| 4,540,402 A | 9/1985 | Aigner |
| 4,543,087 A | 9/1985 | Sommercorn et al. |
| 4,546,759 A | 10/1985 | Solar |
| 4,552,552 A | 11/1985 | Polaschegg et al. |
| 4,569,332 A | 2/1986 | Schiff et al. |
| 4,573,997 A | 3/1986 | Wisman et al. |
| 4,611,578 A | 9/1986 | Heimes |
| 4,625,712 A | 12/1986 | Wampler |
| 4,666,443 A | 5/1987 | Portner |
| 4,685,446 A | 8/1987 | Choy |
| 4,688,998 A | 8/1987 | Olsen et al. |
| 4,690,134 A | 9/1987 | Snyders |
| 4,692,141 A | 9/1987 | Mahukar |
| 4,697,574 A | 10/1987 | Karcher et al. |
| 4,719,921 A | 1/1988 | Chirife |
| 4,756,302 A | 7/1988 | Portner et al. |
| 4,759,760 A | 7/1988 | Snapp, Jr. |
| 4,771,765 A | 9/1988 | Choy et al. |
| 4,798,591 A | 1/1989 | Okada |
| 4,822,357 A | 4/1989 | Forster et al. |
| 4,838,889 A | 6/1989 | Kolff |
| 4,857,062 A | 8/1989 | Russell |
| 4,861,330 A | 8/1989 | Voss |
| 4,872,874 A | 10/1989 | Taherin |
| 4,883,462 A | 11/1989 | Williamson et al. |
| 4,895,150 A | 1/1990 | Isaacson et al. |
| 4,902,272 A | 2/1990 | Milder et al. |
| 4,902,273 A | 2/1990 | Choy et al. |
| 4,906,229 A | 3/1990 | Wampler |
| 4,908,012 A | 3/1990 | Moise et al. |
| 4,925,452 A | 5/1990 | Mellinyshyn et al. |
| 4,927,407 A | 5/1990 | Dorman |
| 4,944,745 A | 7/1990 | Sogand et al. |
| 4,957,504 A | 9/1990 | Chardack |
| 4,960,411 A | 10/1990 | Buchbinder |
| 4,968,293 A | 11/1990 | Nelson |
| 4,976,270 A | 12/1990 | Parl et al. |
| 4,985,014 A | 1/1991 | Orejola |
| 4,994,078 A | 2/1991 | Jarvik |
| 4,995,856 A | 2/1991 | Heindl et al. |
| 4,995,857 A | 2/1991 | Arnold |
| 4,995,865 A | 2/1991 | Gahara et al. |
| 5,011,469 A | 4/1991 | Buckberg et al. |
| 5,014,715 A * | 5/1991 | Chapolini ................... 600/485 |
| 5,020,516 A | 6/1991 | Biondi et al. |
| 5,041,098 A | 8/1991 | Loiterman et al. |
| 5,059,167 A | 10/1991 | Lundquist et al. |
| 5,066,285 A | 11/1991 | Hillstead |
| 5,069,662 A | 12/1991 | Bodden |
| 5,087,247 A | 2/1992 | Horn et al. |
| 5,089,017 A | 2/1992 | Young et al. |
| 5,092,844 A | 3/1992 | Schwartz et al. |
| 5,098,370 A | 3/1992 | Rahat et al. |
| 5,114,408 A | 5/1992 | Fleischhaker et al. |
| 5,116,564 A | 5/1992 | Jansen et al. |
| 5,129,878 A | 7/1992 | Takano et al. |
| 5,129,883 A | 7/1992 | Black |
| 5,131,905 A | 7/1992 | Grooters |
| 5,133,744 A | 7/1992 | Ramos Martinez |
| 5,147,281 A | 9/1992 | Thornton et al. |
| 5,147,388 A | 9/1992 | Yamazaki |
| 5,169,378 A | 12/1992 | Figuera |
| 5,169,379 A | 12/1992 | Freed et al. |
| 5,171,207 A | 12/1992 | Whalen |
| 5,176,619 A | 1/1993 | Segalowitz |
| 5,186,713 A * | 2/1993 | Raible ....................... 604/6.14 |
| 5,211,546 A | 5/1993 | Issacson et al. |
| 5,211,659 A | 5/1993 | Strimling et al. |
| 5,250,036 A | 10/1993 | Farivar |
| 5,263,978 A | 11/1993 | Kaufman et al. |
| 5,267,940 A | 12/1993 | Moulder |
| 5,273,518 A | 12/1993 | Lee et al. |
| 5,279,551 A | 1/1994 | James |
| 5,290,227 A | 3/1994 | Pasque |
| 5,290,263 A | 3/1994 | Wigness et al. |
| 5,300,113 A | 4/1994 | Arpesella et al. |
| 5,318,518 A | 6/1994 | Plechinger et al. |
| 5,332,403 A | 7/1994 | Kolff |
| 5,336,205 A | 8/1994 | Zenzen et al. |
| 5,346,458 A | 9/1994 | Affeld |
| 5,352,180 A | 10/1994 | Candelon et al. |
| 5,374,239 A | 12/1994 | Mischenko |
| 5,376,113 A | 12/1994 | Jansen et al. |
| 5,378,230 A | 1/1995 | Mahurkar |
| 5,403,291 A | 4/1995 | Abrahamson |
| 5,405,329 A | 4/1995 | Durand |
| 5,413,549 A | 5/1995 | Leschinsky |
| 5,417,705 A | 5/1995 | Haber et al. |
| 5,429,584 A | 7/1995 | Chiu |
| 5,433,731 A | 7/1995 | Hoegnelid et al. |
| 5,437,601 A | 8/1995 | Runge |
| 5,453,076 A | 9/1995 | Kiyota et al. |
| 5,453,084 A | 9/1995 | Moses |
| 5,472,417 A | 12/1995 | Martin et al. |
| 5,486,159 A | 1/1996 | Mahurkar |
| 5,503,615 A | 4/1996 | Goldstein |
| 5,505,710 A | 4/1996 | Dorsey, III |
| 5,511,958 A | 4/1996 | Chen et al. |
| 5,514,073 A | 5/1996 | Miyata et al. |
| 5,522,800 A | 6/1996 | Crocker |
| 5,533,957 A | 7/1996 | Aldea |
| 5,533,958 A | 7/1996 | Wilk |
| 5,536,250 A | 7/1996 | Klien et al. |
| 5,542,937 A | 8/1996 | Chee et al. |
| 5,554,136 A | 9/1996 | Luther |
| 5,556,390 A | 9/1996 | Hicks |
| 5,562,595 A | 10/1996 | Neisz |
| 5,571,093 A | 11/1996 | Cruz et al. |
| 5,584,804 A | 12/1996 | Klatz et al. |
| 5,616,137 A | 4/1997 | Lindsay |
| 5,618,267 A | 4/1997 | Palestrant |
| 5,643,226 A | 7/1997 | Cosgrove et al. |
| 5,649,911 A | 7/1997 | Terotola |
| 5,672,158 A | 9/1997 | Okada et al. |
| 5,722,930 A | 3/1998 | Larson et al. |
| 5,746,575 A | 5/1998 | Westphal et al. |
| 5,746,709 A | 5/1998 | Rom et al. |
| 5,749,855 A | 5/1998 | Reitan |
| 5,776,111 A | 7/1998 | Tesio |
| 5,785,686 A | 7/1998 | Runge |
| 5,792,118 A | 8/1998 | Kurth et al. |
| 5,795,326 A | 8/1998 | Siman |
| 5,807,311 A | 9/1998 | Palestrant |
| 5,824,070 A | 10/1998 | Jarvik |
| 5,851,174 A | 12/1998 | Jarvik et al. |

| | | | |
|---|---|---|---|
| 5,868,703 A | 2/1999 | Bertolero et al. | |
| 5,911,685 A | 6/1999 | Siess et al. | |
| 5,928,181 A | 7/1999 | Coleman et al. | |
| 5,941,813 A | 8/1999 | Sievers et al. | |
| 5,947,953 A | 9/1999 | Ash et al. | |
| 5,961,486 A | 10/1999 | Twardowski et al. | |
| 5,964,694 A | 10/1999 | Siess et al. | |
| 5,965,089 A | 10/1999 | Jarvik et al. | |
| 6,044,845 A | 4/2000 | Lewis | |
| 6,053,900 A | 4/2000 | Brown et al. | |
| 6,059,760 A | 5/2000 | Sandmore et al. | |
| 6,083,198 A | 7/2000 | Afzal | |
| 6,085,754 A | 7/2000 | Alferness et al. | |
| 6,102,891 A | 8/2000 | Maria van Erp | |
| 6,135,981 A | 10/2000 | Dyke | |
| 6,167,765 B1 | 1/2001 | Weitzel | |
| 6,183,411 B1 | 2/2001 | Mortier et al. | |
| 6,190,408 B1 | 2/2001 | Melvin | |
| 6,200,260 B1 | 3/2001 | Bolling | |
| 6,221,103 B1 | 4/2001 | Melvin | |
| 6,224,540 B1 | 5/2001 | Lederman et al. | |
| 6,228,052 B1 | 5/2001 | Pohndorf | |
| 6,231,543 B1 | 5/2001 | Hedge et al. | |
| 6,245,045 B1 | 6/2001 | Stratienko | |
| 6,287,608 B1 | 9/2001 | Levin et al. | |
| 6,293,958 B1 | 9/2001 | Berry et al. | |
| 6,299,575 B1 | 10/2001 | Bolling | |
| 6,371,935 B1 | 4/2002 | Macoviak et al. | |
| 6,387,037 B1 | 5/2002 | Bolling et al. | |
| 6,387,087 B1 * | 5/2002 | Grooters | 604/507 |
| 6,390,969 B1 | 5/2002 | Bolling et al. | |
| 6,428,464 B1 | 8/2002 | Bolling | |
| 6,488,662 B2 | 12/2002 | Sirimanne | |
| 6,508,777 B1 | 1/2003 | Macoviak et al. | |
| 6,514,226 B1 | 2/2003 | Levin et al. | |
| 6,558,356 B2 | 5/2003 | Barbut | |
| 6,569,145 B1 | 5/2003 | Shmulewitz et al. | |
| 6,575,934 B2 | 6/2003 | Duchamp | |
| 6,592,567 B1 | 7/2003 | Levin et al. | |
| 6,592,612 B1 | 7/2003 | Samson et al. | |
| 6,610,004 B2 | 8/2003 | Viole et al. | |
| 6,685,621 B2 | 2/2004 | Bolling et al. | |
| 6,719,749 B1 | 4/2004 | Schweikert et al. | |
| 6,800,075 B2 | 10/2004 | Mische et al. | |
| 6,889,082 B2 | 5/2005 | Bolling et al. | |
| 7,048,680 B2 | 5/2006 | Viole et al. | |
| 7,125,376 B2 | 10/2006 | Viole et al. | |
| 7,241,286 B2 | 7/2007 | Atlas | |
| 2002/0111577 A1 | 8/2002 | Sirimanne et al. | |
| 2002/0169413 A1 | 11/2002 | Keren et al. | |
| 2002/0188166 A1 | 12/2002 | Viole et al. | |
| 2002/0188167 A1 | 12/2002 | Viole et al. | |
| 2003/0040736 A1 | 2/2003 | Stevens et al. | |
| 2003/0069468 A1 | 4/2003 | Bolling | |
| 2003/0083617 A1 | 5/2003 | St. Germain et al. | |
| 2003/0144628 A1 | 7/2003 | Sirimanne | |
| 2003/0187367 A1 | 10/2003 | Odland | |
| 2004/0019251 A1 | 1/2004 | Viole et al. | |
| 2004/0116768 A1 | 6/2004 | Bolling et al. | |
| 2004/0236172 A1 | 11/2004 | Bolling et al. | |
| 2004/0236173 A1 | 11/2004 | Viole et al. | |
| 2005/0085683 A1 | 4/2005 | Bolling et al. | |
| 2005/0113631 A1 | 5/2005 | Bolling et al. | |
| 2005/0256363 A1 | 11/2005 | Bolling et al. | |
| 2005/0277804 A1 | 12/2005 | Pecor | |
| 2005/0277870 A1 | 12/2005 | Pecor | |
| 2006/0264689 A1 | 11/2006 | Viole et al. | |
| 2006/0264693 A1 | 11/2006 | Viole et al. | |
| 2006/0264694 A1 | 11/2006 | Viole et al. | |
| 2006/0264695 A1 | 11/2006 | Viole et al. | |
| 2006/0264797 A1 | 11/2006 | Viole et al. | |
| 2006/0264798 A1 | 11/2006 | Viole et al. | |
| 2006/0264800 A1 | 11/2006 | Bolling et al. | |
| 2006/0264801 A1 | 11/2006 | Bolling et al. |
| 2006/0270890 A1 | 11/2006 | Viole et al. |
| 2006/0270891 A1 | 11/2006 | Viole et al. |
| 2006/0270892 A1 | 11/2006 | Bolling et al. |
| 2006/0270893 A1 | 11/2006 | Bolling et al. |
| 2006/0270894 A1 | 11/2006 | Viole et al. |
| 2006/0270895 A1 | 11/2006 | Viole et al. |
| 2006/0270963 A1 | 11/2006 | Bolling et al. |
| 2006/0270964 A1 | 11/2006 | Viole et al. |
| 2006/0270965 A1 | 11/2006 | Viole et al. |
| 2006/0270966 A1 | 11/2006 | Bolling et al. |
| 2006/0276681 A1 | 12/2006 | Bolling |
| 2006/0276682 A1 | 12/2006 | Bolling et al. |
| 2006/0281962 A1 | 12/2006 | Bolling et al. |

FOREIGN PATENT DOCUMENTS

| | | |
|---|---|---|
| EP | 0232074 | 1/1987 |
| EP | 0 411 605 A1 | 1/1990 |
| EP | 0 405 749 A1 | 5/1990 |
| EP | 0 533 432 A1 | 3/1993 |
| EP | 0 711 574 A1 | 5/1996 |
| EP | 0 836 861 A1 | 4/1998 |
| EP | 1 407 798 A2 | 4/2004 |
| FR | 2 201 908 | 5/1974 |
| GB | 1 370 546 | 10/1974 |
| GB | 2 174 151 A | 1/1985 |
| JP | 08257001 | 10/1996 |
| RU | 1303165 A2 | 1/1985 |
| WO | WO 86/01416 | 3/1986 |
| WO | WO 94/05347 | 3/1994 |
| WO | WO 96/18358 | 6/1996 |
| WO | WO 98/14225 | 3/1997 |
| WO | WO 97/15228 | 5/1997 |
| WO | WO 98/28034 | 7/1998 |
| WO | WO 98/34676 | 8/1998 |
| WO | WO 99/16498 | 4/1999 |
| WO | WO 99/19010 | 4/1999 |
| WO | WO 99/21605 | 5/1999 |
| WO | WO 99/42155 | 8/1999 |
| WO | WO 99/59652 | 11/1999 |
| WO | WO 99/65546 | 12/1999 |
| WO | WO 00/12148 | 3/2000 |
| WO | WO 00/38591 | 7/2000 |
| WO | WO 00/61207 | 10/2000 |
| WO | WO 00/76577 | 12/2000 |
| WO | WO 02/064204 | 8/2002 |
| WO | WO 03/068303 | 8/2003 |

OTHER PUBLICATIONS

U.S. Appl. No. 10/743,841, Viole et al., including its associated file history.
PCT International Search Report dated Jun. 7, 205; PCT/US2004/037636, 13 pp., Our Reference.
PCT International Search Report dated Jun. 27, 2000, App. No. PCT/US 00/06749, 4 pp., Our Reference.
PCT International Preliminary Examination Report dated Sep. 29, 2003, App. No. PCT/US 01/42774, Our Reference.
PCT International Search Report dated Nov. 10, 2003; App. No. PCT/US 03/04401, 9 pp., Our Reference.
European Patent Office Office Action dated Apr. 11, 2005; European Application No. 01 983 207.0-2310, Our Reference.
PCT International Search Report, App. No. PCT/US 01/42774, App. Date: Oct. 15, 2001, 6 Pages.
PCT International Search Report, App. Date: Jun. 18, 2003 PCT/US/03/04401.
JAMA, Jan. 8, 1968. vol. 203. No. 2, Initial Clinical Experience with Intra-aortic Balloon Pumping in Cardiogenic Shock. pp. 113-118.
Article: A Mechanical Auxillar Ventricle. pp. M340-M344.
Article: Effect of Stationary Guiding Vanes on Improvement of the Washout Behind the Rotor in Centrifugal Blood Pumps: pp. M220-M224.

Article: An Implantable Seal-less Centrifugal Pump: Comparison of Ultrasonic Transit Time and Ultrasonic Doppler Systems: pp. 808-815.

Article: O.H. Frazier, MD. Long-Term Ventricular Support with the Heartmate in Patients Undergoing Bridge-to Transplant Operation: 3PP total.

Article: Concepts in the Application of Pneumatic Ventricular Assist Devices for Ischemic Myocardial Injury. pp. 162-168.

Article: Long-Term Left Ventricular Assist Device Use Before Transplantation: pp. M530-M534.

Article: In Vitro Characterization of a Magnetically Suspended Continuous Flow Ventricular Assist Device: pp. M359-M360.

Article: Estimation of Left Venticular Function in Patients With a Left Ventricular Assist device: M544-M551.

Article: Mechanical Auxillary Ventricle. pp. M345-M344.

Article: Long Term Follow Up of Survivors of Postcardiotomy Circulatory Support. Ruzevich et al.; 4535, A.S.A.I.O. Transactions 34 Apr.-Jun. 1998, No. 2, Hagerstown, MD, USA. pp. 16-124.

Article: Mechanical Cardiopulmonary Support During Arteriography and Surgical Correction of Coronary Insufficiency Producing Myocardial Infarction with Cardiogenic Shock; Carlson et al. Journal of the Association for the Advancement of Medical Instrumentation. vol. 6, No. 3. May-Jun. 1972; pp. 244-248.

Article: The Stemotomy Hemopump, A Second Generation Intraarterial Assist Device. pp. M218-M220, 223.

Article: Transarterial Closed-Chest Left Ventricular (TaCLV) Bypass. pp. 386-390.

Article: First Clinical Application of transarterial Closed-Chest Left Ventricular (TaCLV) Bypass. pp. 386-391.

Article: Implantable Left Ventricular Assist Device. pp. 1522-1533.

Article: Effects of Partial and Complete Unloading of The Falling Left Ventricle by Transarterial Left Heart Bypass. pp. 865-872.

Article: Hydrodynamic Properties of a New Percutaneous Intra-aortic Axial Flow Pump. Reltan et al. ASAIO Journal 2000, pp. 323-328.

Article: Hemodynamic Effects of the Concomitant Use of Intra-Aortic Balloon Pumping and Venoarterial Bypass without Oxygenation In Cardigenic Shock. Takamoto et al. Intra-Aortic Pumping & Ventroaterial Bypass. vol. 19. No. 6. Nov. 1978, pp. 938-945.

Journal of the Association for the Advancement of Medical Instrumentation, vol. 10, No. 5, Sep.-Oct. 1976, p. 215; Medical Instrumentation Editorial.

Dormandy, Goetz, and Kripke; Surgery, Feb. 1969, vol. 65, No. 2, pp. 311-320; Hemodynamics and coronary blood flow with counterpulsation.

The New England Journal of Medicine, Article: Treatement of Severe Fluid Overload by Ultrafiltration, vol. 291, No. 15, Oct. 10, 1974, pp. 747-751.

\* cited by examiner

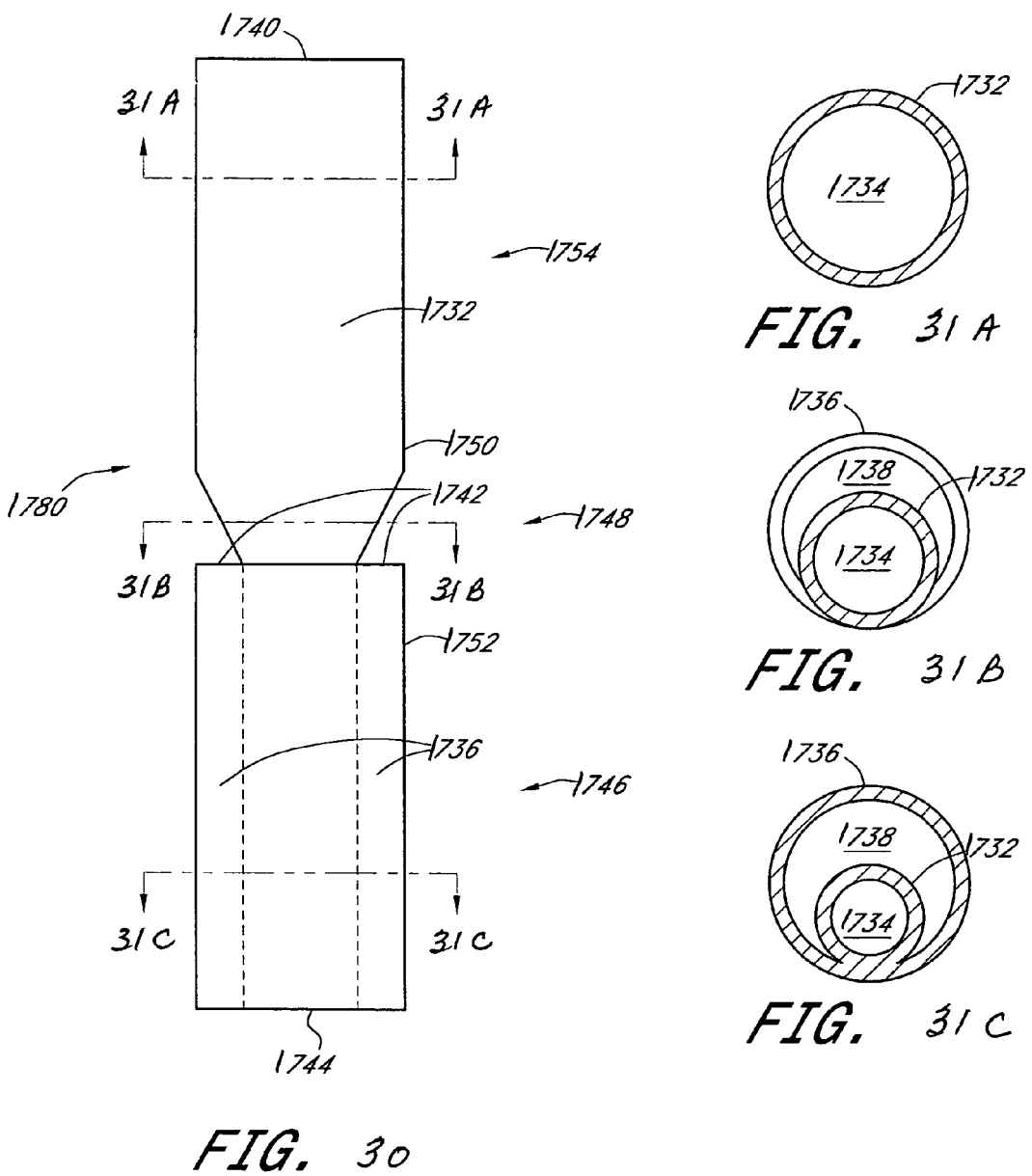

CANNULAE HAVING REDUCED FLOW RESISTANCE

BACKGROUND OF THE INVENTION

1. Field of the Invention

This application relates to cannulae and, in particular, to cannulae having reduced flow resistance and a tip configured to redirect the flow of fluid out of the cannula.

2. Description of the Related Art

Treatment and diagnosis of a variety of health conditions in a patient can involve withdrawing blood from and returning blood to a patient's vascular system, e.g., in treatment of organ failure. In dialysis treatments, which are sometimes applied to patients suffering from kidney failure, blood is withdrawn from the vascular system, filtered, and infused back into the vascular for further circulation. An emerging treatment for congestive heart failure involves coordinated withdrawal of blood from and infusion of blood into the vascular system. Both such treatments sometimes call for the insertion of cannulae into the vasculature of the patient.

It is sometimes beneficial to access the vascular system by way of a single entry point using a multilumen cannula. Multilumen cannulae enable blood to be withdrawn from the vascular system via a first lumen and infused back into the vascular system via a second lumen. By providing vascular access through a single point, multilumen cannulae are less invasive than other options for coordinated aspiration and infusion, such as the insertion of multiple single lumen cannulae through separate entry sites.

Though multilumen cannulae advantageously can limit the number of entry sites, the size of the lumens of such cannulae are limited by the need to fit more than one lumen into the same region of a vessel. Small lumens can suffer from high flow resistance, especially if relatively long. Increased flow resistance of the lumens of multilumen cannulae present many problems for the devices that are coupled with the cannulae to direct blood into or withdraw blood from the vascular system.

SUMMARY OF THE INVENTION

Therefore, there is a need for cannulae that reduce the resistance to blood flow in relatively long lumens. Also, there is a need for a percutaneous cannula assembly to enable insertion of such a cannula into the vasculature.

In one embodiment, a percutaneous cannula is provided for the exchange of blood within a patient's vasculature. The cannula includes a main cannula portion and a tip portion. The main cannula portion has a proximal portion, a distal portion, a first lumen, and a second lumen extending through the proximal portion. The first lumen has a first cross-sectional area at a location within the proximal portion and a second cross-sectional area at a location within the distal portion. The second cross-sectional area is greater than the first cross-sectional area. The tip portion extends from the main cannula portion to a distal end of the cannula. The tip portion has a discharge opening and a redirecting member. The redirecting member is configured to direct blood flow being discharged through the discharge opening proximally along the cannula.

In another embodiment, a percutaneous cannula is provided for the exchange of blood within a patient's vasculature. The cannula includes a main cannula portion and a tip portion. The main cannula portion comprises a proximal portion, a distal portion, a first lumen, and a second lumen extending through the proximal portion. The tip portion extends from the main cannula portion to a distal end of the cannula. The tip portion comprises a discharge opening and a redirecting member. The redirecting member is configured to direct blood flow being discharged through the discharge opening proximally along the cannula. At least one of the first and second lumens is configured to reduce the effect of flow resistance therein.

In another embodiment, a method for treating a patient is provided. The method includes: providing one or more of the percutaneous cannulae described herein; and using the cannulae to treat the patient.

BRIEF DESCRIPTION OF THE DRAWINGS

These and other features and advantages of the invention will now be described with reference to the drawings, which are intended to illustrate and not to limit the invention.

FIG. 25A is an enlarged view of a first configuration of a portion of a tip portion of the cannula of FIG. 25;

FIG. 25B is an enlarged view of a second configuration of a portion of a tip portion of the cannula of FIG. 25;

FIG. 30 is a schematic view of a variation of the embodiment of a multilumen cannula of FIG. 29;

FIG. 31A is a cross-section view of the multilumen cannula of FIG. 30 taken along section plane 31A-31A;

FIG. 31B is a cross-section view of the multilumen cannula of FIG. 30 taken along section plane 31B-31B;

FIG. 31C is a cross-section view of the multilumen cannula of FIG. 30 taken along section plane 31C-31C;

DETAILED DESCRIPTION OF THE PREFERRED EMBODIMENT

Turning now to the drawings provided herein, more detailed descriptions of various embodiments of heart assist systems and cannulae for use therewith are provided below.

I. Extracardiac Heart Assist Systems and Methods

A variety of cannulae are described herein that can be used in connection with a variety of heart assist systems that supplement blood perfusion. Such systems preferably are extracardiac in nature. In other words, the systems supplement blood perfusion, without the need to interface directly with the heart and aorta. Thus, the systems can be applied without major invasive surgery. The systems also lessen the hemodynamic burden or workload on the heart by reducing afterload, impedence, and/or left ventricular end diastolic pressure and volume (preload). The systems also advantageously increase peripheral organ perfusion and provide improvement in neurohormonal status. As discussed more fully below, the systems can be applied using one or more cannulae, one or more vascular grafts, and a combination of one or more cannulae and one or more vascular grafts. For systems employing cannula(e), the cannula(e) can be applied through multiple percutaneous insertion sites (sometimes referred to herein as a multi-site application) or through a single percutaneous insertion site (sometimes referred to herein as a single-site application).

A. Heart Assist Systems and Methods Employing Multi-site Application

Figure 1:
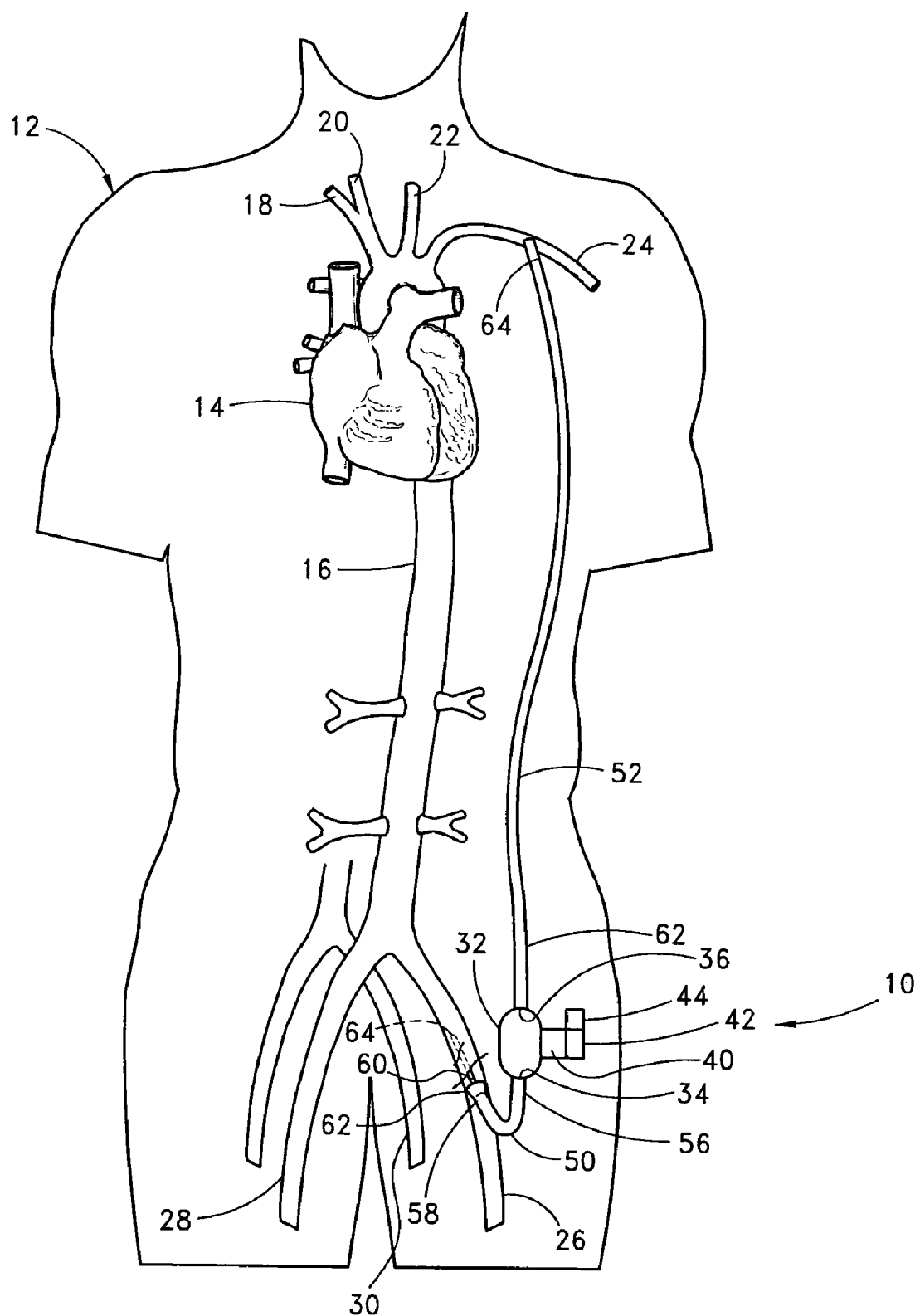
FIG. 1 is a schematic view of one embodiment of a heart assist system having multiple conduits for multi-site application, shown applied to a patient's vascular system.

With reference to FIG. 1, a first embodiment of a heart assist system 10 is shown applied to a patient 12 having an ailing heart 14 and an aorta 16, from which peripheral brachiocephalic blood vessels extend, including the right subclavian artery 18, the right carotid artery 20, the left carotid artery 22, and the left subclavian artery 24. Extending from the descending aorta is another set of peripheral blood vessels, the left and right iliac arteries which transition into the left and right femoral arteries 26, 28, respectively. As is known, each of the arteries 16, 18, 20, 22, 24, 26, and 28 generally conveys blood away from the heart. The vasculature includes a venous system that generally conveys blood to the heart. As will be discussed in more detail below, the heart assist systems described herein can also be applied to non-primary veins, including the left femoral vein 30.

The heart assist system 10 comprises a pump 32, having an inlet 34 and an outlet 36 for connection of conduits thereto. The pump 32 preferably is a rotary pump, either an axial type or a centrifugal type, although other types of pumps may be used, whether commercially-available or customized. The pump 32 preferably is sufficiently small to be implanted subcutaneously and preferably extrathoracically, for example in the groin area of the patient 12, without the need for major invasive surgery. Because the heart assist system 10 is an extracardiac system, no valves are necessary. Any inadvertent backflow through the pump 32 and/or through the inflow conduit would not harm the patient 12.

Regardless of the style or nature chosen, the pump 32 is sized to generate blood flow at subcardiac volumetric rates, less than about 50% of the flow rate of an average healthy heart, although flow rates above that may be effective. Thus, the pump 32 is sized and configured to discharge blood at volumetric flow rates anywhere in the range of 0.1 to 3 liters per minute, depending upon the application desired and/or the degree of need for heart assist. For example, for a patient experiencing advanced congestive heart failure, it may be preferable to employ a pump that has an average subcardiac rate of 2.5 to 3 liters per minute. In other patients, particularly those with minimal levels of heart failure, it may be preferable to employ a pump that has an average subcardiac rate of 0.5 liters per minute or less. In yet other patients it may be preferable to employ a pump that is a pressure wave generator that uses pressure to augment the flow of blood generated by the heart.

In one embodiment, the pump 32 is a continuous flow pump, which superimposes continuous blood-flow on the pulsatile aortic blood-flow. In another embodiment, the pump 32 has the capability of synchronous actuation; i.e., it may be actuated in a pulsatile mode, either in copulsating or counter-pulsating fashion.

For copulsating action, it is contemplated that the pump 32 would be actuated to discharge blood generally during systole, beginning actuation, for example, during isovolumic contraction before the aortic valve opens or as the aortic valve opens. The pump 32 would be static while the aortic valve is closed following systole, ceasing actuation, for example, when the aortic valve closes.

For counterpulsating actuation, it is contemplated that the pump 32 would be actuated generally during diastole, ceasing actuation, for example, before or during isovolumic contraction. Such an application would permit and/or enhance coronary blood perfusion. In this application, it is contemplated that the pump 32 would be static during the balance of systole after the aortic valve is opened, to lessen the burden against which the heart must pump. The aortic valve being open encompasses the periods of opening and closing, wherein blood is flowing therethrough.

It should be recognized that the designations copulsating and counterpulsating are general identifiers and are not limited to specific points in the patient's heart cycle when the pump 32 begins and discontinues actuation. Rather, they are intended to generally refer to pump actuation in which the pump 32 is actuating, at least in part, during systole and diastole, respectively. For example, it is contemplated that the pump 32 might be activated to be out of phase from true copulsating or counterpulsating actuation described herein, and still be synchronous, depending upon the specific needs of the patient or the desired outcome. One might shift actuation of the pump 32 to begin prior to or after isovolumic contraction or to begin before or after isovolumic relaxation.

Furthermore, the pulsatile pump may be actuated to pulsate asynchronously with the patient's heart. Typically, where the patient's heart is beating irregularly, there may be a desire to pulsate the pump 32 asynchronously so that the perfusion of blood by the heart assist system 10 is more regular and, thus, more effective at oxygenating the organs. Where the patient's heart beats regularly, but weakly, synchronous pulsation of the pump 32 may be preferred.

The pump 32 is driven by a motor 40 and/or other type of drive means and is controlled preferably by a programmable controller 42 that is capable of actuating the pump 32 in pulsatile fashion, where desired, and also of controlling the speed or output of the pump 32. For synchronous control, the patient's heart would preferably be monitored with an EKG in which feedback would be provided the controller 42. The controller 42 is preferably programmed by the use of external means. This may be accomplished, for example, using RF telemetry circuits of the type commonly used within implantable pacemakers and defibrillators. The controller may also be autoregulating to permit automatic regulation of the speed, and/or regulation of the synchronous or asynchronous pulsation of the pump 32, based upon feedback from ambient sensors monitoring parameters, such as pressure or the patient's EKG. It is also contemplated that a reverse-direction pump be utilized, if desired, in which the controller is capable of reversing the direction of either the drive means or the impellers of the pump. Such a pump might be used where it is desirable to have the option of reversing the direction of circulation between two blood vessels.

Power to the motor 40 and the controller 42 may be provided by a power source 44, such as a battery, that is preferably rechargeable by an external induction source (not shown), such as an RF induction coil that may be electromagnetically coupled to the battery to induce a charge therein. Alternative power sources are also possible, including a device that draws energy directly from the patient's body; e.g., the patient's muscles, chemicals or heat. The pump can be temporarily stopped during recharging with no appreciable life threatening effect, because the system only supplements the heart, rather than substituting for the heart.

Figure 16:
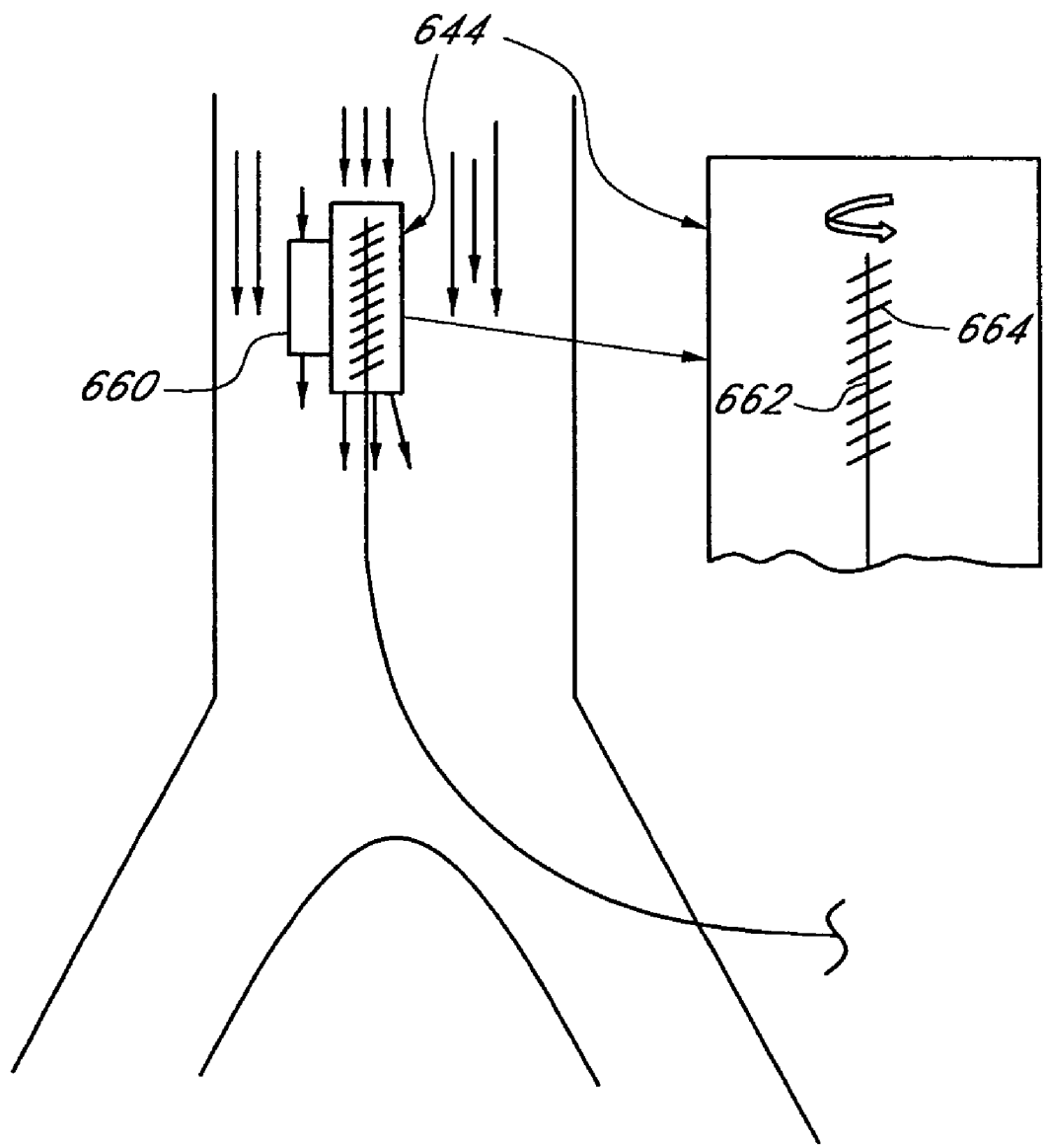
FIG. 16 is a schematic view of a modified embodiment of the heart assist system of FIG. 15 in which an additional conduit is shown adjacent the conduit housing the pump, and in which the pump comprises a shaft-mounted helical thread.

While the controller 42 and power source 44 are preferably pre-assembled to the pump 32 and implanted therewith, it is also contemplated that the pump 32 and motor 40 be implanted at one location and the controller 42 and the power source 44 be implanted in a separate location. In one alternative arrangement, the pump 32 may be driven externally through a percutaneous drive line or cable, as shown in FIG. 16. In another variation, the pump, motor and controller may be implanted and powered by an extracorporeal power source. In the latter case, the power source could be attached to the side of the patient to permit fully ambulatory movement.

The inlet 34 of the pump 32 is preferably connected to an inflow conduit 50 and an outflow conduit 52 to direct blood flow from one peripheral blood vessel to another. The conduits 50, 52 preferably are flexible conduits, as discussed more fully below. The conduits 50, 52 are coupled with the peripheral vessels in different ways in various embodiments of the heart assist system 10. As discussed more fully below, at least one of the conduits 50, 52 can be connected to a peripheral vessel, e.g., as a graft, using an anastomosis connection, and at least one of the conduits 50, 52 can be coupled with the same or another vessel via insertion of a cannula into the vasculature. Also, more than two conduits are used in some embodiments, as discussed below.

The inflow and outflow conduits 50, 52 may be formed from Dacron, Hemashield, Gortex, PVC, polyurethane, PTFE, ePTFE, nylon, or PEBAX materials, although other synthetic materials may be suitable. The inflow and outflow conduits 50, 52 may also comprise biologic materials or pseudobiological (hybrid) materials (e.g., biologic tissue supported on a synthetic scaffold). The inflow and outflow conduits 50, 52 are preferably configured to minimize kinks so blood flow is not meaningfully interrupted by normal movements of the patient or compressed easily from external forces. In some cases, the inflow and/or outflow conduits 50, 52 may come commercially already attached to the pump 32. Where it is desired to implant the pump 32 and the conduits 50, 52, it is preferable that the inner diameter of the conduits 50, 52 be less than 25 mm, although diameters slightly larger may be effective.

In one preferred application, the heart assist system 10 is applied in an arterial-arterial fashion; for example, as a femoral-axillary connection, as is shown in FIG. 1. It should be appreciated by one of ordinary skill in the art that an axillary-femoral connection would also be effective using the embodiments described herein. Indeed, it should be recognized by one of ordinary skill in the art that the present invention might be applied to any of the peripheral blood vessels in the patient. Another application of the heart assist system 10 couples the conduits 50, 52 with the same non-primary vessel in a manner similar to the application shown in FIG. 8 and discussed below.

Figure 6:
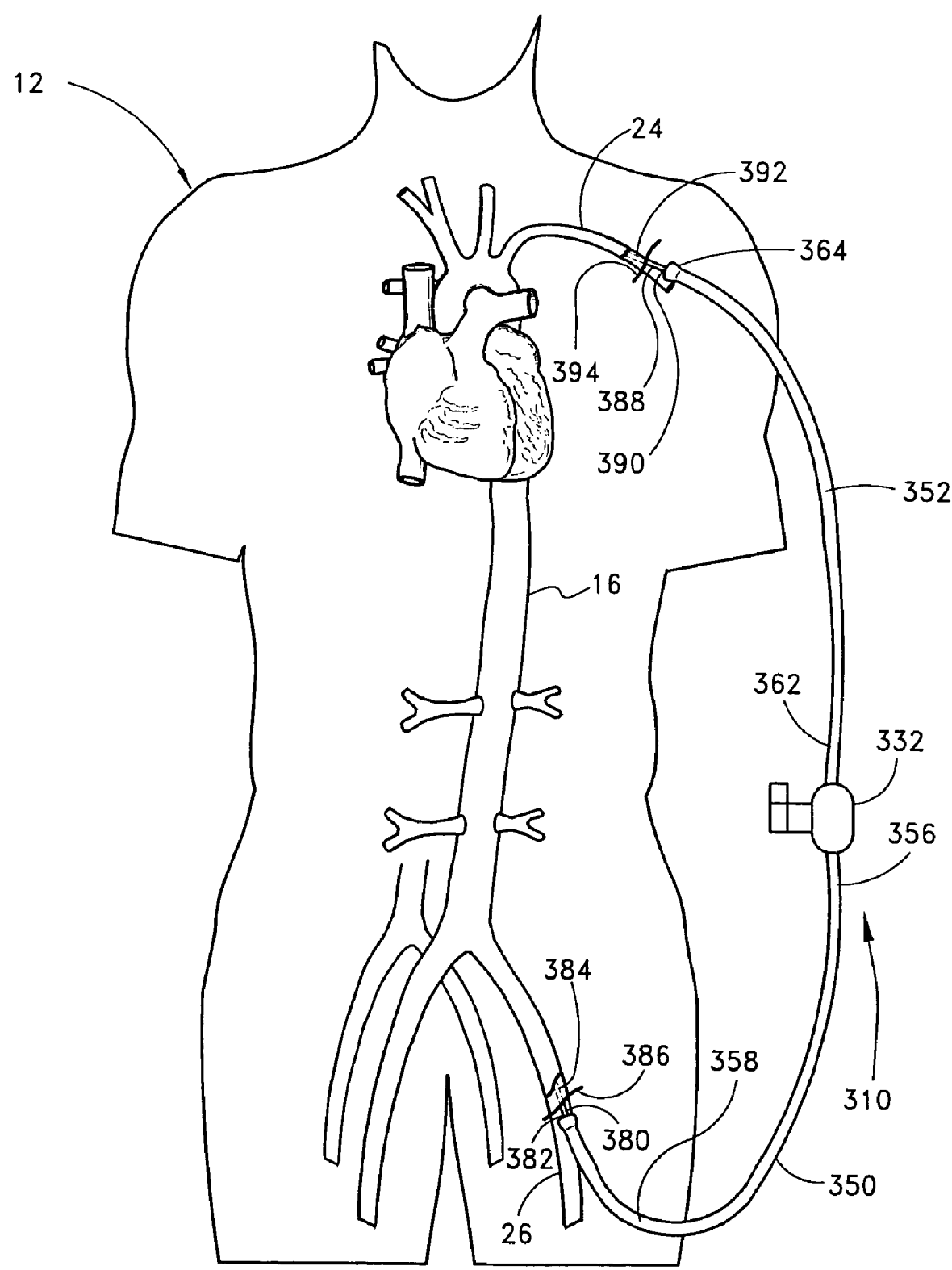
FIG. 6 is a schematic view of another embodiment of a heart assist system having multiple conduits for multi-site application, shown applied to a patient's vascular system.

FIG. 1 shows that the inflow conduit 50 has a first end 56 that connects with the inlet 34 of the pump 32 and a second end 58 that is coupled with a first non-primary blood vessel (e.g., the left femoral artery 26) by way of an inflow cannula 60. The inflow cannula 60 has a first end 62 and a second end 64. The first end 62 is sealably connected to the second end 58 of the inflow conduit 50. The second end 64 is inserted into the blood vessel (e.g., the left femoral artery 26). Although shown as discrete structures in FIG. 1, one skilled in the art would recognize that the inflow conduit 50 and the cannula 60 may be unitary in construction. While the cannula 60 preferably takes any suitable form, several particularly useful configurations of the cannula 60 are illustrated in FIGS. 17A-32B, discussed below.

Where the conduit 50 is at least partially extracorporeal, the inflow cannula 60 also may be inserted through a surgical opening (e.g., as shown in FIG. 6 and described in connection therewith) or percutaneously, with or without an introducer sheath (not shown). In other applications, the inflow cannula 60 could be inserted into the right femoral artery or any other peripheral artery.

FIG. 1 shows that the outflow conduit 52 has a first end 66 that connects to the outlet 36 of the pump 32 and a second end 68 that connects with a second peripheral blood vessel, preferably the left subclavian artery 24 of the patient 12, although the right axillary artery, or any other peripheral artery, would be acceptable. In one application, the connection between the outflow conduit 52 and the second blood vessel is via an end-to-side anastomosis, although a side-to-side anastomosis connection might be used mid-stream of the conduit where the outflow conduit were connected at its second end to yet another blood vessel or at another location on the same blood vessel (neither shown). Preferably, the outflow conduit 52 is attached to the second blood vessel at an angle that results in the predominant flow of blood out of the pump 32 proximally toward the aorta 16 and the heart 14, such as is shown in FIG. 1, while still maintaining sufficient flow distally toward the hand to prevent limb ischemia.

In another embodiment, the inflow conduit 50 is connected to the first blood vessel via an end-to-side anastomosis, rather than via the inflow cannula 60. The inflow conduit 50 could also be coupled with the first blood vessel via a side-to-side anastomosis connection mid-stream of the conduit where the inflow conduit were connected at its second end to an additional blood vessel or at another location on the same blood vessel (neither shown). Further details of these arrangements and other related applications are described in U.S. application Ser. No. 10/289,467, filed Nov. 6, 2002, the entire contents of which is hereby incorporated by reference in its entirety and made a part of this specification.

In another embodiment, the outflow conduit 52 also is coupled with the second blood vessel via a cannula, as shown in FIG. 6. This connection may be achieved in a manner similar to that shown in FIG. 1 in connection with the first blood vessel.

It is preferred that application of the heart assist system 10 to the peripheral or non-primary blood vessels be accomplished subcutaneously; e.g., at a shallow depth just below the skin or first muscle layer so as to avoid major invasive surgery. It is also preferred that the heart assist system 10 be applied extrathoracically to avoid the need to invade the patient's chest cavity. Where desired, the entire heart assist system 10 may be implanted within the patient 12, either extravascularly, e.g., as in FIG. 1, or at least partially intravascularly, e.g., as in FIGS. 14-16.

In the case of an extravascular application, the pump 32 may be implanted, for example, into the groin area, with the inflow conduit 50 fluidly connected subcutaneously to, for example, the femoral artery 26 proximate the pump 32. The outflow conduit would be tunneled subcutaneously through to, for example, the left subclavian artery 24. In an alternative arrangement, the pump 32 and associated drive and controller could be temporarily fastened to the exterior skin of the patient, with the inflow and outflow conduits 50, 52 connected percutaneously. In either case, the patient may be ambulatory without restriction of tethered lines.

Figure 2:
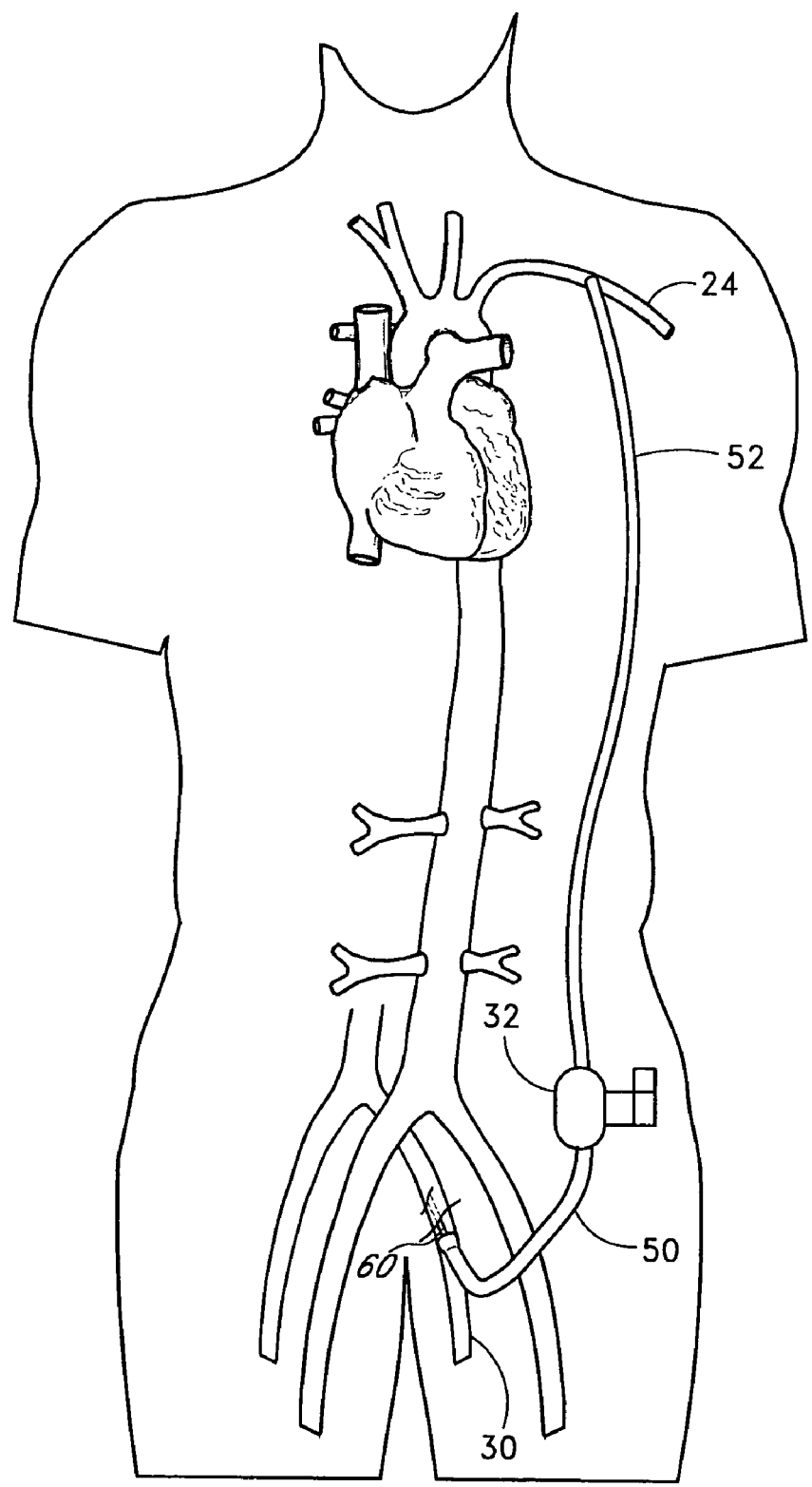
FIG. 2 is a schematic view of another application of the embodiment of FIG. 1.

While the heart assist system 10 and other heart assist systems described herein may be applied to create an arterial-arterial flow path, given the nature of the heart assist systems, i.e., supplementation of circulation to meet organ demand, a venous-arterial flow path may also be used. For example, with reference to FIG. 2, one application of the heart assist system 10 couples the inflow conduit 50 with a non-primary vein of the patient 12, such as the left femoral vein 30. In this arrangement, the outflow conduit 50 may be fluidly coupled with one of the peripheral arteries, such as the left subclavian artery 24. Arterial-venous arrangements are contemplated as well. In those venous-arterial cases where the inflow is connected to a vein and the outflow is connected to an artery, the pump 32 should be sized to permit flow sufficiently small so that oxygen-deficient blood does not rise to unacceptable levels in the arteries. It should be appreciated that the connections to the non-primary veins could be by one or more approach described above for connecting to a non-primary artery. It should also be appreciated that the present invention could be applied as a venous-venous flow path, wherein the inflow and outflow are connected to separate peripheral veins. In addition, an alternative embodiment comprises two discrete pumps and conduit arrangements, one being applied as a venous-venous flow path, and the other as an arterial-arterial flow path.

When venous blood is mixed with arterial blood either at the inlet of the pump or the outlet of the pump the ratio of venous blood to arterial blood should be controlled to maintain an arterial saturation of a minimum of 80% at the pump inlet or outlet. Arterial saturation can be measured and/or monitored by pulse oximetry, laser doppler, colorimetry or other methods used to monitor blood oxygen saturation. The venous blood flow into the system can then be controlled by regulating the amount of blood allowed to pass through the conduit from the venous-side connection.

Figure 3:
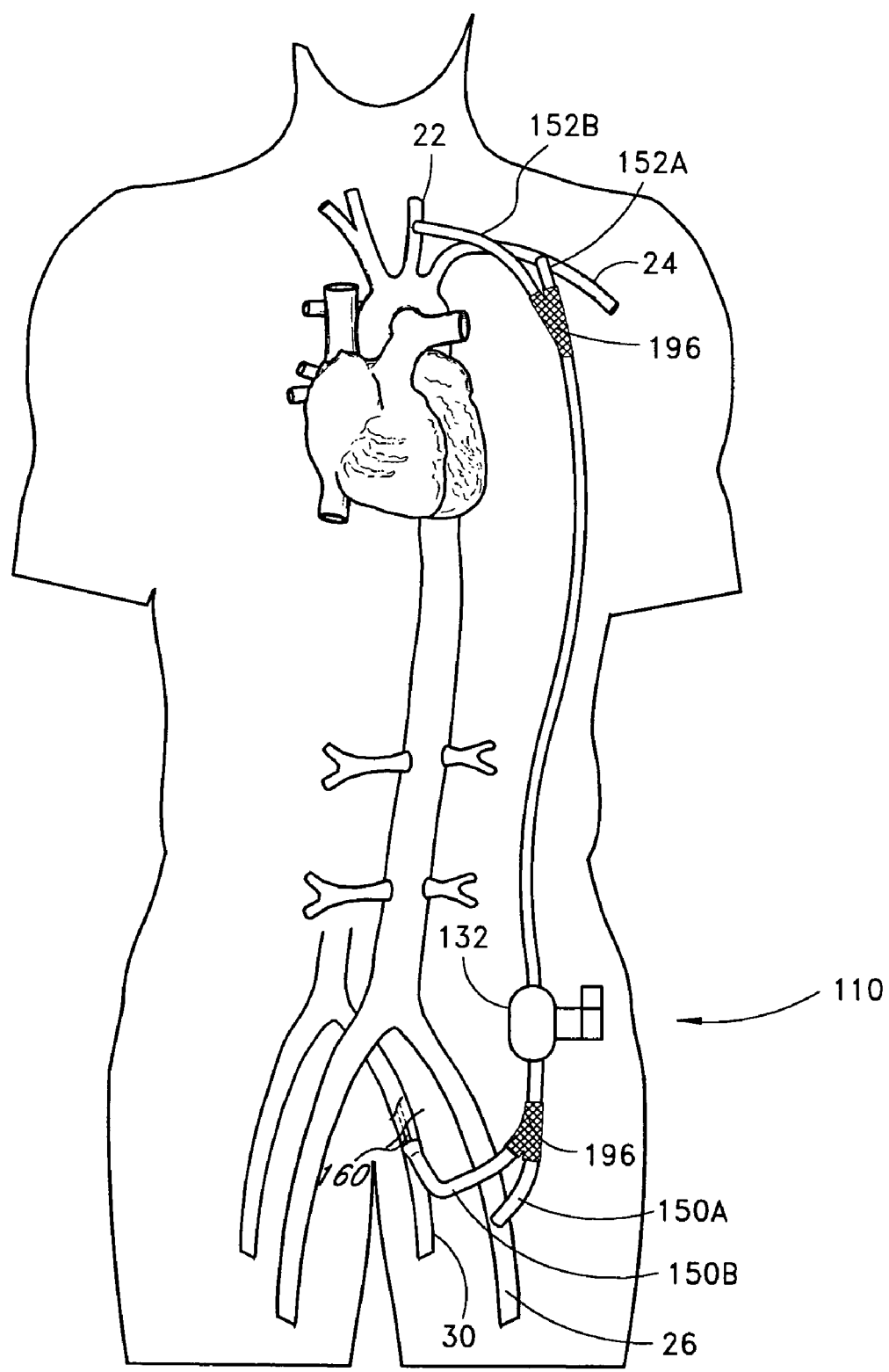
FIG. 3 is a schematic view of another embodiment of a heart assist system having multiple conduits for multi-site application wherein each of the conduits is applied to more than one vessel, shown applied to a patient's vascular system.

FIG. 3 shows another embodiment of a heart assist system 110 applied to the patient 12. For example, the heart assist system 110 includes a pump 132 in fluid communication with a plurality of inflow conduits 150A, 150B and a plurality of outflow conduits 152A, 152B. Each pair of conduits converges at a generally Y-shaped convergence 196 that converges the flow at the inflow end and diverges the flow at the outflow end. Each conduit may be connected to a separate peripheral blood vessel, although it is possible to have two connections to the same blood vessel at remote locations. In one arrangement, all four conduits are connected to peripheral arteries. In another arrangement, one or more of the conduits could be connected to veins. In the arrangement of FIG. 3, the inflow conduit 150A is connected to the left femoral artery 26 while the inflow conduit 150B is connected to the left femoral vein 30. The outflow conduit 152A is connected to the left subclavian artery 24 while the outflow conduit 152B is connected to the left carotid artery 22. Preferably at least one of the conduits 150A, 150B, 152A, and 152B is coupled with a corresponding vessel via a cannula. In the illustrated embodiment, the inflow conduit 150B is coupled with the left femoral vein 30 via a cannula 160. The cannula 160 is coupled in a manner similar to that shown in FIG. 2 and described in connection with the cannula 60. The cannula 160 preferably takes any suitable form. Several particularly useful configurations of the cannula 160 are illustrated in FIGS. 17A-32B, discussed below.

The connections of any or all of the conduits of the system 110 to the blood vessels may be via an anastomosis connection or via a connector, as described below in connection with FIG. 4. In addition, the embodiment of FIG. 3 may be applied to any combination of peripheral blood vessels that would best suit the patient's condition. For example, it may be desired to have one inflow conduit and two outflow conduits or vice versa. It should be noted that more than two conduits may be used on the inflow or outflow side, where the number of inflow conduits is not necessarily equal to the number of outflow conduits.

It is contemplated that, where an anastomosis connection is not desired, a connector may be used to connect at least one of the inflow conduit and the outflow conduit to a peripheral blood vessel. With reference to FIG. 4, an embodiment of a heart assist system 210 is shown, wherein an outflow conduit 252 is connected to a non-primary blood vessel, e.g., the left subclavian artery 24, via a connector 268 that comprises a three-opening fitting. In one embodiment, the connector 268 comprises an intra-vascular, generally T-shaped fitting 270 having a proximal end 272 (with respect to the flow of blood in the left axillary artery and therethrough), a distal end 274, and an angled divergence 276 permitting connection to the outflow conduit 252 and the left subclavian artery 24. The proximal and distal ends 274, 276 of the fittings 272 permit connection to the blood vessel into which the fitting is positioned, e.g., the left subclavian artery 24. The angle of divergence 276 of the fittings 272 may be 90 degrees or less in either direction from the axis of flow through the blood vessel, as optimally selected to generate the needed flow distally toward the hand to prevent limb ischemia, and to insure sufficient flow and pressure toward the aorta to provide the circulatory assistance and workload reduction needed while minimizing or avoiding endothelial damage to the blood vessel. In another embodiment, the connector 268 is a sleeve (not shown) that surrounds and attaches to the outside of the non-primary blood vessel where, within the interior of the sleeve, a port to the blood vessel is provided to permit blood flow from the outflow conduit 252 when the conduit 252 is connected to the connector 268.

Figure 5:
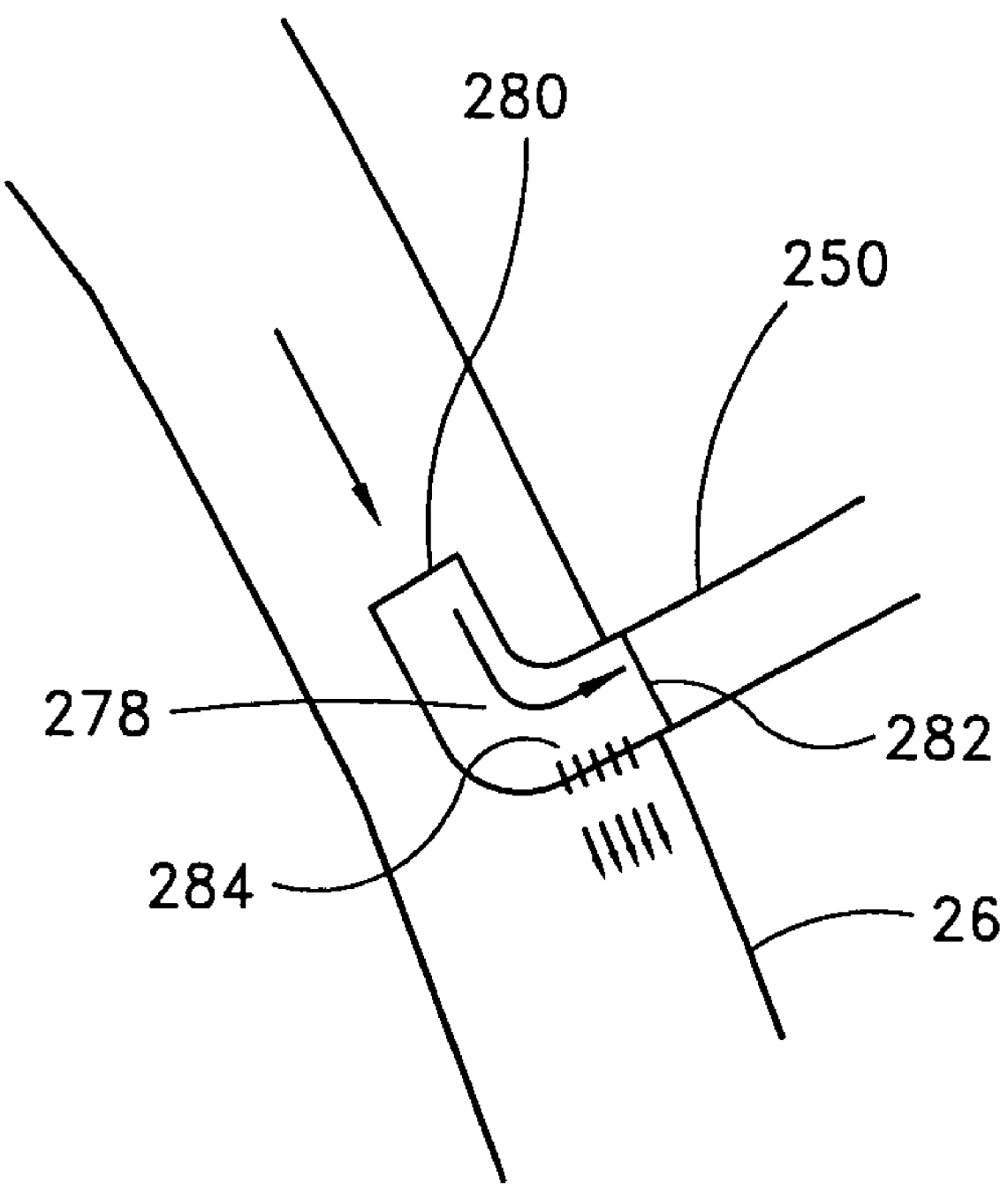
FIG. 5 is a schematic view of an L-shaped connector coupled with an inflow conduit, shown inserted within a blood vessel.

Other types of connectors having other configurations are contemplated that may avoid the need for an anastomosis connection or that permit connection of the conduit(s) to the blood vessel(s). For example, it is contemplated that an L-shaped connector be used if it is desired to withdraw blood more predominantly from one direction of a peripheral vessel or to direct blood more predominantly into a peripheral vessel. Referring to FIG. 5, the inflow conduit 250 is fluidly connected to a peripheral vessel, for example, the left femoral artery 26, using an L-shaped connector 278. Of course the system 210 could be configured so that the outflow conduit 252 is coupled to a non-primary vessel via the L-shaped connector 278 and the inflow conduit 250 is coupled via a cannula, as shown in FIG. 3. The L-shaped connector 278 has an inlet port 280 at a proximal end and an outlet port 282 through which blood flows into the inflow conduit 250. The L-shaped connector 278 also has an arrangement of holes 284 within a wall positioned at a distal end opposite the inlet port 280 so that some of the flow drawn into the L-shaped connector 278 is diverted through the holes 284, particularly downstream of the L-shaped connector 278, as in this application. A single hole 284 in the wall could also be effective, depending upon size and placement. The L-shaped connector 278 may be a deformable L-shaped catheter percutaneously applied to the blood vessel or, in an alternative embodiment, be connected directly to the walls of the blood vessel for more long term application. By directing some blood flow downstream of the L-shaped connector 278 during withdrawal of blood from the vessel, ischemic damage downstream from the connector may be avoided. Such ischemic damage might otherwise occur if the majority of the blood flowing into the L-shaped connector 278 were diverted from the blood vessel into the inflow conduit 252. It is also contemplated that a connection to the blood vessels might be made via a cannula, wherein the cannula is implanted, along with the inflow and outflow conduits.

One advantage of discrete connectors manifests in their application to patients with chronic CHF. A connector eliminates a need for an anastomosis connection between the conduits 250, 252 and the peripheral blood vessels where it is desired to remove and/or replace the system more than one time. The connectors could be applied to the first and second blood vessels semi-permanently, with an end cap applied to the divergence for later quick-connection of the present invention system to the patient. In this regard, a patient might experience the benefit of the heart assist systems described herein periodically, without having to reconnect and redisconnect the conduits 250, 252 from the blood vessels via an anastomosis procedure each time. Each time it is desired to implement any of the embodiments of the heart assist system, the end caps would be removed and a conduit attached to the connector(s) quickly.

Figure 4:
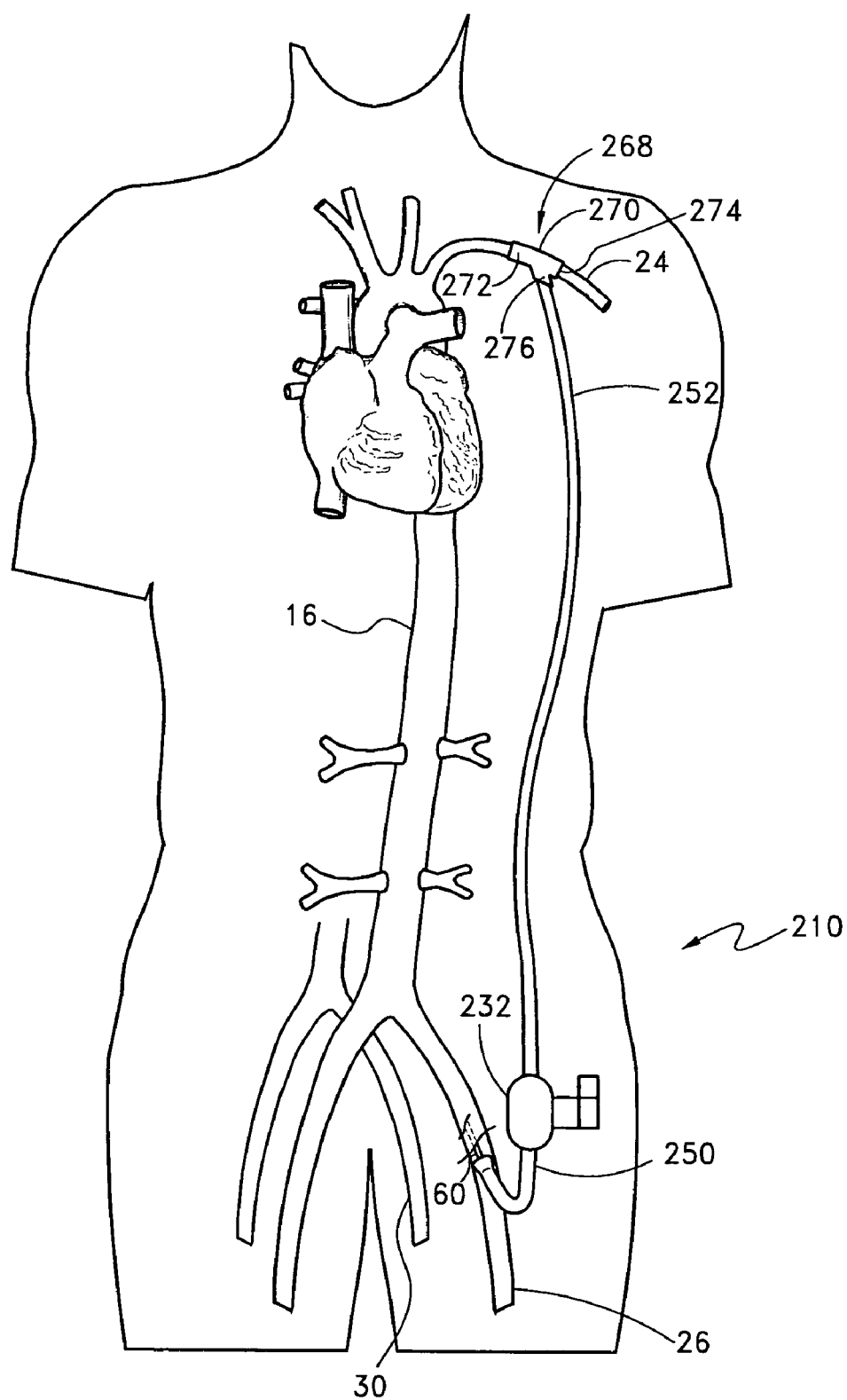
FIG. 4 is a schematic view of another embodiment of a heart assist system having multiple conduits for multi-site application and employing a connector with a T-shaped fitting, shown applied to a patient's vascular system.

In the preferred embodiment of the connector 268, the divergence 276 is oriented at an acute angle significantly less than 90 degrees from the axis of the T-shaped fitting 270, as shown in FIG. 4, so that a majority of the blood flowing through the outflow conduit 252 into the blood vessel (e.g., left subclavian artery 24) flows in a direction proximally toward the heart 14, rather than in the distal direction. In an alternative embodiment, the proximal end 272 of the T-shaped fitting 270 may have a diameter larger than the diameter of the distal end 274, without need of having an angled divergence, to achieve the same result.

With or without a connector, with blood flow directed proximally toward the aorta 16, the result may be concurrent flow down the descending aorta, which will result in the reduction of afterload, impedance, and/or reducing left ventricular end diastolic pressure and volume (preload). Thus, the heart assist systems described herein may be applied so to reduce the afterload on the patient's heart, permitting at least partial if not complete CHF recovery, while supplementing blood circulation. Concurrent flow depends upon the phase of operation of the pulsatile pump and the choice of second blood vessel to which the outflow conduit is connected.

Figure 7:
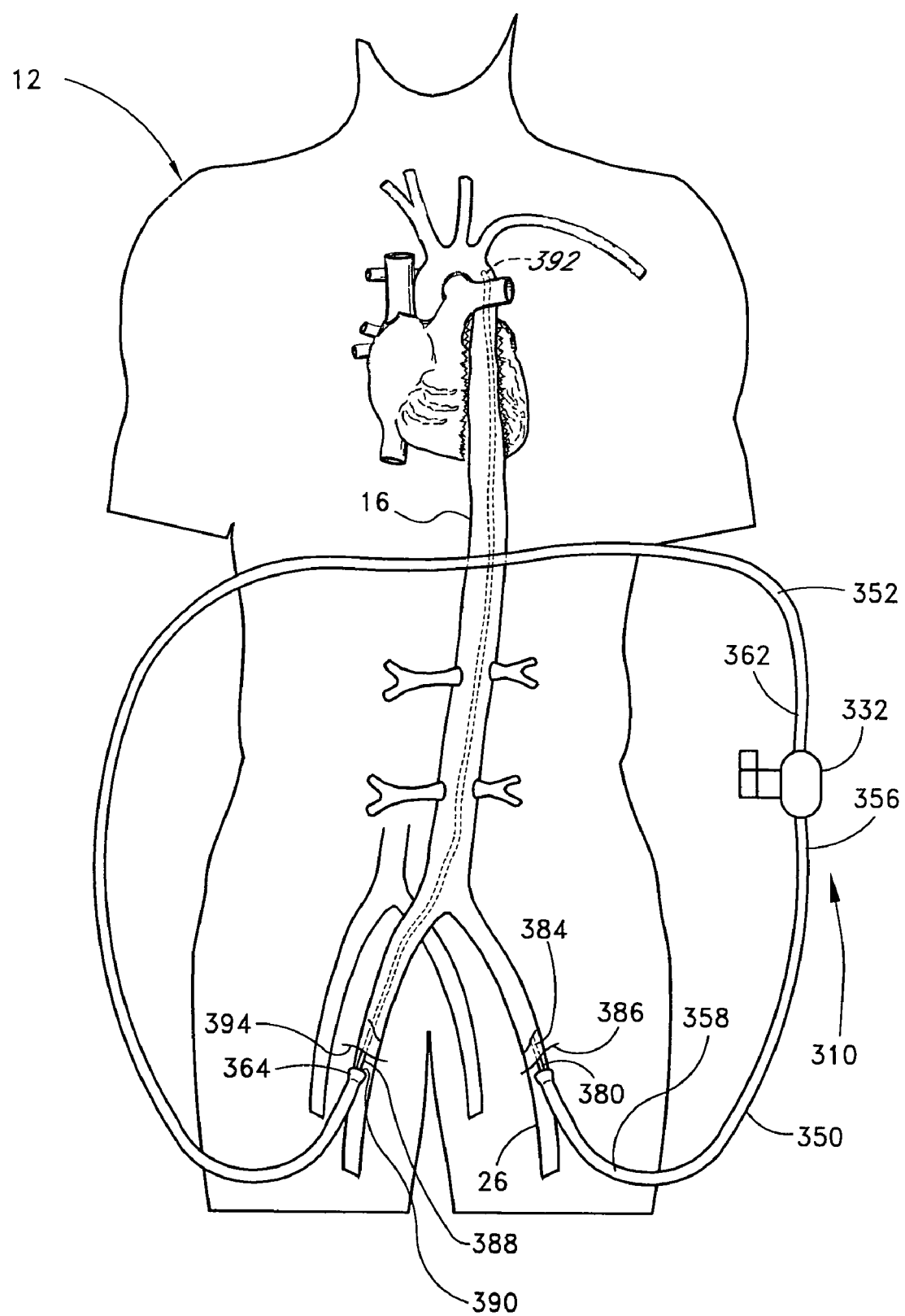
FIG. 7 is a schematic view of another application of the embodiment of FIG. 6, shown applied to a patient's vascular system.

A partial external application of the heart assist systems is contemplated where a patient with heart failure is suffering an acute decomperisation episode; i.e., is not expected to last long, or in the earlier stages of heart failure (where the patient is in New York Heart Association Classification (NYHAC) functional classes II or III). With reference to FIGS. 6 and 7, another embodiment of a heart assist system 310 is applied percutaneously to a patient 312 to connect two non-primary blood vessels wherein a pump 332 and its associated driving means and controls are employed extracorporeally. The pump 332 has an inflow conduit 350 and an outflow conduit 352 associated therewith for connection to two non-primary blood vessels. The inflow conduit 350 has a first end 356 and a second end 358 wherein the second end 358 is connected to a first non-primary blood vessel (e.g., femoral artery 26) by way of an inflow cannula 380. The inflow cannula 380 has a first end 382 sealably connected to the second end 358 of the inflow conduit 350. The inflow cannula 380 also has a second end 384 that is inserted through a surgical opening 386 or an introducer sheath (not shown) and into the blood vessel (e.g., the left femoral artery 26).

Similarly, the outflow conduit 352 has a first end 362 and a second end 364 wherein the second end 364 is connected to a second non-primary blood vessel (e.g., the left subclavian artery 24, as shown in FIG. 6, or the right femoral artery 28, as shown in FIG. 7) by way of an outflow cannula 388. Like the inflow cannula 380, the outflow cannula 388 has a first end 390 sealably connected to the second end 364 of the outflow conduit 352. The outflow cannula 388 also has a second end 392 that is inserted through surgical opening 394 or an introducer sheath (not shown) and into the second blood vessel (e.g., the left subclavian artery 24 or the right femoral artery 28). The cannulae 380 and 388 preferably take any suitable form. Several particularly useful configurations of the cannulae 380, 388 are illustrated in FIGS. 17A-32B, discussed below.

As shown in FIG. 7, the second end 392 of the outflow cannula 388 may extend well into the aorta 16 of the patient 12, for example, proximal to the left subclavian artery. If desired, it may also terminate within the left subclavian artery or the left axillary artery, or in other blood vessels, such as the mesenteric or renal arteries (not shown), where in either case, the outflow cannula 388 has passed through at least a portion of a primary artery (in this case, the aorta 16). Also, if desired, blood drawn into the extracardiac system 310 described herein may originate from the descending aorta (or an artery branching therefrom) and be directed into a blood vessel that is neither the aorta nor pulmonary artery. By use of a percutaneous application, the heart assist system 310 may be applied temporarily without the need to implant any aspect thereof or to make anastomosis connections to the blood vessels.

An alternative variation of the embodiment of FIG. 6 may be used where it is desired to treat a patient periodically, but for short periods of time each occasion and without the use of special connectors. With this variation, it is contemplated that the second ends of the inflow and outflow conduits 350, 352 be more permanently connected to the associated blood vessels via, for example, an anastomosis connection, wherein a portion of each conduit proximate to the blood vessel connection is implanted percutaneously with a removable cap enclosing the externally-exposed first end (or an intervening end thereof) of the conduit external to the patient. When it is desired to provide a circulatory flow path to supplement blood flow, the removable cap on each exposed percutaneously-positioned conduit could be removed and the pump (or the pump with a length of inflow and/or outflow conduit attached thereto) inserted between the exposed percutaneous conduits. In this regard, a patient may experience the benefit of the present invention periodically, without having to reconnect and redisconnect the conduits from the blood vessels each time.

Figure 8:
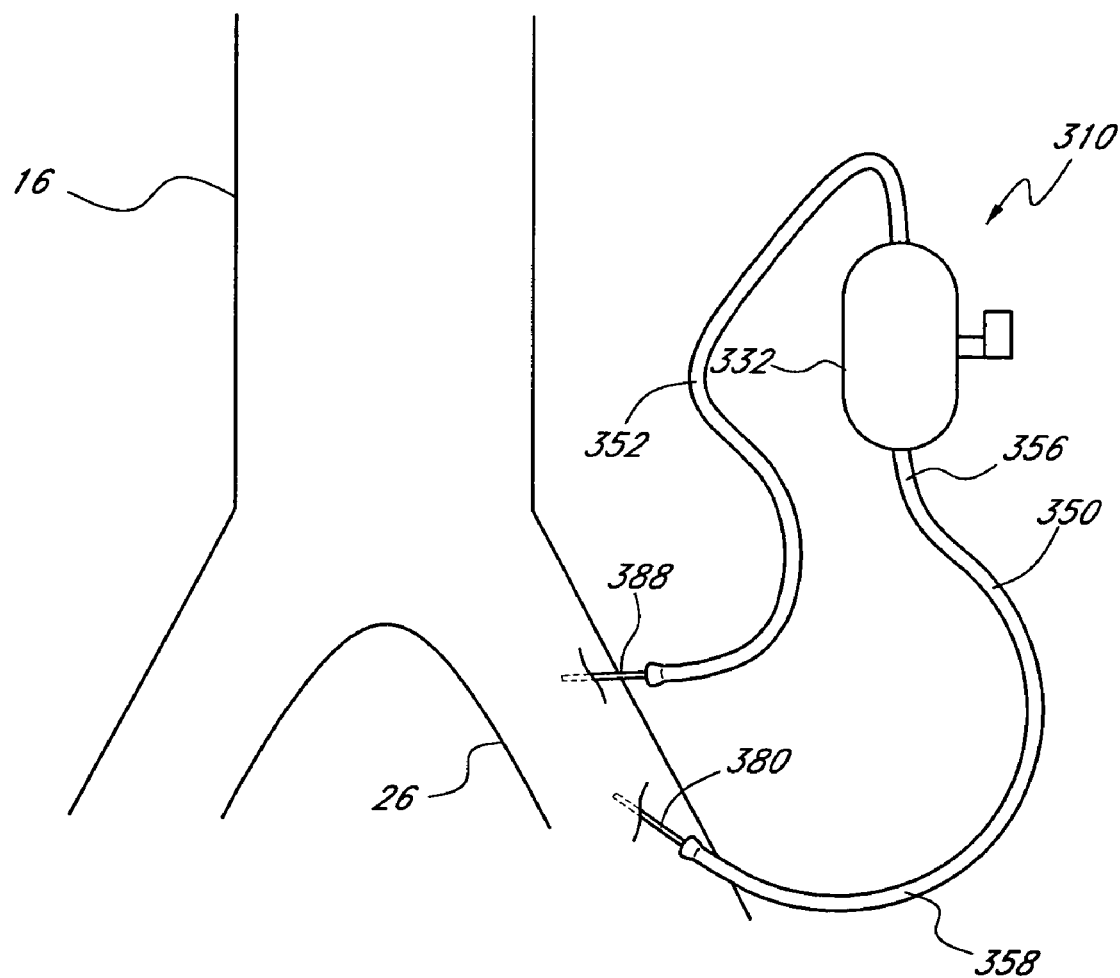
FIG. 8 is a schematic view of another application of the embodiment of FIG. 6, shown applied to a patient's vascular system.

Specific methods of applying this alternative embodiment may further comprise coupling the inflow conduit 352 upstream of the outflow conduit 350 (as shown in FIG. 8), although the reverse arrangement is also contemplated. It is also contemplated that either the cannula 380 coupled with the inflow conduit 350 or the cannula 388 coupled with the outflow conduit 352 may extend through the non-primary blood vessel to a second blood vessel (e.g., through the left femoral artery 26 to the aorta 16 proximate the renal branch) so that blood may be directed from the non-primary blood vessel to the second blood or vice versa.

Figure 9:
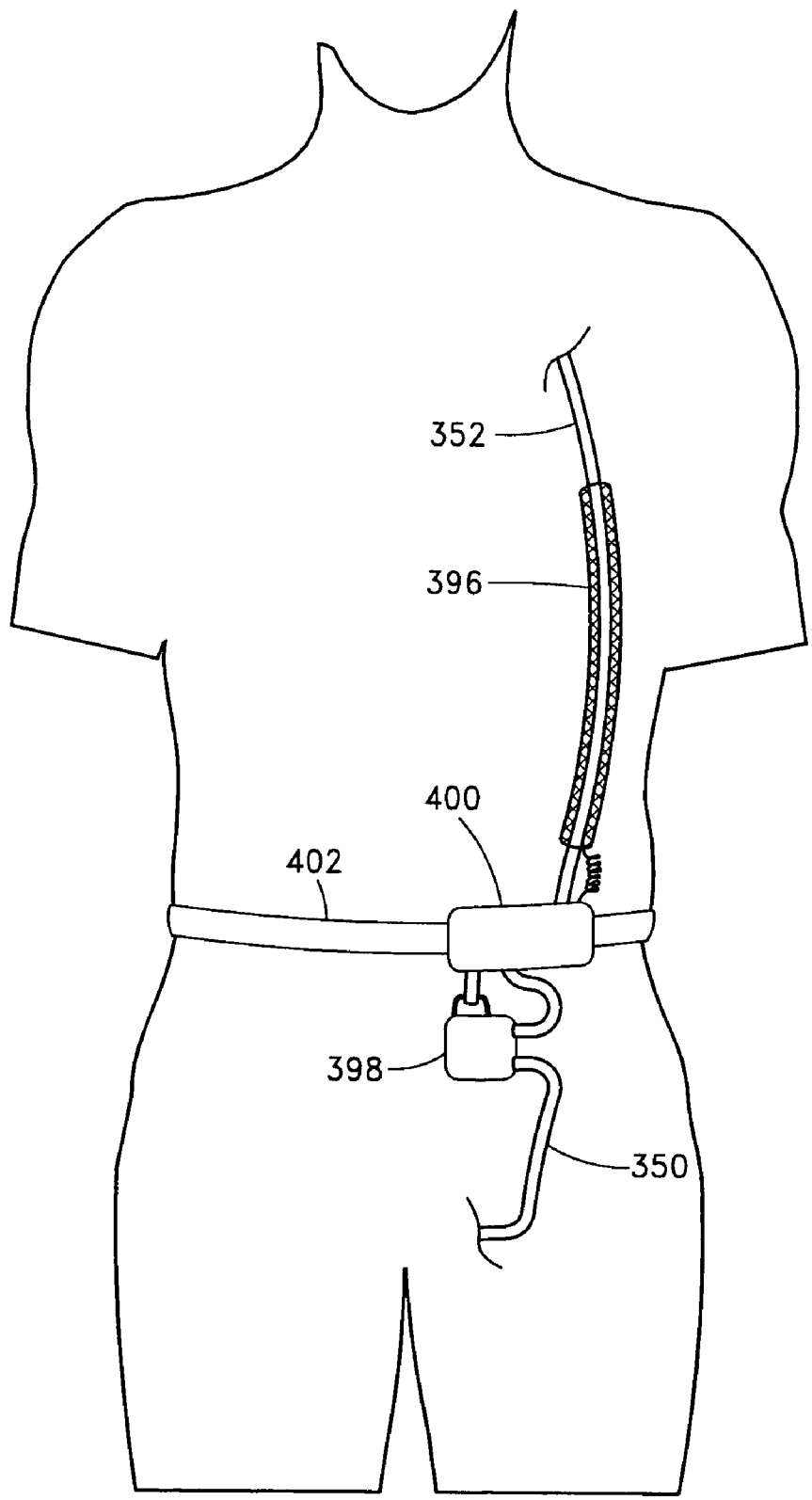
FIG. 9 is a schematic view of another embodiment of a heart assist system having multiple conduits for multi-site application, a reservoir, and a portable housing for carrying a portion of the system directly on the patient.

It is contemplated that a means for minimizing the loss of thermal energy in the patient's blood be provided where any of the heart assist systems described herein are applied extracorporeally. Such means for minimizing the loss of thermal energy may comprise, for example, a heated bath through which the inflow and outflow conduits pass or, alternatively, thermal elements secured to the exterior of the inflow and outflow conduits. Referring to FIG. 9, one embodiment comprises an insulating wrap 396 surrounding the outflow conduit 352 having one or more thermal elements passing therethrough. The elements may be powered, for example, by a battery (not shown). One advantage of thermal elements is that the patient may be ambulatory, if desired. Other means that are known by persons of ordinary skill in the art for ensuring that the temperature of the patient's blood remains at acceptable levels while traveling extracorporeally are also contemplated.

If desired, the present inventive system may further comprise a reservoir that is either contained within or in fluid communication with the inflow conduit. This reservoir is preferably made of materials that are nonthrombogenic. Referring to FIG. 9, a reservoir 398 is positioned fluidly in line with the inflow conduit 350. The reservoir 398 serves to sustain adequate blood in the system when the pump demand exceeds momentarily the volume of blood available in the peripheral blood vessel in which the inflow conduit resides until the pump output can be adjusted. The reservoir 398 reduces the risk of excessive drainage of blood from the peripheral blood vessel, which may occur when cardiac output falls farther than the already diminished baseline level of cardiac output, or when there is systemic vasodilation, as can occur, for example, with septic shock. It is contemplated that the reservoir 398 would be primed with an acceptable solution, such as saline, when the present system is first applied to the patient.

As explained above, one of the advantages of several embodiments of the heart assist system is that such systems permit the patient to be ambulatory. If desired, the systems may be designed portably so that it may be carried directly on the patient. Referring to FIG. 9, this may be accomplished through the use of a portable case 400 with a belt strap 402 to house the pump, power supply and/or the controller, along with certain portions of the inflow and/or outflow conduits, if necessary. It may also be accomplished with a shoulder strap or other techniques, such as a backpack or a fanny pack, that permit effective portability. As shown in FIG. 9, blood is drawn through the inflow conduit 350 into a pump contained within the portable case 400, where it is discharged into the outflow conduit 352 back into the patient.

B. Heart Assist Systems and Methods Employing Single-Site Application

As discussed above, heart assist systems can be applied to a patient through a single cannulation site. Such single-site systems can be configured with a pump located outside the vasculature of a patient, e.g., as extravascular pumping systems, inside the vasculature of the patient, e.g., as intravascular systems, or a hybrid thereof, e.g., partially inside and partially outside the vasculature of the patient.

1. Single-Site Application of Extravascular Pumping Systems

Figure 10:
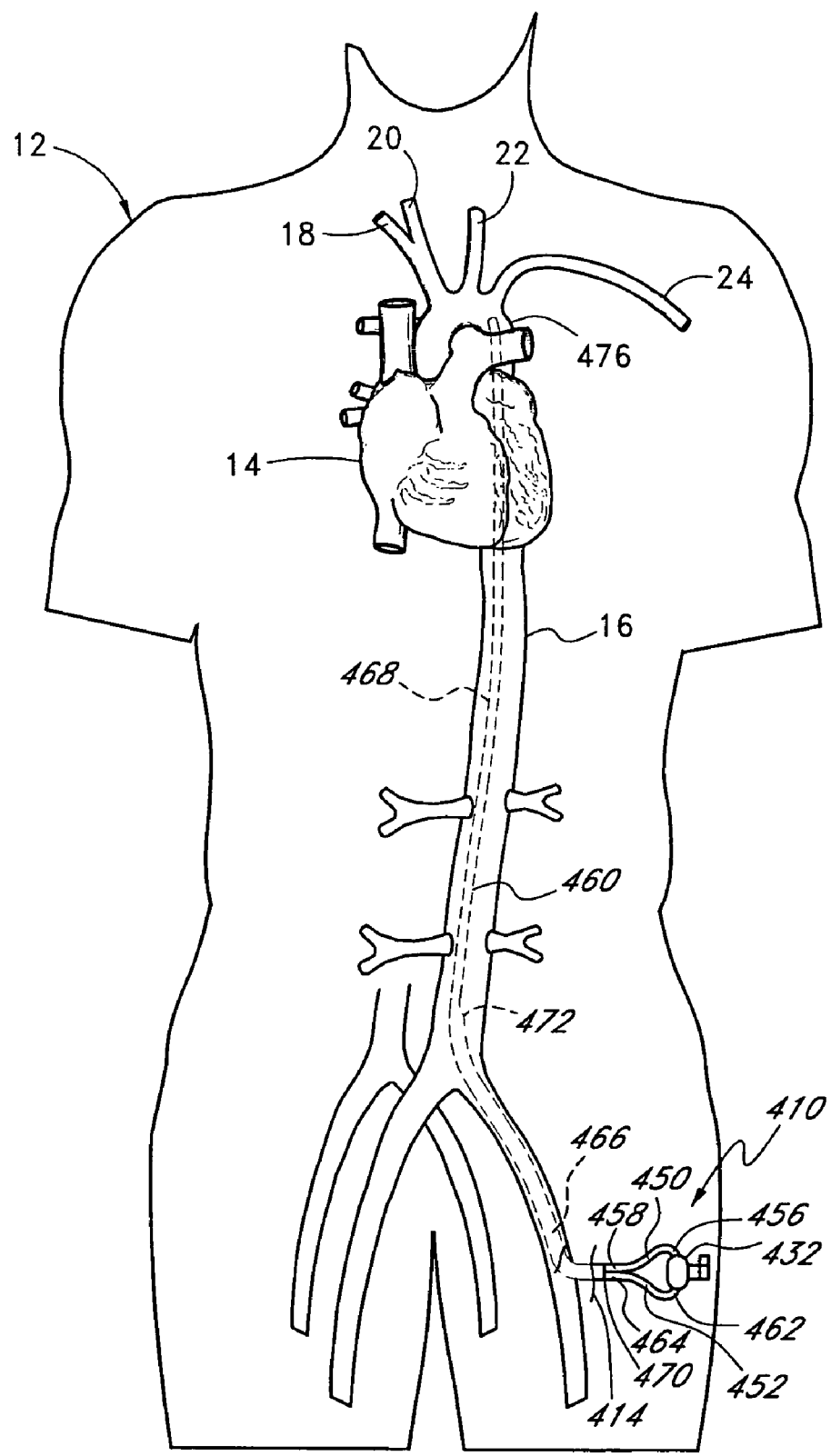
FIG. 10 is a schematic view of another embodiment of a heart assist system having a multilumen cannula for single-site application, shown applied to a patient's vascular system.
Figure 11:
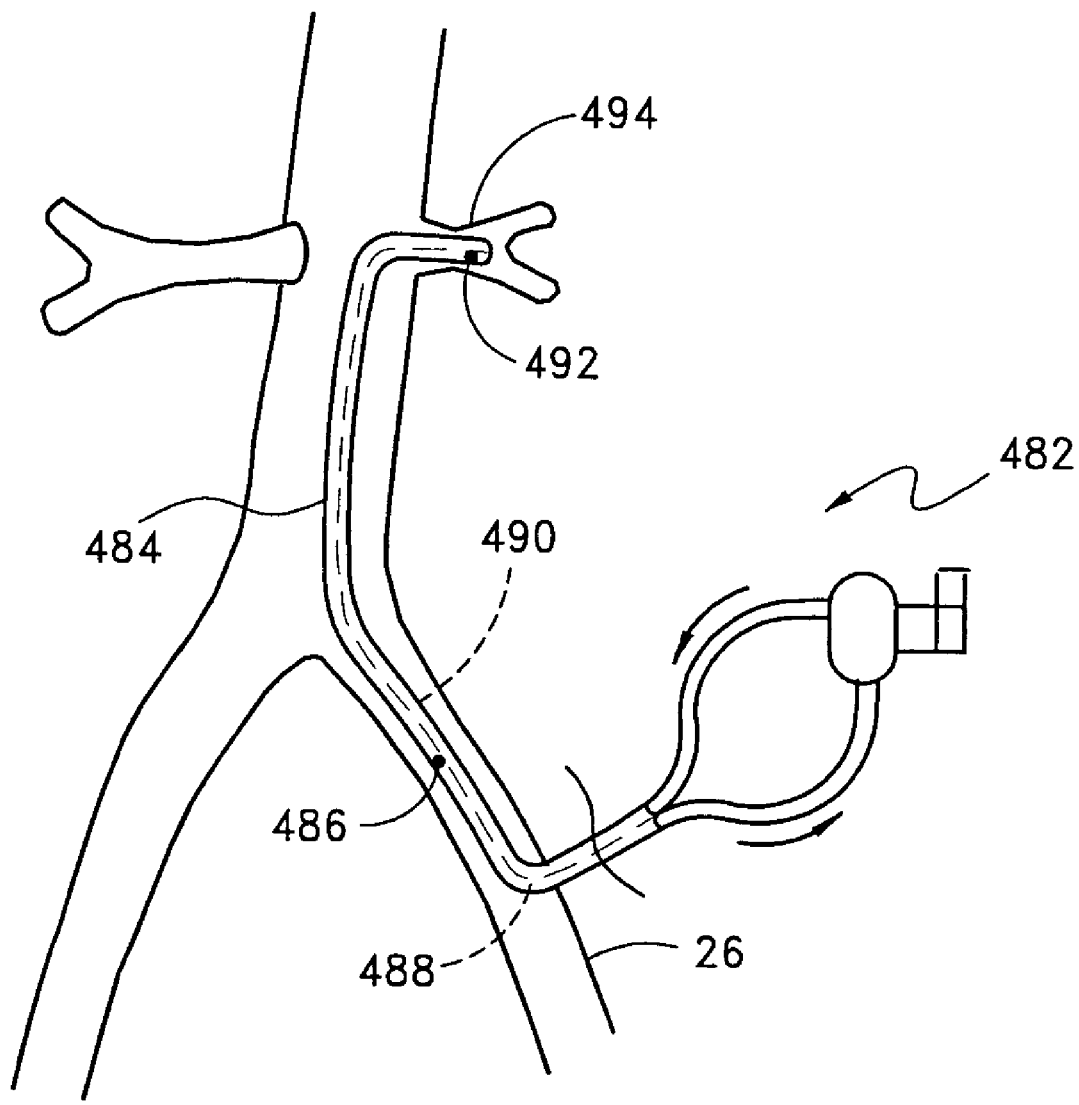
FIG. 11 is a schematic view of a modified embodiment of the heart assist system of FIG. 10, shown applied to a patient's vascular system.

FIGS. 10 and 11 illustrate extracardiac heart assist systems that employ an extravascular pump and that can be applied through as a single-site system. FIG. 10 shows a system 410 that is applied to a patient 12 through a single cannulation site 414 while inflow and outflow conduits fluidly communicate with non-primary vessels. The heart assist system 410 is applied to the patient 12 percutaneously through a single site to couple two blood vessels with a pump 432. The pump 432 can have any of the features described in connection the pump 32. The pump 432 has an inflow conduit 450 and an outflow conduit 452 associated therewith. The inflow conduit 450 has a first end 456 and a second end 458. The first end 456 of the inflow conduit 450 is connected to the inlet of the pump 432 and the second end 458 of the inflow conduit 450 is fluidly coupled with a first non-primary blood vessel (e.g., the femoral artery 26) by way of a multilumen cannula 460. Similarly, the outflow conduit 452 has a first end 462 and a second end 464. The first end 462 of the outflow conduit 452 is connected to the outlet of the pump 432 and the second end 464 of the outflow conduit 452 is fluidly coupled with a second blood vessel (e.g., the descending aorta 16) by way of the multilumen cannula 460.

In one embodiment, the multilumen cannula 460 includes a first lumen 466 and a second lumen 468. The first lumen 466 extends from a proximal end 470 of the multilumen cannula 460 to a first distal end 472. The second lumen 468 extends from the proximal end 470 to a second distal end 474. In the illustrated embodiment, the second end 458 of the inflow conduit 450 is connected to the first lumen 466 of the multilumen cannula 460 and the second end 464 of the outflow conduit 452 is connected to the second lumen 468 of the multilumen cannula 460.

Where there is a desire for the patient 12 to be ambulatory, the multilumen cannula 460 preferably is made of material sufficiently flexible and resilient to permit the patient 12 to be comfortably move about while the multilumen cannula 460 is indwelling in the patient's blood vessels without causing any vascular trauma.

The application shown in FIG. 10 and described above results in flow from the first distal end 472 to the second distal end 474. Of course, the flow direction may be reversed using the same arrangement, resulting in flow from the distal end 474 to the distal end 472. In some applications, the system 410 is applied in an arterial-arterial fashion. For example, as illustrated, the multilumen cannula 460 can be inserted into the left femoral artery 26 of the patient 12 and guided superiorly through the descending aorta to one of numerous locations. In one application, the multilumen cannula 460 can be advanced until the distal end 474 is located in the aortic arch 476 of the patient 12. The blood could discharge, for example, directly into the descending aorta proximate an arterial branch, such as the left subclavian artery or directly into the peripheral mesenteric artery (not shown).

The pump 432 draws blood from the patient's vascular system in the area near the distal end 472 and into the lumen 466. This blood is further drawn into the lumen of the conduit 450 and into the pump 432. The pump 432 then expels the blood into the lumen of the outflow conduit 452, which carries the blood into the lumen 468 of the multilumen cannula 460 and back into the patient's vascular system in the area near the distal end 474.

FIG. 11 shows another embodiment of a heart assist system 482 that is similar to the heart assist system 410, except as set forth below. The system 482 employs a multilumen cannula 484. In one application, the multilumen cannula 484 is inserted into the left femoral artery 26 and guided superiorly through the descending aorta to one of numerous locations. Preferably, the multilumen cannula 484 has an inflow port 486 that is positioned in one application within the left femoral artery 26 when the cannula 484 is fully inserted so that blood drawn from the left femoral artery 26 is directed through the inflow port 486 into a first lumen 488 in the cannula 484. The inflow port 486 can also be positioned in any other suitable location within the vasculature, described herein or apparent to one skilled in the art. This blood is then pumped through a second lumen 490 in the cannula 484 and out through an outflow port 492 at the distal end of the cannula 484. The outflow port 492 may be situated within, for example, a mesenteric artery 494 such that blood flow results from the left femoral artery 26 to the mesenteric artery 494. The blood could discharge, for example, directly into the descending aorta proximate an arterial branch, such as the renal arteries, the left subclavian artery, or directly into the peripheral mesenteric artery 494, as illustrated in FIG. 11. Where there is a desire for the patient to be ambulatory, the multilumen cannula 484 preferably is made of material sufficiently flexible and resilient to permit the patient 12 to comfortably move about while the cannula 484 is indwelling in the patient's blood vessels without causing any vascular trauma.

Figure 12:
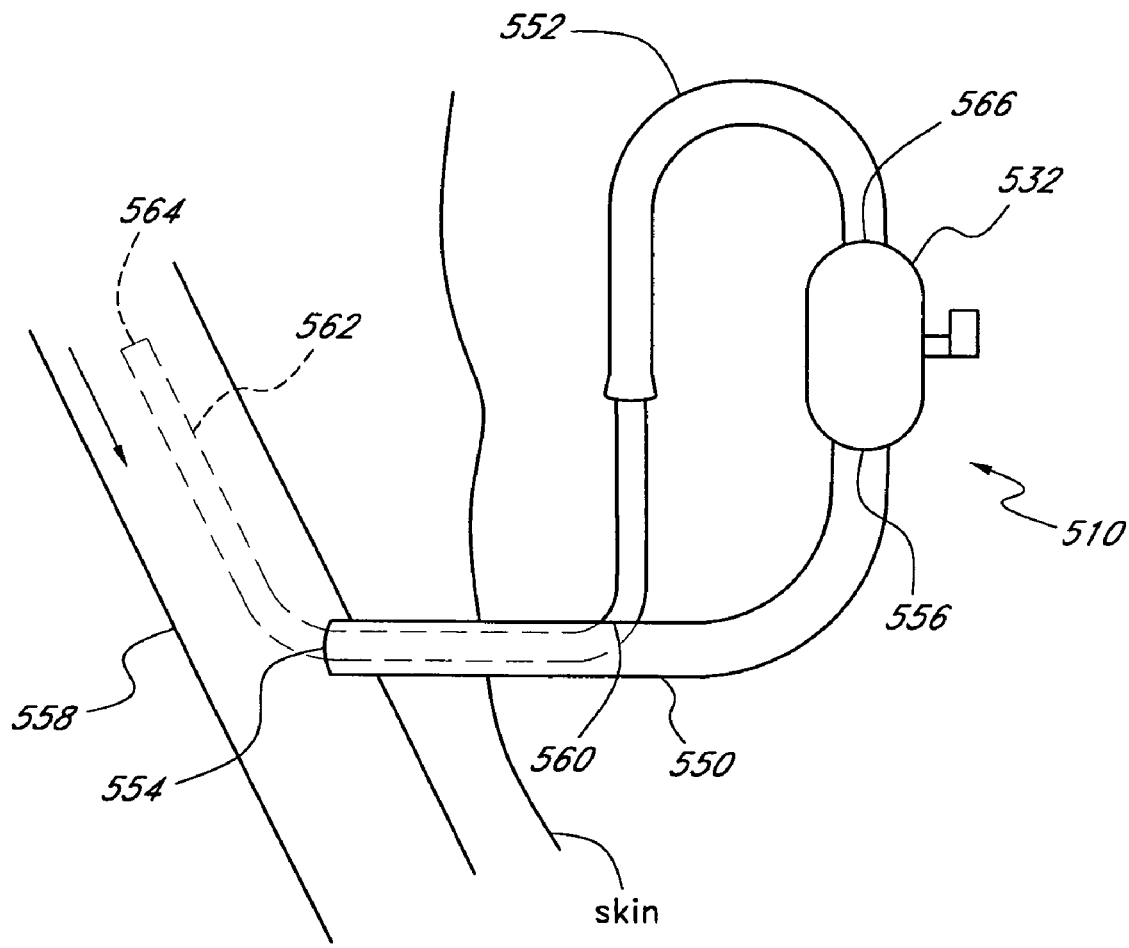
FIG. 12 is a schematic view of another embodiment of a heart assist system having multiple conduits for single-site application, shown applied to a patient's circulatory system.

Further details of features that may be incorporated into the cannulae, such as the multilumen cannula 460 and the other cannulae described herein are described below in connection with FIGS. 11 and 17-27 and may be found in U.S. patent application Ser. No. 10/078,283, filed Feb. 14, 2002, entitled A MULTILUMEN CATHETER FOR MINIMIZING LIMB ISCHEMIA, U.S. patent application Ser. No. 10/706,346, filed Nov. 12, 2003, entitled CANNULAE HAVING REDIRECTING TIP, U.S. patent application Ser. No. 10/686,040, filed Oct. 15, 2003, entitled IMPLANTABLE HEART ASSIST SYSTEM AND METHOD OF APPLYING SAME, U.S. patent application Ser. No. 10/735,413, filed Dec. 12, 2003, entitled CANNULAE FOR SELECTIVELY ENHANCING BLOOD FLOW, an application corresponding to entitled SYSTEM INCLUDING A CANNULA HAVING REDUCED FLOW RESISTANCE, filed Jun. 10, 2004, and an application corresponding to entitled CANNULA HAVING REDUCED FLOW RESISTANCE, filed Jun. 10, 2004 which are hereby expressly incorporated by reference in its entirety and made a part of this specification FIG. 12 shows another heart assist system 510 that takes further advantage of the supplemental blood perfusion and heart load reduction benefits while remaining minimally invasive in application. The heart assist system 510 is an extracardiac pumping system that includes a pump 532, an inflow conduit 550 and an outflow conduit 552. In the illustrated embodiment, the inflow conduit 550 comprises a vascular graft. The vascular graft conduit 550 and the outflow conduit 552 are fluidly coupled to pump 532. The pump 532 is configured to pump blood through the patient at subcardiac volumetric rates, and has an average flow rate that, during normal operation thereof, is substantially below that of the patient's heart when healthy. In one variation, the pump 532 may be a rotary pump. Other pumps described herein, or any other suitable pump can also be used in the extracardiac pumping system 510. In one application, the pump 532 is configured so as to be implantable.

The vascular graft 550 has a first end 554 and a second end 556. The first end 554 is sized and configured to couple to a non-primary blood vessel 558 subcutaneously to permit application of the extracardiac pumping system 510 in a minimally-invasive procedure. In one application, the vascular graft conduit 550 is configured to couple to the blood vessel 558 via an anastomosis connection. The second end 556 of the vascular graft 550 is fluidly coupled to the pump 532 to conduct blood between the non-primary blood vessel 558 and the pump 532. In the embodiment shown, the second end 556 is directly connected to the pump 532, but, as discussed above in connection with other embodiments, intervening fluid conducting elements may be interposed between the second end 556 of the vascular graft 550 and the pump 532. Examples of arrangements of vascular graft conduits may be found in U.S. application Ser. No. 09/780,083, filed Feb. 9, 2001, entitled EXTRA-CORPOREAL VASCULAR CONDUIT, which is hereby incorporated by reference in its entirety and made a part of this specification.

FIG. 12 illustrates that the present inventive embodiment further comprises means for coupling the outflow conduit 552 to the vascular graft 550, which may comprise in one embodiment an insertion site 560. In the illustrated embodiment, the insertion site 560 is located between the first end 554 and the second end 556 of the vascular graft 550. The outflow conduit 552 preferably is coupled with a cannula 562. The cannula 562 preferably takes any suitable form. Several particularly useful configurations of the cannula 562 are illustrated in FIGS. 17A-32B, discussed below.

The insertion site 560 is configured to receive the cannula 562 therethrough in a sealable manner in the illustrated embodiment. In another embodiment, the insertion site 560 is configured to receive the outflow conduit 552 directly. The cannula 562 includes a first end 564 sized and configured to be inserted through the insertion site 560, through the cannula 550, and through the non-primary blood vessel 558. The conduit 552 has a second end 566 fluidly coupled to the pump 532 to conduct blood between the pump 532 and the blood vessel 558.

The extracardiac pumping system 510 can be applied to a patient, as shown in FIG. 12, so that the outflow conduit 552 provides fluid communication between the pump 532 and a location upstream or downstream of the point where the cannula 562 enters the non-primary blood vessel 558. In another application, the cannula 562 is directed through the blood vessel to a different blood vessel, upstream or downstream thereof. Although the vascular graft 550 is described above as an "inflow conduit" and the conduit 552 is described above as an "outflow conduit," in another application of this embodiment, the blood flow through the pumping system 510 is reversed (i.e., the pump 532 pumps blood in the opposite direction), whereby the vascular graft 550 is an outflow conduit and the conduit 552 is an inflow conduit.

Figure 13:
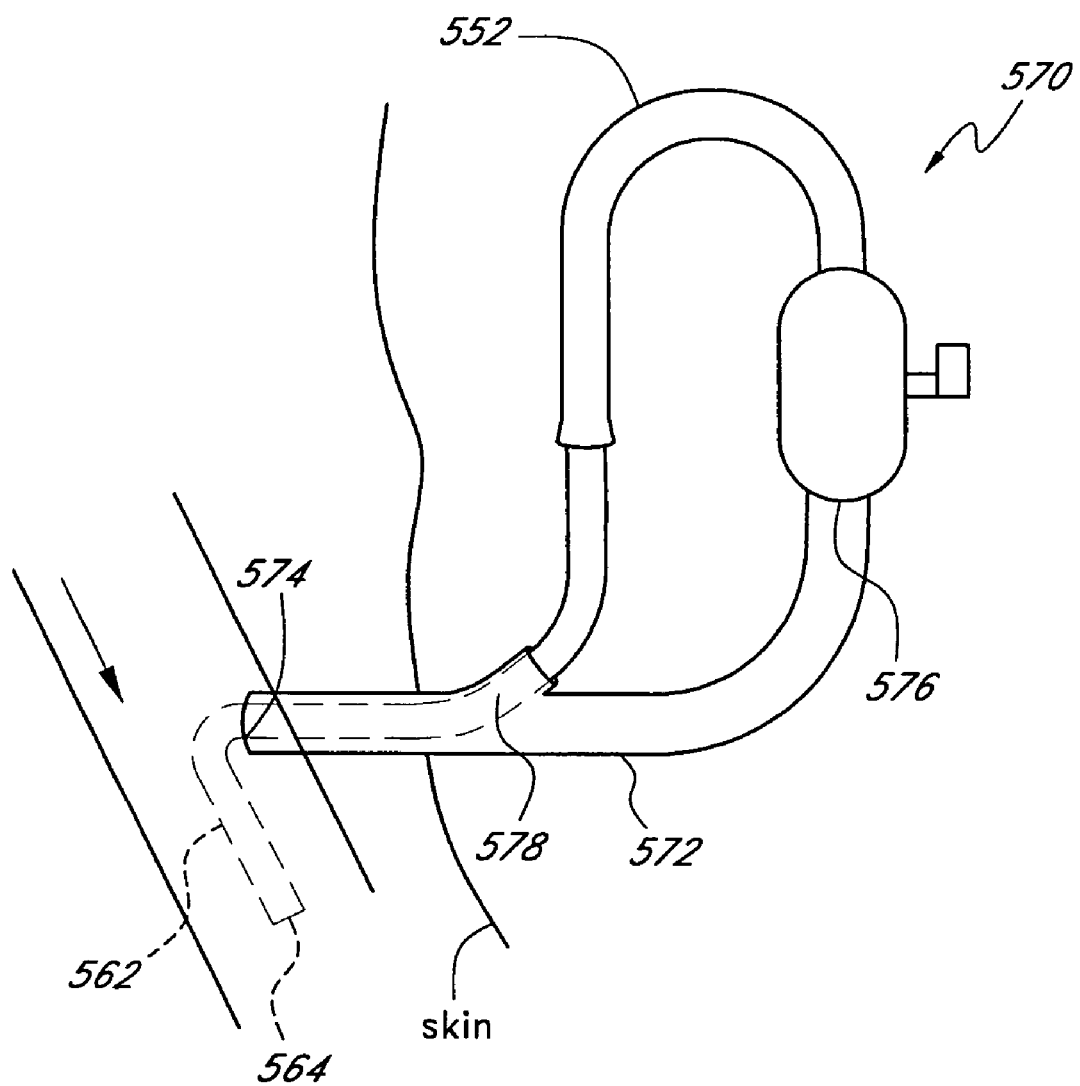
FIG. 13 is a schematic view of another application of the embodiment of FIG. 12, shown applied to a patient's vascular system.

FIG. 13 shows a variation of the extracardiac pumping system shown in FIG. 12. In particular, a heart assist system 570 includes an inflow conduit 572 that comprises a first end 574, a second end 576, and means for connecting the outflow conduit 552 to the inflow conduit 572. In one embodiment, the inflow conduit 572 comprises a vascular graft. The extracardiac pumping system 570 is otherwise similar to the extracardiac pumping system 510. The means for connecting the conduit 552 to the inflow conduit 572 may comprise a branched portion 578. In one embodiment, the branched portion 578 is located between the first end 574 and the second end 576. The branched portion 578 is configured to sealably receive the distal end 564 of the outflow conduit 552. Where, as shown, the first end 564 of the outflow conduit 552 comprises the cannula 562, the branched portion 578 is configured to receive the cannula 562. The inflow conduit 572 of this arrangement comprises in part a multilumen cannula, where the internal lumen extends into the blood vessel 558. Other multilumen catheter arrangements are shown in U.S. application Ser. No. 10/078,283, incorporated by reference herein above.

2. Single-Site Application of Intravascular Pumping Systems

Figure 14:
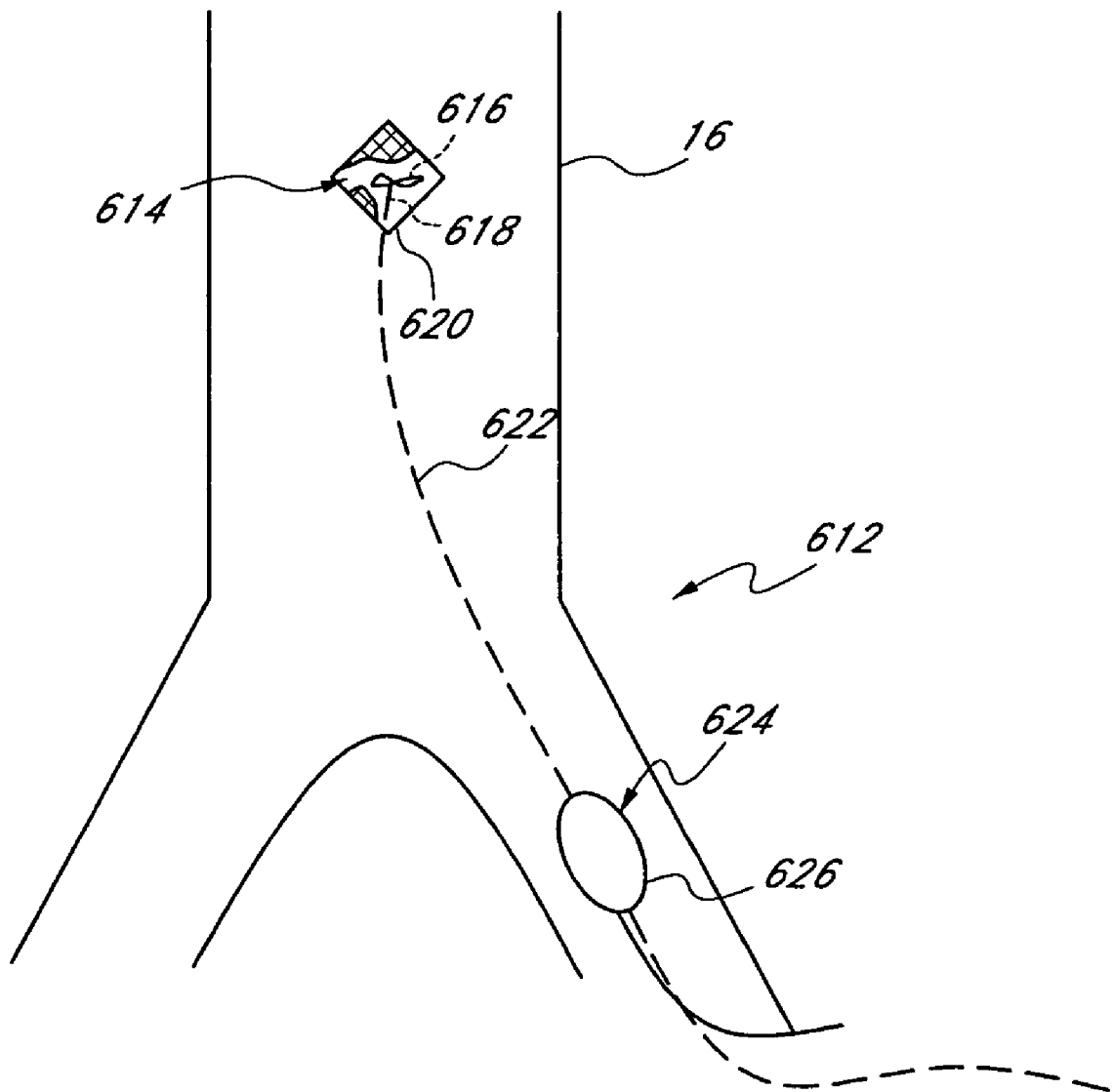
FIG. 14 is a schematic view of one application of an embodiment of a heart assist system having an intravascular pump enclosed in a protective housing, wherein the intravascular pump is inserted into the patient's vasculature through a non-primary vessel.
Figure 15:
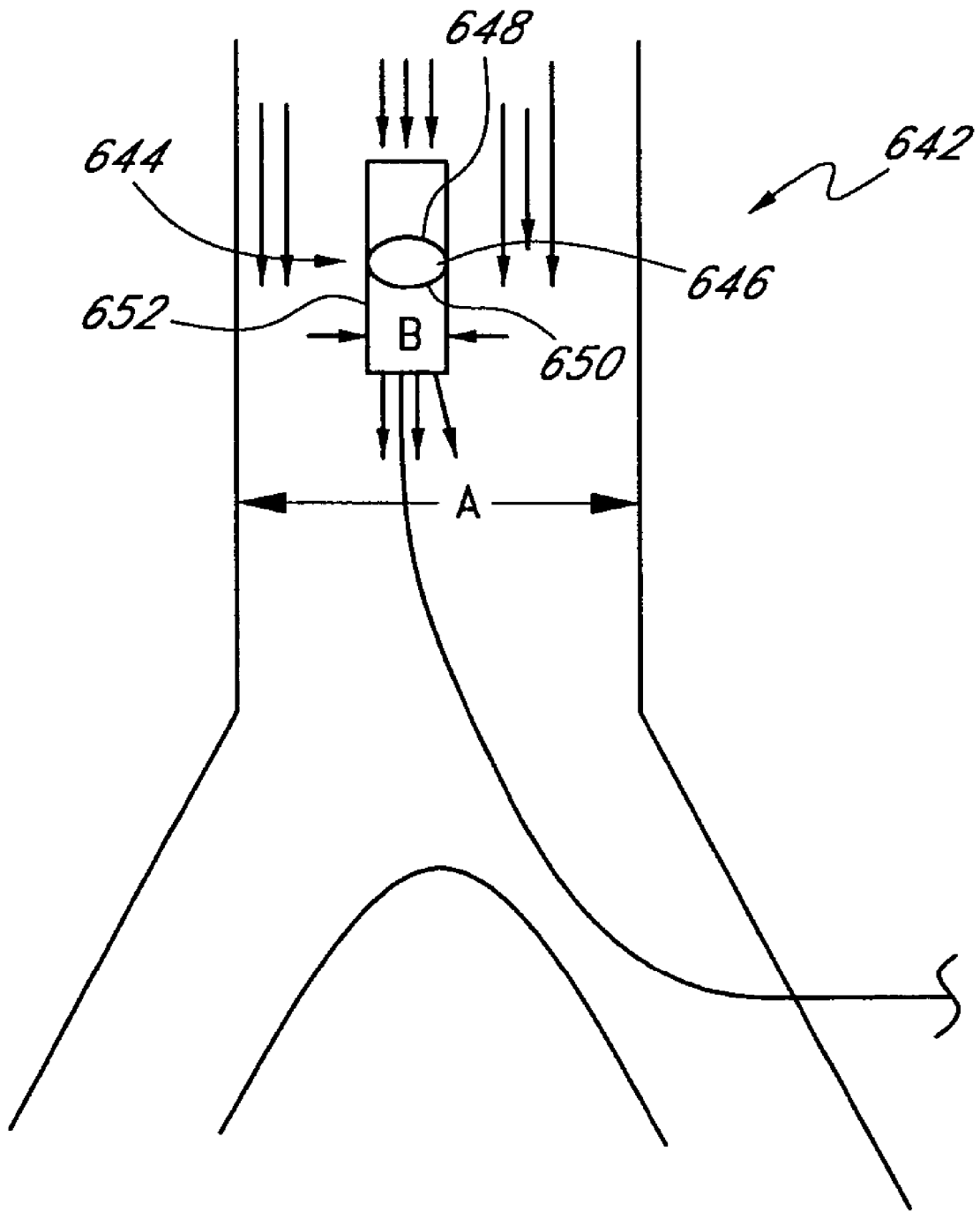
FIG. 15 is a schematic view of another embodiment of a heart assist system having an intravascular pump housed within a conduit having an inlet and an outlet, wherein the intravascular pump is inserted into the patient's vasculature through a non-primary vessel.

FIG. 14-16 illustrate extracardiac heart assist systems that employ intravascular pumping systems. Such systems take further advantage of the supplemental blood perfusion and heart load reduction benefits discussed above while remaining minimally invasive in application. Specifically, it is contemplated to provide an extracardiac pumping system that comprises a pump that is sized and configured to be at least partially implanted intravascularly in any location desirable to achieve those benefits, while being insertable through a non-primary vessel.

FIG. 14 shows a heart assist system 612 that includes a pumping means 614 comprising preferably one or more rotatable impeller blades 616, although other types of pumping means 614 are contemplated, such as an Archimedes screw, a worm pump, or other means by which blood may be directed axially along the pumping means from a point upstream of an inlet to the pumping means to a point downstream of an outlet from the pumping means. Where one or more impeller blades 616 are used, such as in a rotary pump, such impeller blades 616 may be supported helically or otherwise on a shaft 618 within a housing 620. The housing 620 may be open, as shown, in which the walls of the housing 620 are open to blood flow therethrough. The housing 620 may be entirely closed, if desired, except for an inlet and outlet (not shown) to permit blood flow therethrough in a more channel fashion. For example, the housing 620 could be coupled with or replaced by a cannula with a redirecting tip portion, such as those illustrated in FIGS. 17A-32B. The heart assist system 612 serves to supplement the kinetic energy of the blood flow through the blood vessel in which the pump is positioned, e.g., the aorta 16.

The impeller blade(s) 616 of the pumping means 614 of this embodiment may be driven in one or a number of ways known to persons of ordinary skill in the art. In the embodiment shown in FIG. 14, the impeller blade(s) 616 are driven mechanically via a rotatable cable or drive wire 622 by driving means 624, the latter of which may be positioned corporeally (intra- or extra-vascularly) or extracorporeally. As shown, the driving means 624 may comprise a motor 626 to which energy is supplied directly via an associated battery or an external power source, in a manner described in more detail herein. It is also contemplated that the impeller blade(s) 616 be driven electromagnetically through an internal or external electromagnetic drive. Preferably, a controller (not shown) is provided in association with this embodiment so that the pumping means 614 may be controlled to operate in a continuous and/or pulsatile fashion, as described herein.

Variations of the intravascular embodiment of FIG. 14 are shown in FIGS. 15 and 16. In the embodiment of FIG. 15, an intrasvascular extracardiac system 642 comprising a pumping means 644, which may be one of several means described herein. The pumping means 644 may be driven in any suitable manner, including means sized and configured to be implantable and, if desired, implantable intravascularly, e.g., as discussed above. For a blood vessel (e.g., descending aorta) having a diameter "A", the pumping means 644 preferably has a meaningfully smaller diameter "B". The pumping means 644 may comprise a pump 646 having an inlet 648 and an outlet 650. The pumping means 644 also comprises a pump driven mechanically by a suitable drive arrangement in one embodiment. Although the vertical arrows in FIG. 15 illustrate that the pumping means 644 pumps blood in the same direction as the flow of blood in the vessel, the pumping means 644 could be reversed to pump blood in a direction generally opposite of the flow in the vessel.

In one embodiment, the pumping means 644 also includes a conduit 652 in which the pump 646 is housed. The conduit 652 may be relatively short, as shown, or may extend well within the designated blood vessel or even into an adjoining or remote blood vessel at either the inlet end, the outlet end, or both. The intravascular extracardiac system 642 may further comprise an additional parallel-flow conduit, as discussed below in connection with the system of FIG. 16.

The intrasvascular extracardiac system 642 may further comprise inflow and/or outflow conduits or cannulae (not shown) fluidly connected to the pumping means 644, e.g., to the inlet and outlet of pump 646. Any suitable conduit or cannula can be employed. For example, a cannula having a redirecting tip portion, such as the any of the cannulae of FIGS. 17A-32B, could be coupled with an intrasvascular extracardiac system.

In another embodiment, an intrasvascular pumping means 644 may be positioned within one lumen of a multilumen catheter so that, for example, where the catheter is applied at the left femoral artery, a first lumen may extend into the aorta proximate the left subclavian and the pumping means may reside at any point within the first lumen, and the second lumen may extend much shorter just into the left femoral or left iliac. Such a system is described in greater detail in U.S. application Ser. No. 10/078,283, incorporated by reference herein above.

FIG. 16 shows a variation of the heart assist system of FIG. 15. In particular the intravascular system may further comprise an additional conduit 660 positioned preferably proximate the pumping means 644 to provide a defined flow path for blood flow axially parallel to the blood flowing through the pumping means 644. In the case of the pumping means 644 of FIG. 16, the means comprises a rotatable cable 662 having blood directing means 664 supported therein for directing blood axially along the cable. Other types of pumping means are also contemplated, if desired, for use with the additional conduit 660.

The intravascular extracardiac system described herein may be inserted into a patient's vasculature in any means known by one of ordinary skill or obvious variant thereof. In one method of use, such a system is temporarily housed within a catheter that is inserted percutaneously, or by surgical cutdown, into a non-primary blood vessel and advanced through to a desired location. The catheter preferably is then withdrawn away from the system so as not to interfere with operation of the system, but still permit the withdrawal of the system from the patient when desired. Further details of intravascular pumping systems may be found in U.S. patent application Ser. No. 10/686,040, filed Oct. 15, 2003, which is hereby incorporated by reference herein in its entirety.

C. Potential Enhancement of Systemic Arterial Blood Mixing

One of the advantages of the present invention is its potential to enhance mixing of systemic arterial blood, particularly in the aorta. Such enhanced mixing ensures the delivery of blood with higher oxygen-carrying capacity to organs supplied by arterial side branches off of the aorta. A method of enhancing mixing utilizing the present invention preferably includes taking steps to assess certain parameters of the patient and then to determine the minimum output of the pump that, when combined with the heart output, ensures turbulent flow in the aorta, thereby enhancing blood mixing.

Blood flow in the aortic arch during normal cardiac output may be characterized as turbulent in the end systolic phase. It is known that turbulence in a flow of fluid through pipes and vessels enhances the uniform distribution of particles within the fluid. It is believed that turbulence in the descending aorta enhances the homogeneity of blood cell distribution in the aorta. It is also known that laminar flow of viscous fluids leads to a higher concentration of particulate in the central portion of pipes and vessels through which the fluid flows. It is believed that, in low flow states such as that experienced during heart failure, there is reduced or inadequate mixing of blood cells leading to a lower concentration of nutrients at the branches of the aorta to peripheral organs and tissues. As a result, the blood flowing into branch arteries off of the aorta will likely have a lower hematocrit, especially that flowing into the renal arteries, the celiac trunk, the spinal arteries, and the superior and inferior mesenteric arteries. That is because these branches draw from the periphery of the aorta The net effect of this phenomenon is that the blood flowing into these branch arteries has a lower oxygen-carrying capacity, because oxygen-carrying capacity is directly proportional to both hematocrit and the fractional $O_2$ saturation of hemoglobin. Under those circumstances, it is very possible that these organs will experience ischemia-related pathology.

The phenomenon of blood streaming in the aorta, and the resultant inadequate mixing of blood resulting in central lumenal concentration of blood cells, is believed to occur when the Reynolds number ($N_R$) for the blood flow in the aorta is below 2300. To help ensure that adequate mixing of blood will occur in the aorta to prevent blood cells from concentrating in the center of the lumen, a method of applying the present invention to a patient may also include steps to adjust the output of the pump to attain turbulent flow within the descending aorta upstream of the organ branches; i.e., flow exhibiting a peak Reynolds number of at least 2300 within a complete cycle of systole and diastole. Because flow through a patient is pulsatile in nature, and not continuous, consideration must be given to how frequently the blood flow through the aorta has reached a certain desired velocity and, thus, a desired Reynolds number. The method contemplated herein, therefore, should also include the step of calculating the average Womersley number ($N_W$), which is a function of the frequency of the patient's heart beat. It is desired that a peak Reynolds number of at least 2300 is attained when the corresponding Womersley number for the same blood flow is approximately 6 or above.

More specifically, the method may comprise calculating the Reynolds number for the blood flow in the descending aorta by determining the blood vessel diameter and both the velocity and viscosity of the fluid flowing through the aorta. The Reynolds number may be calculated pursuant to the following equation:

$$N_R = \frac{V \cdot d}{\upsilon}$$

where: V=the velocity of the fluid; d=the diameter of the vessel; and $\upsilon$=the viscosity of the fluid. The velocity of the blood flowing through the aorta is a function of the cross-sectional area of the aorta and the volume of flow therethrough, the latter of which is contributed both by the patient's own cardiac output and by the output of the pump of the present invention. Velocity may be calculated by the following equation:

$$V = \frac{Q}{\pi r^2}$$

where Q=the volume of blood flowing through the blood vessel per unit time, e.g., the aorta, and r=radius of the aorta. If the relationship between the pump output and the velocity is already known or independently determinable, the volume of blood flow Q may consist only of the patient's cardiac output, with the knowledge that that output will be supplemented by the subcardiac pump that is part of the present invention. If desired, however, the present system can be implemented and applied to the patient first, before calculating Q, which would consist of the combination of cardiac output and the pump output.

The Womersley number may be calculated as follows:

$$N_W = r\sqrt{\frac{2\pi\omega}{\upsilon}}$$

where r is the radius of the vessel being assessed, ω is the frequency of the patient's heartbeat, and $\upsilon$=the viscosity of the fluid. For a peak Reynolds number of at least 2300, a Womersley number of at least 6 is preferred, although a value as low as 5 would be acceptable.

By determining (i) the viscosity of the patient's blood, which is normally about 3.0 mm$^2$/sec (kinematic viscosity), (ii) the cardiac output of the patient, which of course varies depending upon the level of CHF and activity, and (iii) the diameter of the patient's descending aorta, which varies from patient to patient but is about 21 mm for an average adult, one can determine the flow rate Q that would result in a velocity through the aorta necessary to attain a Reynolds number of at least 2300 at its peak during the patient's heart cycle. Based upon that determination of Q, one may adjust the output of the pump of the present invention to attain the desired turbulent flow characteristic through the aorta, enhancing mixing of the blood therethrough.

One may use ultrasound (e.g., echocardiography or abdominal ultrasound) to measure the diameter of the aorta, which is relatively uniform in diameter from its root to the abdominal portion of the descending aorta. Furthermore, one may measure cardiac output using a thermodilution catheter or other techniques known to those of skill in the art. Finally, one may measure viscosity of the patient's blood by using known methods; for example, using a capillary viscosimeter. It is expected that in many cases, the application of this embodiment of the present method will provide a basis to more finely tune the system to more optimally operate the system to the patient's benefit. Other methods contemplated by the present invention may include steps to assess other patient parameters that enable a person of ordinary skill in the art to optimize the present system to ensure adequate mixing within the vascular system of the patient.

Alternative inventive methods that provide the benefits discussed herein include the steps of, prior to applying a shape change therapy, applying a blood supplementation system (such as one of the many examples described herein) to a patient, whereby the methods are designed to improve the ability to reduce the size and/or wall stress of the left ventricle, or both ventricles, thus reducing ventricular loading. Specifically, one example of such a method comprises the steps of providing a pump configured to pump blood at subcardiac rates, providing inflow and outflow conduits configured to fluidly communicate with non-primary blood vessels, fluidly coupling the inflow conduit to a non-primary blood vessel, fluidly coupling the outflow conduit to the same or different (primary or non-primary) blood vessel and operating the subcardiac pump in a manner, as described herein, to reduce the load on the heart, wherein the fluidly coupling steps may comprise anastomosis, percutaneous cannulazation, positioning the distal end of one or both conduits within the desired terminal blood vessel or any combination thereof. The method further comprises, after sufficient reduction in ventricular loading, applying a shape change therapy in the form of, for example, a cardiac reshaping device, such as those referred to herein, or others serving the same or similar function, for the purpose of further reducing the size of and/or wall stress on one or more ventricles and, thus, the heart, and/or for the purpose of maintaining the patient's heart at a size sufficient to enhance recovery of the patient's heart.

II. Cannulae for Use in Extracardiac Heart Assist Systems

As discussed above, application of a heart assist system to a patient can involve inserting a cannula into the patient's vasculature to deliver and/or withdraw blood. Such cannulae may be single lumen, as shown in FIGS. 1-9 and 12-13, or multilumen, as shown in FIGS. 10-11. Some of the cannulae discussed hereinbelow are described as having a single lumen and others are described has having multiple (e.g., two) lumens. The features of the single lumen embodiments may be combined with the features of the multiple lumen embodiments described herein. Similarly, the features of the multiple lumen embodiments may be combined with the features of the single lumen embodiments. In particular, the tip designs discussed hereinbelow can be coupled with a single lumen cannula or a multiple lumen cannula.

In application, the cannulae may be positioned within vessels that vary in size, but which are often relatively small. As such, the cannulae may interact with the vessels in addition to withdrawing and/or delivering blood therefrom. Such interaction can be deleterious. For example, if the cannula resides in the vessel so that blood flows out of the cannula against a wall of the vessel, plaque or other particles associated with the wall may break free. One skilled in the art will appreciate that such a result could be harmful to the patient. Various embodiments of cannulae that are configured to minimize deleterious interactions between the cannulae and the vasculature, e.g., by controlling the manner in which the blood passes between a lumen of the cannula and the vessel in which the cannula resides, are discussed below.

Figure 17A:
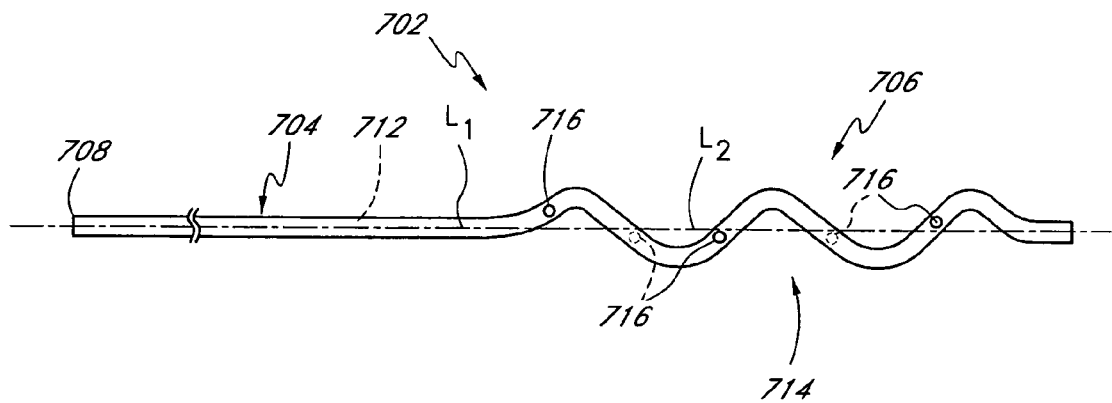
FIG. 17A is a schematic view of one embodiment of a cannula having a redirecting tip in a configuration for insertion into a patient.
Figure 17B:
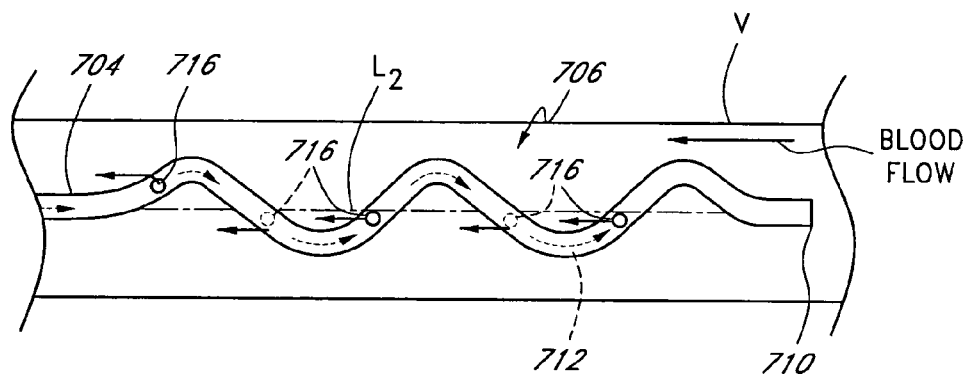
FIG. 17B is a schematic view of the cannula of FIG. 17A showing the cannula deployed in the patient's vasculature.
Figure 17C:
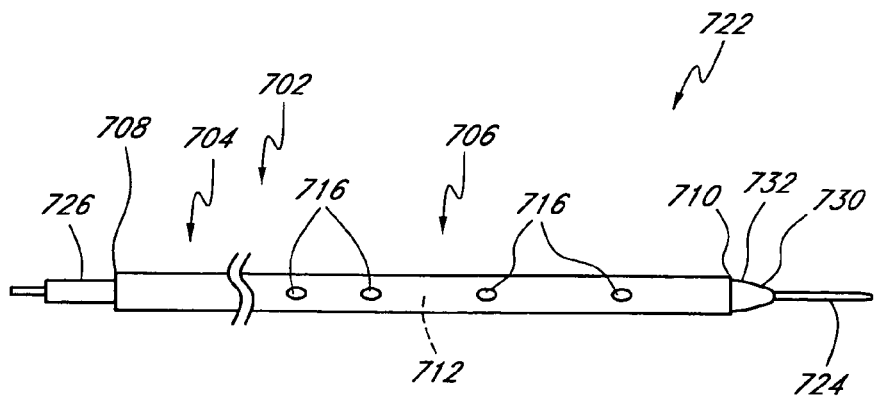
FIG. 17C is a schematic view of one embodiment of a system for deploying the cannula of FIG. 17A.

With reference to FIGS. 17A-17C, one embodiment of a percutaneous cannula 702 that can be used in an advantageous manner to direct blood into a vessel of a patient will be discussed. The cannula 702 includes a main cannula portion 704 at a proximal portion of the cannula 702 and a transition portion 706 at a distal portion of the cannula 702. The cannula 702 is defined by a proximal end 708, a distal end 710, and a blood-flow lumen 712 extending substantially entirely therethrough. If desired, the transition portion 706 may be a discrete component connected in a suitable fashion to the main cannula portion 704. The transition portion 706 is configured to re-direct blood-flow in a manner discussed below.

The main cannula portion 704 is generally cylindrical, extending along a longitudinal axis $L_1$ from the proximal end 708 toward the transition portion 706. If desired, the cannula 702 could be configured to have a plurality of lumens therethrough that can be employed to considerable advantage in connection with heart assist systems adapted for single-site application. For example, the transition portion 706 could be combined with a multilumen cannula, such as the multilumen cannulae shown in FIGS. 10-11.

The transition portion 706 preferably has a generally curvilinear configuration and, more preferably, a helical or spiral-shaped portion. The generally helically-shape portion is formed in the transition portion 706 by extending the transition portion 706 (and thus the distal portion of the lumen 712) radially outward from the longitudinal axis $L_1$ of the main cannula portion 704 and forming a series of coils 714 that are arranged about a helical central axis $L_2$, whereby the coils may be radially concentric and of similar diameter. The pitch of each of the coils 714 (e.g., the distance between corresponding points on adjacent coils 714) is preferably about the same, as shown in the embodiment of FIGS. 17A-17C. Importantly, it is contemplated that the helical shape is sufficiently deformable to comprise a low-profile configuration during delivery and a fully expanded configuration after deployment. Thus, the helical shaped portion may be said to be collapsible.

Preferably, the cannula 702 further comprises a plurality of apertures 716 formed in a sidewall thereof, either on the transition portion 706, on the main cannula portion 704, or on both. The apertures 716 formed in the cannula 702 facilitate blood flow between the lumen 712 and the patient's vasculature. Where the percutaneous cannula 702 is applied as an outflow cannula, the apertures 716 function as outflow apertures, which direct blood from the lumen 712 into a blood vessel, as shown in the embodiment of FIG. 17B. Where the percutaneous cannula 702 is applied as an inflow cannula, the apertures 716 function as inflow apertures, which direct blood from a blood vessel into the lumen 712. As discussed above, the cannula 702 may be configured as a multilumen cannula, and thus the cannula 702 may function as both and inflow and an outflow cannula in some applications.

Many variations on the configuration of transition portion 706 are contemplated. For example, in one embodiment, the diameter of adjacent coils 714 is progressively smaller toward the distal end. This embodiment may be advantageous where the size of a vessel in which the transition portion 706 is expected to reside when deployed tapers to progressively smaller diameters. In another embodiment, the diameter of adjacent coils 714 is progressively larger toward the distal end for use in a portion of the vasculature that tapers to progressively larger diameters.

As with the diameter of the coils 714, the pitch of the coils 714 may vary depending upon the concentration of apertures within a given area desired. For example, in one embodiment, the coils 714 are closer to each other (e.g., the pitch is smaller) near the proximal end of the transition portion 706 than are the coils 714 near the distal end of the transition portion 706. As with the diameter of the coils 714, the pitch of the coils 716 could be smaller (or larger) near the center of the transition portion 706 than is the pitch near both the proximal end and the distal end of the transition portion 706.

In various embodiments, the apertures 716 are located and oriented such that when the transition portion 706 is in the expanded configuration, the apertures 716 are at a selected orientation with respect to the helical central axis $L_2$. For example, in one embodiment the apertures 716 are located on the inside of the coils 714 (i.e., generally facing the axis $L_2$) and are oriented parallel to the axis $L_2$. This embodiment advantageously provides a flow of blood out of an aperture 716 directly away from the vessel wall that is nearest to the aperture 716 when the cannula 702 is applied to the patient. This flow arrangement lessens the likelihood that the flow will disrupt any plaque or other matter at the vessel wall.

In another embodiment, the apertures 716 are located on the inside of the coils 714 and are oriented such that when the transition portion 706 is in the expanded configuration, the apertures 716 form an angle with respect to the axis $L_2$. For example, in the embodiment illustrated by FIG. 17B, when the cannula 702 is applied in a vessel V as an outflow cannula, the blood-flow exits the lumen 712 in the transition portion 706 through the apertures 716 toward the axis $L_2$ and generally proximally toward the main cannula portion 704. In this arrangement, blood-flow out of the cannula 702 through the apertures 716 may be described as generally counter to the flow of blood in the lumen 712.

In the application of the embodiment illustrated in FIG. 17B, the blood passing through the apertures 716 enters the vessel V in generally the same direction as the flow of blood in the vessel V. This reduces what might otherwise be a disruption of the flow of blood in the vessel V. The cannula 702 thus facilitates reintroduction of blood into the bloodstream in a manner that advantageously supplements circulation.

In another embodiment the apertures 716 are located on the inside of the coils 714 and are oriented such that when the transition portion 706 is in the expanded configuration, the apertures 716 are oriented generally toward the distal end 710. This embodiment advantageously provides a flow of blood generally along a line oriented toward the central axis $L_2$ and toward the distal end 710 of the cannula 702 when the cannula 702 is applied as an outflow cannula. If applied as an outflow cannula, this embodiment will also advantageously provide blood-flow through the apertures 716 away from the nearest vessel wall and against the flow of blood in the vessel. In another embodiment, the apertures 716 are located and oriented such that when the transition portion 706 is in the spiral shape, the apertures 716 are oriented toward an opposing portion of the adjacent coils 714.

The transition portion 706 of the percutaneous cannula 702 preferably is capable of having a low profile configuration for delivery and an expanded operating profile. In one embodiment, a shape memory material is used for the transition portion 706 that is flexible enough to enable the transition portion 706 to be substantially straightened for delivery so that the profile of the main cannula portion 704 and the transition portion 706 are approximately the same. When the cannula 702 is deployed in the vessel V and coupled with a heart assist system, the transition portion 706 is in a spiral shape (see FIG. 17B).

With reference to FIG. 17C, a percutaneous delivery system 722 whereby the percutaneous cannula 702 can be delivered in a minimally invasive manner will be discussed. The system 722 includes the percutaneous cannula 702, a guide-member 724, and a straightener 726. In some applications, the guide-member 724 and/or the straightener 726 are not required, as discussed more fully below. The guide-member 724 is a low profile structure that facilitates delivery of the cannula 702 to a selected location within the vasculature. In one embodiment, the guide-member 724 is a standard guidewire used in percutaneous procedures.

The straightener 726 is a stiff member that reduces the profile of the transition portion 706, as discussed above. In one embodiment, the straightener 726 is a stiff cylindrical rod with a lumen extending therethrough. The lumen in the straightener 726 is sized to receive the guide-member 724. In the illustrated embodiment, the outer diameter of the straightener 726 is sized to be received by the lumen 712 of the percutaneous cannula 702. The straightener 726 is stiffer than the percutaneous cannula 702. Accordingly, when the straightener 726 is positioned in the cannula 702, the transition portion 706 of the cannula 702 generally conforms to the shape of the straightener 726. When the transition portion 706 of the percutaneous cannula 702 generally conforms to the shape of the straightener 726, the transition portion 706 has a relatively low profile, which is advantageous for insertion into the vasculature, as discussed above. In another embodiment, the system 722 is provided without the guide-member 724. In various other embodiments, the straightener 726 and the other straighteners described herein may be an obturator or a dilator, various embodiments of which are disclosed in U.S. Pat. No. 6,488,662, issued Dec. 3, 2002, which is hereby incorporated by reference herein in its entirety.

The straightener 726, in addition to being configured to straighten the transition portion 706, may be configured to facilitates delivery of the cannula 702 to a selected location within the vasculature. For example, the straightener 726 may have a tapered tip portion 730 that extends beyond the distal end 710 of the cannula 702 when the straightener 726 is inserted into the cannula 702. A proximal end 732 of the tapered tip portion 730 and the distal end 710 of the cannula 702 can be configured to cooperate to facilitate percutaneous insertion. For example, the outer diameter of the proximal end 732 of the tapered tip portion 730 can be formed such that there is a relatively smooth transition from the tapered tip portion 730 to the cannula 702. In one embodiment, this is achieved by providing the proximal end 732 of the tapered tip portion 730 with approximately the same outer diameter as that of the cannula 702. This arrangement minimizes or eliminates the size of any exposed surface perpendicular to the axis $L_2$ of the distal end 710 of the cannula 702 that would contact the vessel wall when the system 722 is inserted into the vessel. The likelihood of the system 722 becoming hung-up on the vessel wall upon insertion is thereby reduced.

Figure 18A:
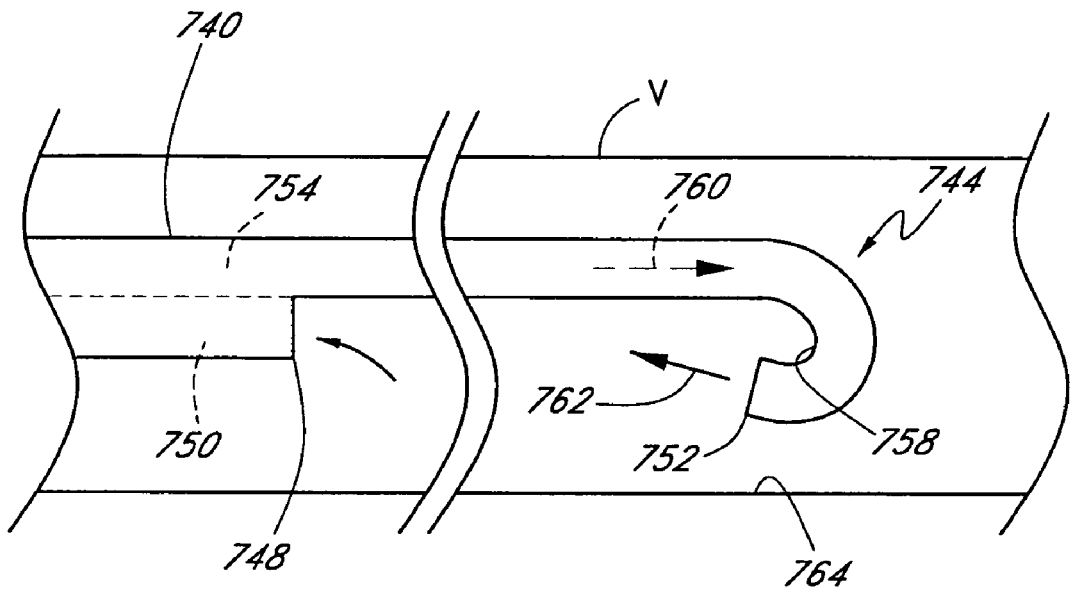
FIG. 18A is a schematic view of another embodiment of a cannula having a redirecting tip deployed in a patient's vasculature.
Figure 18B:
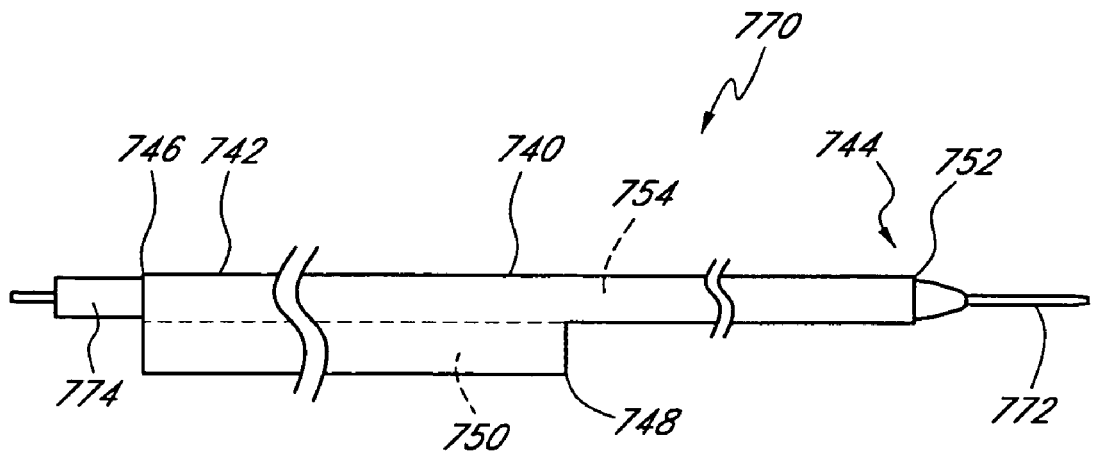
FIG. 18B is a schematic view of the cannula of FIG. 18A in a configuration for insertion into a patient.

With reference to FIGS. 18A-18B, another embodiment of a percutaneous cannula 740 for directing blood into a vessel of a patient will be discussed. The cannula 740 has a main cannula portion 742 at a proximal portion of the cannula 740 and a transition portion 744 at a distal portion of the cannula 740. The cannula 740 is defined by a proximal end 746, a first distal end 748, and a first lumen 750 that extends therebetween. The cannula 740 also is defined by a second distal end 752 and a second lumen 754 in one embodiment. The lumen 754 preferably extends between the proximal end 746 and the second distal end 752. The transition portion 744, like the transition portion 706, is configured to minimize harmful interaction between the blood flow exiting the lumen 754 and the vessel in which the cannula 740 is deployed. Although the cannula 740 is a multilumen cannula, the features thereof could advantageously be applied in a single lumen cannula, such as any of those described herein.

The transition portion 744 is shaped to have an arcuate portion near the second distal end 752. The arcuate portion is defined by a curve, e.g., a curved inner profile 758 subtending any suitable number of degrees. In one embodiment, the curved inner profile 758 subtends an angle of more than about 180 degrees. The arcuate portion can be formed with a non-circular shaped inner profile, e.g., parabolic, oval, etc. Other configurations are also possible, e.g., curvilinear and non-curvilinear configurations. Non-curvilinear configurations could be disadvantageous due to presence of hard edges and the effect thereof on the blood cells.

As discussed above, the cannula 740 is configured to prevent blood-flow exiting the second distal end 752 from immediately discharging against a wall of the vessel. In particular, the transition portion 744 can be configured to discharge blood through the discharge opening away from the adjacent blood vessel wall. Also, the cannula 740 illustrated by FIG. 18A has a width much less than that of the vessel, in some applications one or more lateral side of the cannula 740, e.g., the side near the second distal end 752, may rest against a vessel wall.

In one application, the cannula 740 is applied to the vasculature of a patient and is coupled with an extracardiac heart assist system, such as the system 450, to supplement the circulation of blood through a patient. In particular, the lumen 754 is coupled with a pump in a manner that provides blood-flow from the pump, through the lumen 754 and into the vasculature of the patient. A distal portion of the cannula 740 is positioned in the vasculature with the transition portion 744 in a vessel V. An arrow 760 illustrates the flow of blood within the lumen 754 toward the transition portion 744 of the cannula 740.

The direction of flow in the lumen 754 is altered in the transition portion 744 in a suitable manner. In one embodiment, the blood exiting the transition portion 744 is altered such that the flow is generally counter to the direction of flow in the lumen 754 upstream of the transition portion 744. An arrow 762 illustrates the flow exiting the transition portion 744. The direction of the arrow 762 is generally counter to the direction of the arrow 760. In addition, the blood flow exiting the lumen 754 is generally away from a wall 764 of the vessel V which is nearest to the transition portion 744. As with the cannula 702, the cannula 740 may be applied so that the blood flow exiting the lumen 754 also is generally in the same direction of the flow of blood in the vessel V.

With reference to FIG. 18B, a system 770 for deploying the cannula 740 may be provided. The system 770 is similar to the system 722. In particular, the system 770 includes the percutaneous cannula 740, a guide-member 772, and a straightener 774. As discussed above, in one form the guide-member 772 is a low profile structure, e.g., a guidewire, that facilitates delivery of the cannula 740. The straightener 774 is a stiff preferably cylindrical member that is configured to straighten the transition portion 744. The distal tip portion of the straightener 774 is tapered in some embodiments. As discussed above in connection with the system 722, the straightener 774 and the cannula 740 can be configured to cooperate to facilitate percutaneous insertion into a vessel (e.g., by providing a relatively smooth transition between the straightener 774 and the cannula 740 such to minimize or eliminate a step from the proximal end of the tapered portion to the outer surface of the cannula 740).

In one method of applying the cannula 740, the straightener 774 is inserted into the lumen 754 of the cannula 740 until the transition portion 744 is straightened, e.g., actuated to a low-profile configuration. The combination of the cannula 740 and the straightener 774 may be advanced into the vessel V in any suitable manner, e.g., over a guide wire and/or through a sheath. After the combination of the cannula 740 and the straightener 774 has been advanced to a desired location, the straightener 774 is withdrawn. In some applications where the size of the vessel V is small, partial withdrawal of the straightener 774 may permit the transition portion 744 to curl proximally until the distal end 752 contacts the wall 764 of the vessel V. In one preferred method, before the straightener 774 is withdrawn any further, the cannula 740 is advanced distally with respect to the straightener 774, which substantially maintains the distal end 752 of the cannula 740 stationary. As the proximal-most portion of the transition portion 744 moves distal of the distal end of the straightener 774, the transition portion 744 becomes fully deployed, e.g., the distal end 752 curls to the fully deployed configuration. As this occurs, the distal end 752 pivots at substantially a single point on the wall 764 of the vessel V rather than sliding along the wall 764. This method of deploying the transition portion 744 advantageously minimizes risks associated with deployment of the cannula 740, e.g., abrasion of the wall 764 and emboli generation by dislodgment of deposits on the wall 764.

Figure 19A:
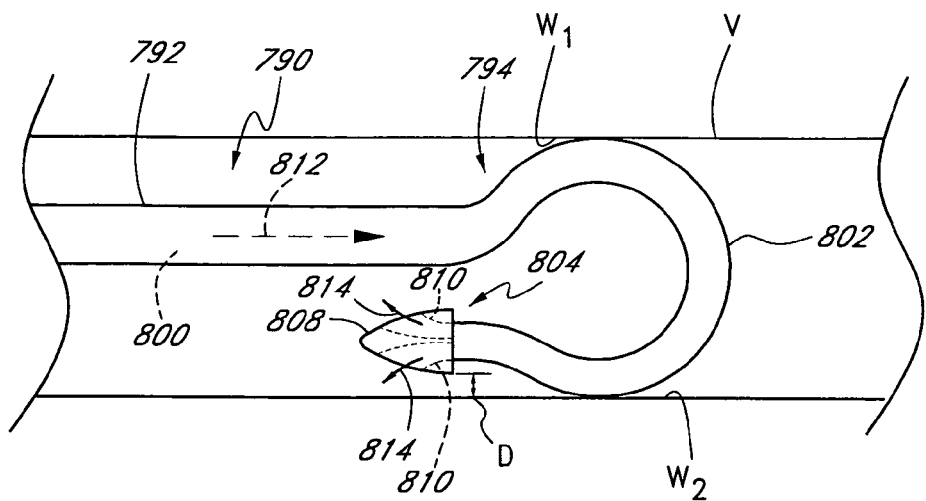
FIG. 19A is a schematic of another embodiment of a cannula having a redirecting tip deployed in a patient's vasculature.
Figure 19B:
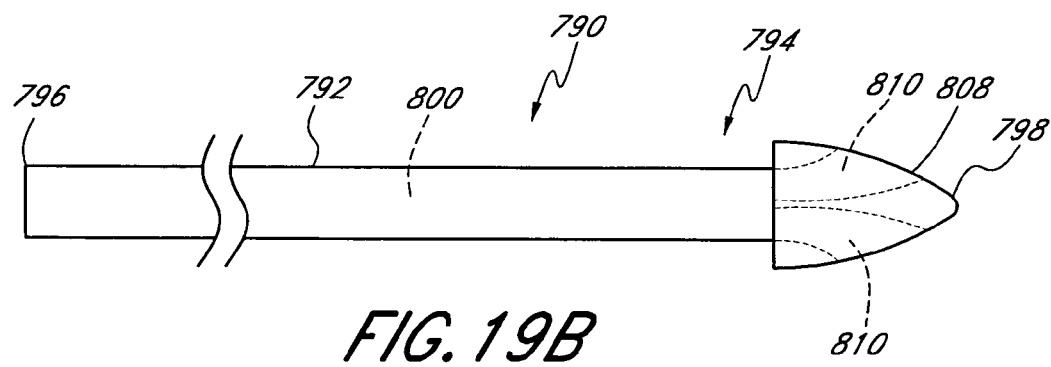
FIG. 19B is a schematic view of the cannula of FIG. 19A in a configuration for insertion into a patient.

Another embodiment of a cannula 790 has a main cannula portion 792 at a proximal portion of the cannula 790 and a transition portion 794 at a distal portion of the cannula 790, as shown in FIGS. 19A-19B. The cannula 790 is defined by a proximal end 796, a distal end 798, and a lumen 800 that extends therebetween. The cannula 790 is configured to be employed in a heart assist system similar to those discussed above. Accordingly, the proximal end 796 is configured to be directly or indirectly coupled with a pump. The distal end 798 is in fluid communication with the proximal end 796 and is configured to deliver blood to a vessel when the cannula 790 is applied as an outflow cannula. The transition portion 794 is configured to minimize harmful interaction between the blood flow exiting the lumen 800 and the vessel in which the cannula 790 is deployed.

The main cannula portion 792 is capable of having a first configuration for insertion and advancement into a patient's vasculature (e.g., as shown in FIG. 19B) and a second configuration for operation in connection with a heart assist system defined herein (e.g., as shown in FIG. 19A). The first and second configurations can be achieved by inserting a guide-member and a straightener, as discussed in connection with FIGS. 17A-18B, by a straightener alone, or by any other suitable percutaneous insertion technique.

The cannula 790 is configured to prevent blood-flow exiting the distal end 798 from immediately discharging against a wall of the vessel V adjacent the transition portion 794. The transition portion 794 includes a curvilinear portion 802 and an outflow portion 804. When the cannula 790 is deployed (e.g., in the vessel V and in the second configuration), the curvilinear portion 802 resides distally of the outflow portion 804. In one embodiment, the outflow portion 804 is positioned at about the same location as the proximal-most portion of the curvilinear portion 802. The outflow portion 804 could also be shorter, such that it resides on the curvilinear portion 802. For example, the outflow portion 804 could be located mid-stream in the vessel V, pointing toward a wall of the vessel V when in the second configuration within the vessel V.

In one embodiment, the curvilinear portion 802 includes an arcuate portion that defines an arc subtending more than about 180 degrees or more than 180 degrees. The curvilinear portion 802 of the cannula 790 extends outwardly from the main cannula portion 792 to a first location proximate a first wall $W_1$ of the vessel V. The curvilinear portion 802 further curves from the first wall $W_1$ to a second location proximate a second wall $W_2$ of the vessel V. The curvilinear portion 802 further curves from the second wall $W_2$ inward toward the central region of the vessel V, wherein the main cannula portion 792 resides. This arrangement positions the outflow portion 804 of the transition portion 794 a distance D from the second wall $W_2$. In some embodiments, the outflow portion 804 is oriented by the curvilinear portion 802 such that it is parallel the main cannula portion 792. By spacing the outflow portion 804 from the wall $W_2$ of the vessel V, the blood exiting the lumen 800 of the cannula 790 is prevented from directly impacting the wall $W_2$. This reduces the likelihood that the blood exiting the lumen 800 will harm the vessel V or create any embolic material within the vasculature.

In one embodiment, the transition portion 794 is further configured to reduce the likelihood of damage to the vessel V or to the vasculature. In particular, in some embodiments the outflow portion 804 includes a means for diffusing blood-flow out of the cannula 790. In one embodiment, the means for diffusing comprises a tip 808 that has a generally larger cross-sectional area than the curvilinear portion 802 proximate the proximal end of the tip 808. Preferably a plurality of channels 810 are formed in the tip 808. The channels 810 are configured to separate the blood flowing within the lumen 800, indicated by the arrow 812, into at least two streams, indicated by the arrows 814. The channels 810 preferably are also configured to reduce the velocity of the blood as it moves from one end of the channel 810 to the other end of the channel 810, where it exits the cannula 790. In one embodiment, such velocity reduction is accomplished by increasing the cross-sectional area of each of the channels between first ends of the channels 810 adjoining the lumen 800 and second ends of the channels 810 opening up to the vessel V.

As discussed in connection with the cannula 702, the cannula 790 may be configured as a single or a mutilumen cannula. The cannula 790 could be configured to have a plurality of lumens to facilitate single-site application. In one embodiment, the transition portion 794 is combined with a multilumen cannula similar to that shown in FIGS. 10-11.

Figure 20:
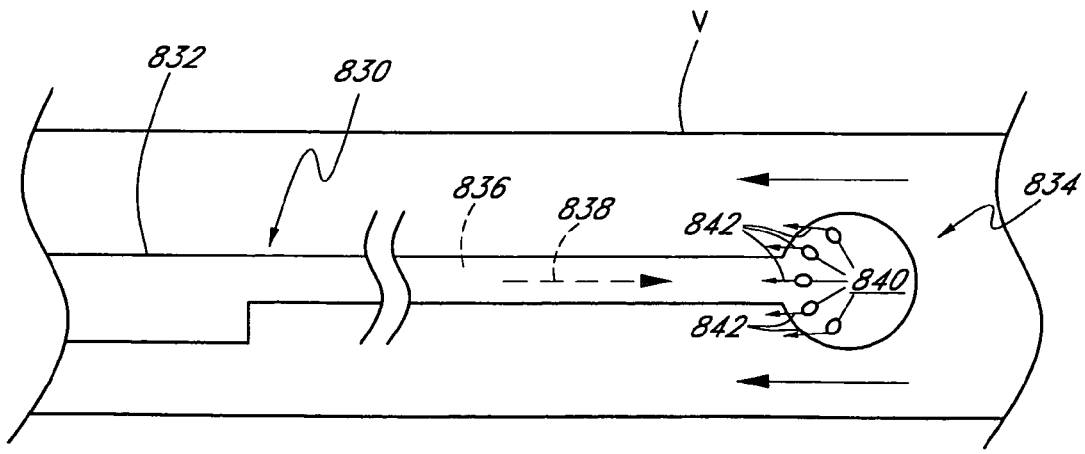
FIG. 20 is a schematic view of another embodiment of a cannula having a redirecting tip deployed in a patient's vasculature.

With reference to FIG. 20, another embodiment of a cannula 830 can be deployed in a vessel V. The cannula 830 has a main cannula portion 832 and a tip portion 834 for redirecting flow in the cannula 830. The cannula 830 has a lumen 836 extending therethrough. The main cannula portion 832 is similar to the main cannula portion 742 of the cannula 740. In particular, the main cannula portion 832 has a second lumen extending therethrough which is shorter than the lumen 836. The cannula 830 also may be configured as a single lumen cannula, as discussed above in connection with the cannula 740. The lumen 836 is configured to convey blood into a vessel in one application and out of a vessel in another application. In some embodiments and in some applications, the cannula 830 is configured to convey blood between two or more vessels. In other embodiments and applications, the cannula 830 is configured to convey blood from one area of a vessel to another area of the vessel. An arrow 838 illustrates the blood-flow within the lumen 836, where the cannula 830 is applied as an outflow cannula.

In one embodiment, the tip portion 834 includes a plurality of apertures 840 to direct blood flow between the lumen 836 and the vessel V in an advantageous manner, e.g., to minimize or eliminate any potentially harmful interactions between the cannula 830 and the vessel V. The cross-sectional size of the tip portion 834 is larger than that of the main cannula portion 832. In the illustrated embodiment, the tip portion 834 is generally spherical in shape, though other shapes are possible. The tip portion 834 has a radius greater than the radius of the cross-section of the main cannula portion 832. Where the tip portion 834 is in this manner larger than the main cannula portion 832, the apertures 840 can be positioned radially outside the cross-sectional profile of the main cannula portion 832. In addition, the cannula 830 preferably orients the apertures 840 in a suitable manner to redirect blood-flow. In one embodiment, where the cannula 830 is applied as an outflow cannula, the apertures 840 are oriented to direct flow out of the lumen 836 into the vessel V generally counter-flow, e.g., in a direction other than the direction of flow in the lumen 836. The flow in such application is represented by a corresponding plurality of arrows 842 emerging from the apertures 840 (see FIG. 20). As can be seen, the arrows 842 are oriented in a direction generally opposite that of the arrow 838. Thus, the cannula 830 redirects the flow of blood from the lumen 836 to the vessel V. As discussed above, the cannula 830 redirects the blood-flow exiting the distal end of the cannula 830, preventing it from immediately discharging against a wall of the vessel V. The likelihood of harmful interactions between the blood-flow and the vessel V or the vasculature in general is thereby reduced.

Figure 21A:
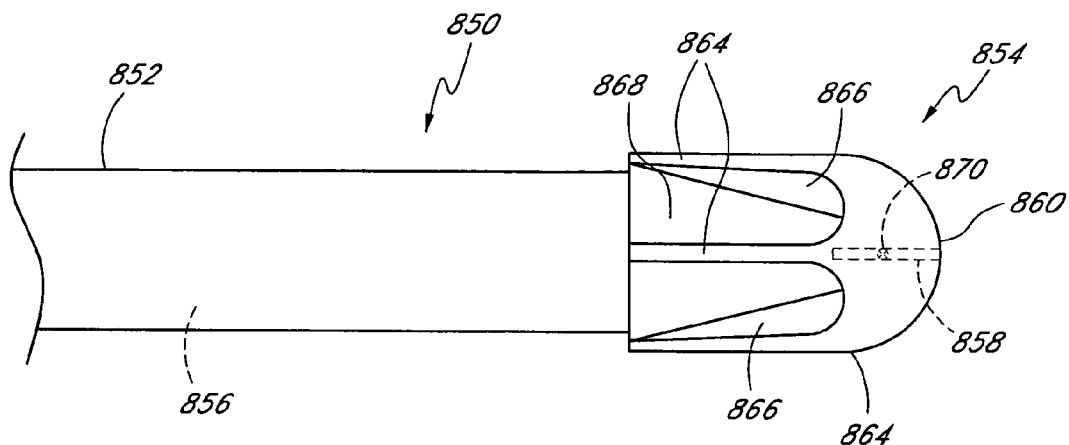
FIG. 21A is a schematic view of another embodiment of a cannula having a redirecting tip.
Figure 21B:
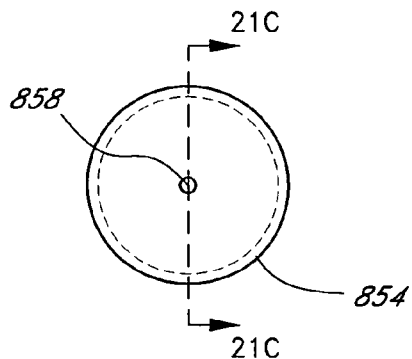
FIG. 21B is a schematic end view of the cannula of FIG. 21A.
Figure 21C:
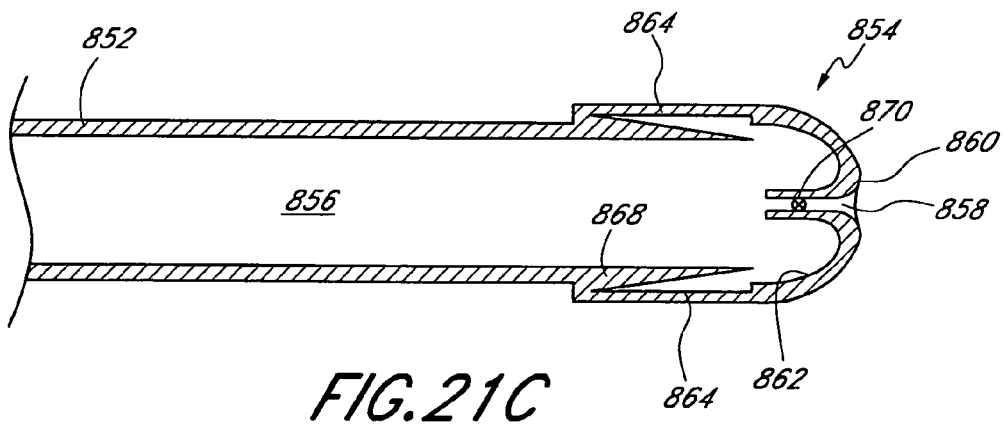
FIG. 21C is a cross-sectional view of the cannula of FIG. 21A taken along the section plane shown in FIG. 21B.

With reference to FIGS. 21A-21C, another embodiment of a cannula 850 is provided that has a main cannula portion 852 and a tip portion 854 for redirecting blood-flow. The cannula 850 also has a blood-flow lumen 856 and a guide-member lumen 858. The guide-member lumen 858 is configured to receive a guidewire or other suitable guide-member. As is known, such a guide-member can facilitate delivery of the cannula 850 to a selected location within the vasculature. Like many of the cannulae described above, the cannula 850 includes a proximal end (not shown) and a distal end 860 between which the blood-flow lumen 856 extends.

The cannula 850 is arranged to direct blood-flow between a vessel and the lumen 856. As with the cannulae described above, the cannula 850 can be applied to a patient to direct blood into a vessel of a patient or to draw blood from the vessel into the lumen 856. The cannula 850 can also be applied to convey blood from one portion of a vessel, into the lumen 856, and out of the lumen 856 into another part of a vessel. As with the other cannulae described herein, the cannula 850 can be configured as either a single or as a multilumen cannula.

The tip portion 854 includes a curved surface 862 positioned distal of the blood-flow lumen 856. The surface 862 is located and configured such that when the cannula 850 is applied as an outflow cannula, the surface 862 at least partially intercepts the blood-flow in the blood-flow lumen 856 and redirects the blood-flow, e.g., directs the blood-flow in a direction generally opposite that of the flow in the blood-flow lumen 856. In the illustrated embodiment, the curved surface 862 is connected to the main cannula portion 852 by a plurality of struts 864 which extend proximally of the curved surface 862. The struts 864 form therebetween a series of blood-flow windows 866. In one embodiment, the windows 866 are lateral openings in the cannula 850 which direct blood out of the cannula 850 and into a vessel, where the cannula 850 is applied as an outflow cannula. Thus, the windows 866 can operate as discharge openings. If the cannula 850 is applied as an inflow cannula, blood is drawn through the windows 866 from the vessel into the blood-flow lumen 856 of the cannula 850.

The tip portion 854 also includes a funnel portion 868 that extends proximally from the distal end of the blood flow lumen 856. The funnel portion 868 directs substantially all of the blood that is flowing in the lumen 856 toward the surface 862 of the tip portion 854, which redirects the blood-flow as discussed above.

The cannula 850 redirects blood-flow to prevent the blood-flow exiting the distal end 860 from immediately discharging against a wall of the vessel. Thus the cannula 850 reduces the likelihood that the blood-flow will have an adverse effect on the vessel in which the cannula 850 resides or on the vasculature in general.

In some embodiments, the cannula 850 is provided with means for sealing the guide-member lumen 858. The sealing means can be any suitable structure. One embodiment provides a mechanical valve 870. Other sealing means include non-mechanical valves, plugs, etc. One form of plug that would be suitable is one that expands in the presence of blood, e.g. a hydrogel. The sealing means permits the guide-member lumen 858 to receive a guide-member but substantially blocks the guide-member lumen 858 after the cannula 850 is delivered into a vessel and the guide-member is removed. By substantially blocking the guide-member lumen 858, the sealing means prevent blood-flow in the blood-flow lumen 856 from exiting the cannula 850 through the guide-member lumen 858, thereby maximizing the blood-flow through the windows 866.

Another embodiment of a cannula 880 having a main cannula portion 882 and a tip portion 884 will be discussed in connection with FIGS. 22A-22E. The cannula 880 also defines a lumen 886 extending therethrough. As with the cannulae described above, the cannula 880 could be advantageously configured as a single-lumen or as a multilumen cannula. In one embodiment, the main cannula portion 882 and the tip portion 884 are not discrete components. The main cannula portion 882 could be made a discrete component from the tip portion 884 to allow different tips to be applied depending upon the vessel into which the cannula 880 is to be inserted.

Figure 22A:
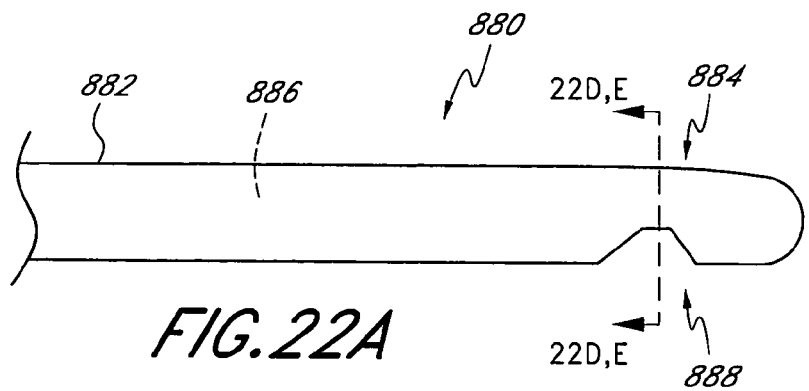
FIG. 22A is a schematic view of another embodiment of a cannula having a redirecting tip.
Figure 22B:
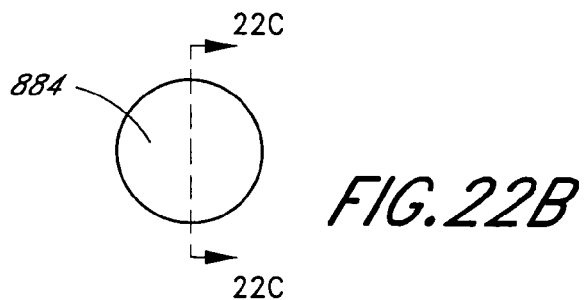
FIG. 22B is a schematic end view of the cannula of FIG. 22A.
Figure 22C:
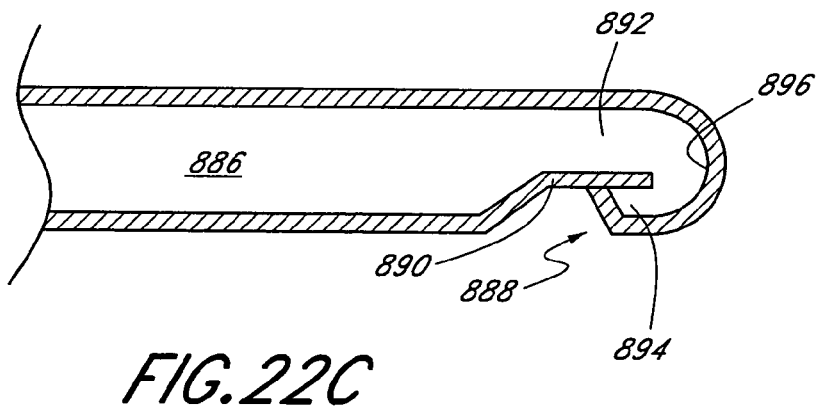
FIG. 22C is a cross-sectional view of the cannula of FIG. 22A taken along the section plane shown in FIG. 22B.
Figure 22D:
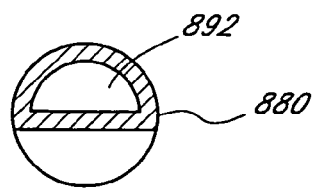
FIG. 22D is a cross-sectional view of one variation of the cannula of FIG. 22A taken along the section plane shown in FIG. 22A.
Figure 22E:
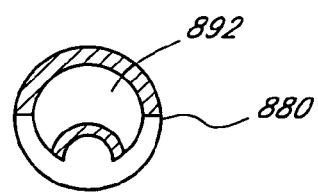
FIG. 22E is a cross-sectional view of one variation of the cannula of FIG. 22A taken along the section plane shown in FIG. 22A.

Referring to FIG. 22C, the tip portion 884 comprises a lateral opening 888 formed on the side thereof. The lateral opening 888 allows the lumen 886 to communicate with the vessel in which the cannula 880 is applied and acts as a discharge opening in some applications. The tip portion 884 provides a structure that substantially redirects the flow of blood in the lumen 886 as it passes between the lumen 886 and a vessel in which the cannula 880 is applied. In one embodiment, the lateral opening 888 is formed by forming a wall portion 890 of the tip portion 884 inwardly into the lumen 886. In the illustrated embodiment, the wall portion 890 is formed inwardly at the proximal end of the lateral opening 888. In the illustrated embodiment, the wall portion 890 extends about to the center of the lumen 886. In some embodiments, the wall portion 890 could be located closer to one side or the other of the lumen 886. In one embodiment, the wall portion 890 defines a constricted passage 892 and a flow-redirecting passage 894. In one embodiment, the wall portion 890 is formed such that the passage 892 has a semi-circular cross-section, as shown in FIG. 22D. In another embodiment, the wall portion 890 is formed such that the passage 892 has a crescent shaped cross section, as shown in FIG. 22E. In one embodiment, the wall portion 890 comprises a diverter wall, e.g., one that diverts blood in a suitable manner. The tip portion 884 of the cannula 880 further comprises a redirecting surface 896 in some embodiments. In one embodiment, the redirecting surface 896 is a spherical surface located distally of the constricted passage 892. The redirecting surface 896 could be a parabolic surface or any other suitable curved surface.

In one application, the lumen 880 is applied as an outflow cannula. Blood is directed into the proximal end (not shown) of the lumen 886. When the blood reaches the wall portion 890 of the redirecting tip portion 884, the blood is directed into the constricted passage 892 and up against the redirecting surface 896. The blood flowing against the redirecting surface 896 follows the curvature of the redirecting surface 896 from constricted passage 892 to the flow-redirection passage 894. The blood then may flow out of, e.g., be discharged from, the flow-redirection passage 894 into the blood vessel through the lateral opening 888.

Some advantages of the cannula 880 are apparent from FIGS. 22A-22B. For example, the redirecting tip portion 884 can be seen to have a low-profile configuration. As discussed above, a low profile configuration is advantageous for percutaneous insertion into the vasculature. The cannula 880 provides the further advantage of being relatively simple in construction wherein the portions of the redirecting tip portion 884 need not change shape upon application to a vessel. The cannula 880 also is not required to have different configurations for percutaneous insertion and for operation. For example, the cannula 880 is configured to have the same transverse size at its distal section during percutaneous insertion and during operation.

Like the cannulae discussed above, the cannula 880 can be provided with a single or with multiple lumens, as desired.

Figure 23A:
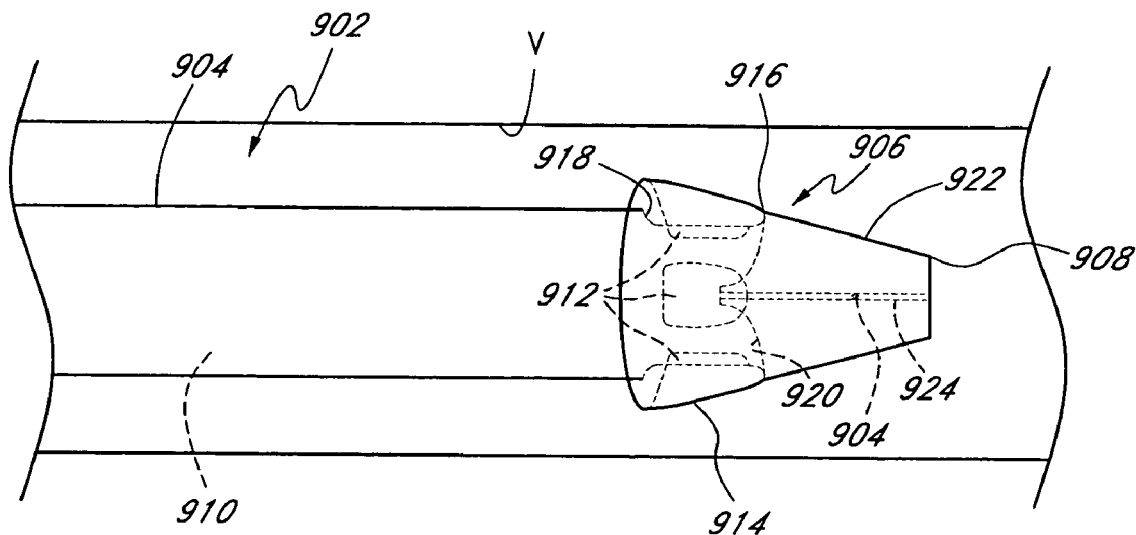
FIG. 23A is a schematic view of another embodiment of a cannula having a redirecting tip deployed in a patient's vasculature.
Figure 23B:
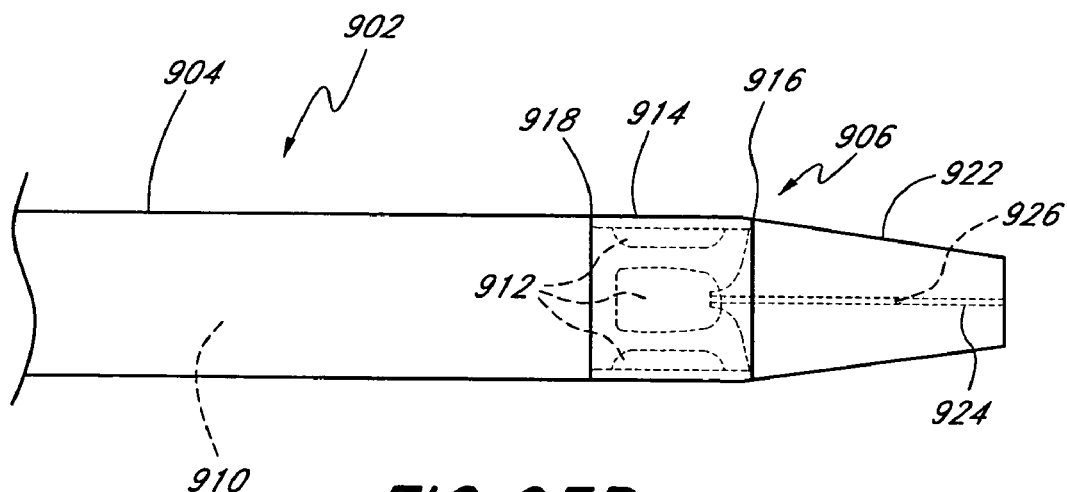
FIG. 23B is a schematic view of the cannula of FIG. 23A in a configuration for insertion into a patient.

Another embodiment of a percutaneous cannula 902 for directing blood into a vessel of a patient will be discussed in connection with FIGS. 23A-23B. The cannula 902 initially may be applied to a vessel V in a reduced profile configuration, wherein the cannula 902 can be more easily inserted percutaneously into the patient's vasculature, as shown in FIG. 23B. Although discussed primarily in terms of directing blood into a vessel, the cannula 902 can be applied in some applications to withdraw blood. The cannula 902 is defined by a proximal end (not shown), a main cannula portion 904, a tip portion 906, a distal end 908, and a lumen 910 extending between the proximal end and the distal end 908. The main cannula portion 904 extends distally from the proximal end of the cannula 902. The lumen 910 extends through the main cannula portion 906 and conveys blood in one application. The main cannula portion 904, like the main cannula portions of the other cannulae described herein, may be made of any suitable material, such as nylon, a nylon derivative, or PEBAX, e.g., PEBAX 65D. The cannula 902 may be configured as a single or a multiple lumen cannula, as discussed above. The tip portion 906, like the tip portions of the other cannulae described herein, may be made of a similar material or any other suitable material.

The tip portion 906 is configured to direct blood-flow in a direction generally opposite of the direction of flow through the lumen 910. In one embodiment, the average direction of blood flow out of the tip portion 906 is along a line that forms about a one-hundred sixty-five degree angle with respect to the longitudinal axis (not shown) of the lumen 910. In one embodiment, the tip portion 906 has a plurality of lateral openings 912 located near the distal end 908 and a redirecting member 914. The lateral openings 912 may be uniformly spaced radially around the cannula 902. In one embodiment, the lateral openings 912 comprise discharge openings. In another embodiment, the tip portion 906 could be formed with a single lateral opening 912, which may comprise a discharge opening. The redirecting member 914 preferably has a distal end 916 that is joined with the tip portion 906 such that a seal is formed between the redirecting member distal end 916 and the tip portion 906. The seal between the redirecting member distal end 916 and the tip portion 906 substantially prevents blood flow between the distal end 916 and the portion of the tip portion 906 that is distal of the redirecting member 914.

The redirecting member 914 can have any suitable arrangement, but the member 914 preferably is arranged to expand to uncover the openings 912 under the pressure in the lumen 910 of the cannula 902. In one embodiment, the redirecting member 914 has a range of degrees of expansion, similar to the range of degrees of expansion of a balloon. In another embodiment, the redirecting member 914 is actuatable between discrete configurations, e.g., between a collapsed configuration and an expanded configuration, in a manner similar to an umbrella. The pressure in the lumen 910 may be generated by any suitable pump coupled with the cannula 902. The pressure causes the member 914 to expand whereby blood flow is directed through the discharge opening 912. The redirecting member 914 also is collapsible to cover the discharge openings 912 during insertion of the cannula 902.

The redirecting member 914 preferably is made of a silicone material that can be dip-molded. In one embodiment, the silicone material is a low hardness silicone, e.g., a silicone with a durometer measurement of about 15 A, or less. The wall thickness of the redirecting member 914 preferably is between about 0.06 mm (0.0025 inches) and about 0.13 mm (0.005 inches). A thicker redirecting member 914, e.g., one with a thickness of about 0.13 mm (0.005 inches) might be preferable where the tip portion 906 of the cannula 902 is to be deployed in a higher pressure blood vessel. A thinner redirecting member 914, e.g., one with a thickness of about 0.06 mm (0.0025 inches) might be preferable where lower pressure in the cannula 902 and system with which it is associated is desired.

The redirecting member 914 also may be configured to provide a selected flow rate for a selected pressure within the cannula 902. The flow rate is selected to provide a desired physiological result, as discussed above. It is desirable in some applications to minimize the pressure needed in the cannula 902. For example, by reducing pressure in the cannula 902, the likelihood for damage to the blood, e.g., by hemolysis, can be reduced. Also, the size and power consumption of the pump with which the cannula 902 is coupled can be reduced where less pressure is needed in the cannula 902 to achieve the selected flow rate. For a given pressure, the flow rate through the lateral openings 912 can be increased by reducing the distal-to-proximal dimension of the redirecting member 914 with respect to the distal-to-proximal dimension of the lateral openings 912. By shortening the redirecting member 914, a portion of the lateral openings 912 may be uncovered, or otherwise unobstructed, when the member 914 is in the collapsed configuration. In one embodiment, the redirecting member 914 has a length from its proximal-to-distal of less than about 0.41 cm (0.160 inches) and the lateral opening(s) 912 have a length from proximal-to-distal of at least about 0.41 cm (0.160 inches).

In addition to an increase in the flow rate, the uncovered or unobstructed portion causes a significant pressure drop in the tip portion 906. Such a pressure drop generally reduces the expandability of the member 914. The pressure in the cannula 902 can be increased to provide equivalent expansion of a redirecting member 914 that is otherwise the same as a fully covering member. Equivalent expansion can also be provided by altering the redirecting member 914. For example, the thickness of the redirecting member 914 can be reduced to enable it to expand an equivalent amount as a fully covering member at a lower pressure. Also, the hardness of the redirecting member 914 can be reduced to enable the member 914 to expand an equivalent amount at a lower pressure.

In one embodiment, the cannula 902 has a binary construction that provides a redirecting member 914 that has two discrete pre-defined configurations. This construction is analogous to that of an umbrella, which may be actuated from a collapsed, low profile configuration to a pre-determined, expanded operational configuration. In one embodiment, the redirecting member 914 has a first, pre-defined configuration for delivery, e.g., a collapsed configuration, and a second, pre-defined configuration for operation. The delivery configuration preferably is a low-profile configuration wherein the redirecting member 914 is collapsed onto an outer surface of the cannula 902. As discussed more fully below, the surface upon which the redirecting member 914 is collapsed may be recessed into the outer wall of the cannula 902 to eliminate a step along the outer wall between the redirecting member 914 and the cannula 902.

In one embodiment, the redirecting member 914 is expandable to a pre-formed, expanded shape in the operational configuration. In one embodiment, a proximal portion of the redirecting member 914 extends outwardly from the outer surface of the cannula 902' in the operational configuration. As discussed above the redirecting member 914 may be attached to the cannula 902 distal of the lateral openings 912. The redirecting member 914 may be biased to the pre-defined, expanded shape such that when actuated to the operational configuration, the member 914 moves from the collapsed configuration to the pre-defined, expanded shape. The redirecting member 914 may be actuated from the delivery configuration to the operational configuration as pressure in the blood-flow lumen initially increases during operation. In one embodiment, when a pre-determined threshold pressure differential across the member 914 is reached, the member 914 is actuated, e.g. swings out at the proximal end thereof, to the pre-defined operational configuration. The embodiments of the redirecting member 914 that have a pre-formed, expanded shape can be constructed of PET or any other suitable material. In the operational configuration, blood may flow through the lateral openings 912 into the vessel V. The lateral openings 912 thus act as discharge openings through which blood may flow into the vessel V.

As discussed above, in one embodiment, the tip portion 906 is provided with a recess 918 in which the redirecting member 914 seats during delivery of the cannula 902, before the cannula 902 is put into operation. The recess 918 advantageously eliminates any ridge or step between the tip portion 906 and the redirecting member 914 which could become hung-up on tissue during insertion or withdrawal of the cannula 902. The recess 918 is not required. For example, the redirecting member 914 could be made with negligible thickness so that the cannula 902 can be easily inserted percutaneously.

In another embodiment, the tip portion 906 includes a surface 920 that extends at least partially across the lumen 910 at the distal end thereof. The surface 920 is preferably formed to partially redirect the blood flowing through the lumen 910 in a direction other than that of flow in the lumen, e.g., perpendicular to the flow of blood in the lumen 910 and into the redirecting member 914. The surface 920 is preferably a curved surface capable of directing blood-flow through the lateral openings 912. Thus, the surface 920 and/or the redirecting member 914 direct the blood in a direction generally opposite of the direction of blood-flow in the lumen 910. By redirecting the flow in this manner, the cannula 902 may advantageously prevent blood-flow exiting the tip portion 906 from immediately discharging against a wall of the vessel. The likelihood of any deleterious effect on the vessel in which the cannula 902 is applied or other harm to the vasculature due to the operation of the cannula 902 is thereby reduced.

In another embodiment, the tip portion 906 includes a tapered portion 922. In one embodiment the tapered portion 922 extends between the redirecting member 914 and the distal end 908 of the cannula 902. As discussed above, providing a tapered portion may advantageously ease percutaneous insertion of the cannula 902 into the vasculature of the patient.

Another embodiment of the tip portion 906 provides a guide-member lumen 924 to accommodate a guide-member such as a guidewire. As discussed above, a guide-member can provide a means for inserting the cannula 902 to a selected location within the vasculature of the patient. The guide-member lumen 924 can be configured to receive a guide-member, such as a guidewire, during delivery of the cannula 902. Where the guide-member is thereafter removed, it may be beneficial to provide means for sealing the guide-member lumen 924. The sealing means is similar to the sealing means described above in connection with the embodiment of FIGS. 21A-21C. In one form, the sealing means is a valve 926. The valve may be a mechanical or non mechanical valve that closes after a guide-member is removed from the guide-member lumen 924. The sealing means could also be a plug, such as one that forms after the cannula 902 is inserted, as discussed above.

Figure 23C:
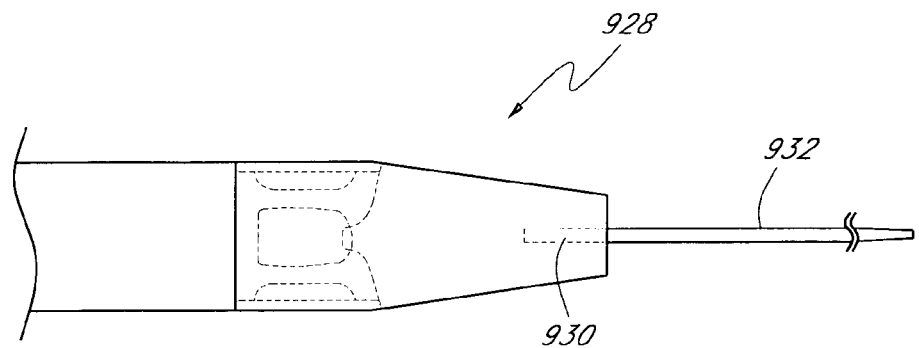
FIG. 23C is a schematic view of another embodiment of a cannula having a redirecting tip with an integral guide-member.

With reference to FIG. 23C, another embodiment of a cannula 928, which is similar to the cannula 902, defines a recess 930 in which a guide-member 932 is embedded. The guide-member 932 assists in delivering the cannula 928 to a selected portion of a selected vessel. By embedding the guide-member 932 in the recess 930, the guide-member 932 is permitted to remain in place during the operation of the cannula 928, which may simplify the procedure. Also, blood is prevented from flowing out the distal end of the cannula 928 without providing a valve. The cannula 928 may be configured as a single or a multiple lumen cannula, as discussed above.

Figure 23D:
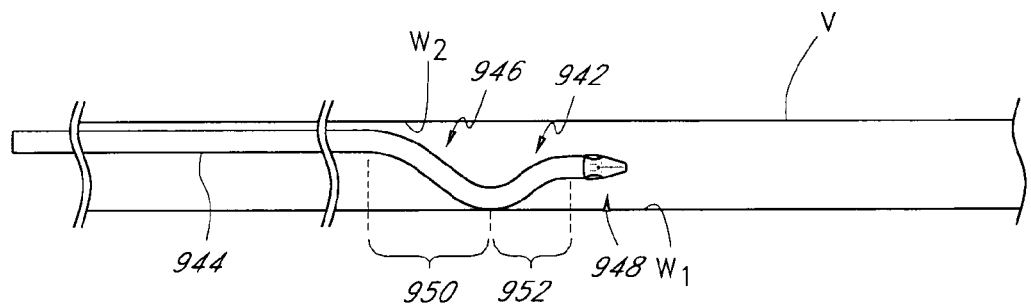
FIG. 23D is a schematic view of another embodiment of a cannula having a positioning portion for locating a tip portion thereof.

Another embodiment of a cannula 942, which is similar to the cannula 902, includes a main cannula portion 944, a transition portion 946, and a tip portion 948 (see FIG. 23D). The cannula 942 also has a lumen extending therethrough that is similar to the lumen 910 in one embodiment. The cannula 942 may be configured as a single or a multiple lumen cannula, as discussed above. The main cannula portion 944 is similar to the main cannula portion 904 and the tip portion 948 is similar to the tip portion 906. The transition portion 946, which has a lumen extending therethrough, is configured to locate the tip portion 948 within the vessel V. Preferably, the transition portion 946 has a first configuration suitable for delivering the cannula 942 and a second configuration suitable for operation of the cannula 942. In one embodiment, the first configuration is a low-profile configuration that eases insertion of the cannula 942 into the vasculature.

The second configuration preferably is a generally S-shaped configuration. The S-shaped configuration provides a first lateral extending portion 950 and a second laterally extending portion 952. The first laterally extending portion 950 may extend laterally until it engages a wall $W_1$ of the vessel V. The lateral extent of the first laterally extending portion 950 is preferably sufficient to cause the distal end of the main cannula portion 944 to be moved adjacent to, or even to engage, the opposite wall $W_2$ of the vessel V. The lateral extent of the second laterally extending portion 952 is preferably sufficient to position the distal end of the transition portion 946 about in the center of the vessel V. In another embodiment, the second laterally extending portion 952 extends laterally to engage the wall $W_1$ of the vessel and, thereafter, toward the center of the vessel V to space the tip portion 948 from both the wall $W_1$ and the wall $W_2$. As discussed above in connection with the embodiment of FIGS. 19A-19B, spacing the tip portion 948 can enhance the manner in which the cannula 942 interacts with the vessel V, e.g., by providing a gap between where the blood-flow exits the tip portion 948 and the nearest vessel wall. Providing such a gap is one way to substantially preventing blood discharging from a blood flow lumen through a discharge opening in the cannula 942 from directly impacting upon any blood vessel walls.

The cannula 942 is illustrated having a tip similar to the tip 906. Any of the other cannulae described here could be configured with a positioning portion similar to the transition portion 946 to orient and the tip portion and to space the tip portion and the blood-flow apertures, windows, and openings from the wall(s) of the vessel.

Figure 24:
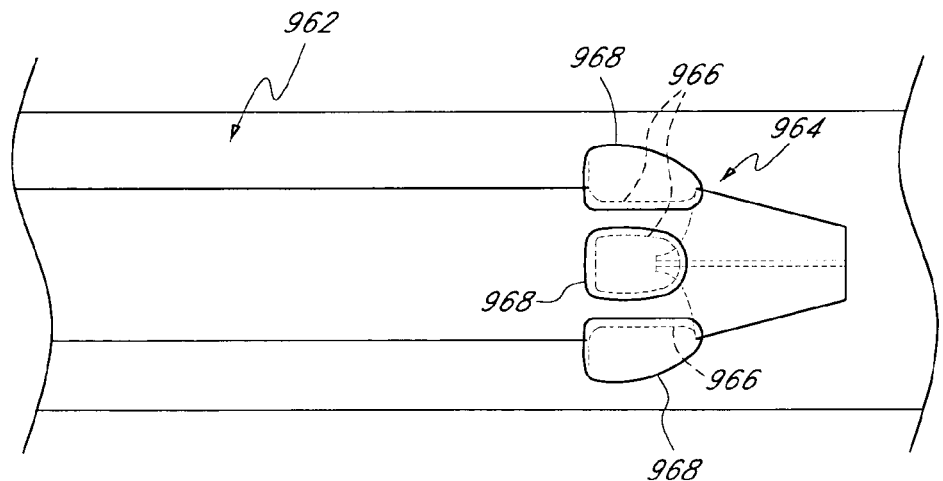
FIG. 24 is a schematic view of another embodiment of a cannula having a redirecting tip, the cannula being deployed in a patient's vasculature.

Another embodiment of a cannula 962, illustrated in FIG. 24, has a tip portion 964 with a plurality of lateral openings 966 and a plurality of redirecting members 968, one of which corresponds to and at least partially spans each of the lateral openings 966. The lateral openings 966 are discharge openings in some applications of the cannula 962. The lateral openings 966 and redirecting member 968, like the lateral openings 912, can be uniformly spaced radially around the cannula 962. As discussed above in connection with the redirecting member 914, the redirecting members 968 can take any suitable form, e.g., continuously expandable, discretely expandable (e.g., by way of a pre-formed member), or a combination thereof. The cannula 962 may be configured as a single or a multiple lumen cannula, as discussed above.

This arrangement may advantageously permit use of different materials for the redirecting members 968 than would be used for the redirecting member 914, e.g., materials that are less or more flexible. Also, this arrangement may permit the redirecting members 936 to be thinner than the redirecting member 914. Thinner expandable members 936 may permit the cannula 962 to be easily inserted percutaneously, but more simply made than the cannula 902, e.g., by eliminating the recess 916.

Figure 25:
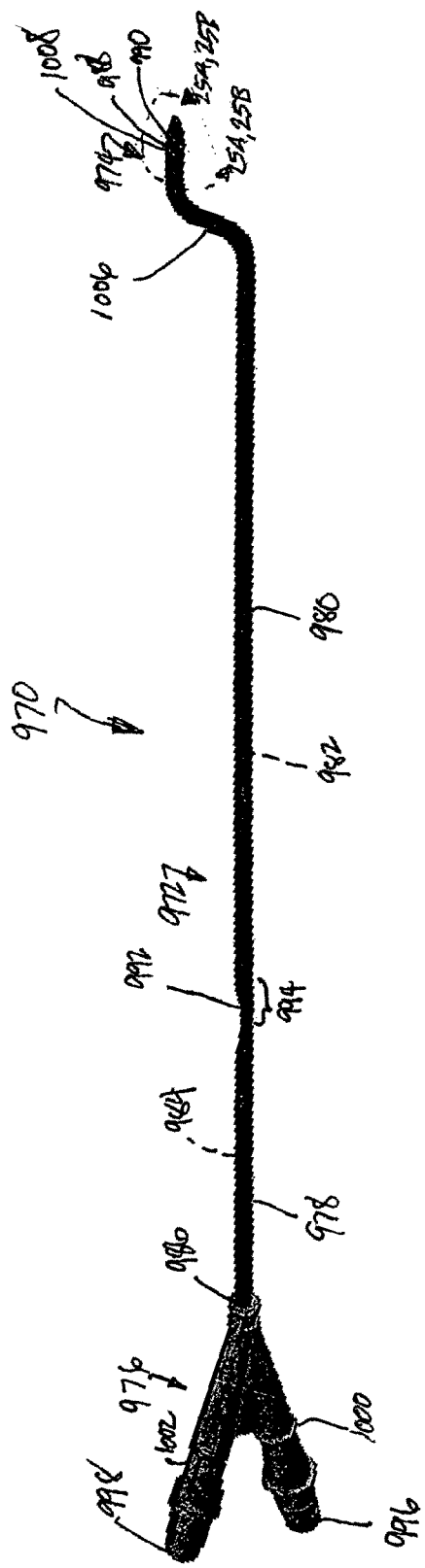
FIG. 25 is a perspective view of another embodiment of a cannula having a redirecting tip and a flow resistance reducing lumen.

FIG. 25 illustrates another embodiment of a cannula 970. The cannula 970 is a percutaneous cannula in that it is particularly well suited for insertion into a patient by way of a minimally invasive procedure, e.g., one employing a Seldinger technique. The cannula 970 can be inserted over a wire or with the aid of a dilator, obturator, or other structure configured to provide stiffness to or induce a low-profile shape in the cannula 970. Such an arrangement may be analogous to that shown in FIGS. 17C and 18B. The cannula 970 is also capable of fluidly communicating with the patient's vasculature and may be used in connection with the systems described herein. In one arrangement, the cannula 970 is configured to exchange blood within a patient's vasculature, e.g., to withdraw and to discharge blood within the patient's vasculature. In one embodiment, the cannula 970 includes a main cannula portion 972, a tip portion 974, and a connector 976.

The main cannula portion 972 includes a proximal portion 978, a distal portion 980, a first lumen 982, and a second lumen 984. In one embodiment, the proximal portion 978 has a proximal end 986 at which the connector 976 is connected, formed, or otherwise coupled with the proximal portion 978 of the main cannula portion 972.

At least a portion of the first lumen 982 is formed within the proximal portion 978 in one embodiment. In one embodiment, the first lumen 982 extends between the proximal end 978 and a discharge opening 988 located in the tip portion 974, as discussed more fully below. In some embodiments, the discharge opening 988 defines, at least in part, a first distal end 990 of the first lumen 982.

At least a portion of the second lumen 984 is also formed within the proximal portion 978 in one embodiment. In one arrangement, the second lumen 984 extends distally to a second distal end 992. In one embodiment, the second distal end 992 defines the distal end of the proximal portion 978. In the illustrated embodiment, the first lumen 982 is longer than the second lumen 984. The main cannula portion 972 can be configured such that the second lumen 984 extends distally beyond the proximal portion 978. The second lumen 984 may be as long as or longer than the first lumen 982 in some embodiments.

The arrangement of the first and second lumens 982, 984, may take any suitable form. In some embodiments, one or both of the first and second lumens 982, 984 is relatively long. For example, in various applications, the cannula 970 is configured so that it can be inserted into the vasculature at a femoral artery and advanced until the first distal end 990 is located in the descending aorta, e.g., just above a renal artery, near the top of the descending aorta, or at a location between a renal artery and the top of the descending aorta. In some applications, the cannula 970 is configured so that it can be inserted into the vasculature at a femoral artery and advanced until the first distal end 990 is adjacent to or within a branch artery, e.g., a renal artery. In some applications, the cannula 970 is configured so that it can be inserted into the vasculature at another non-primary artery, e.g., an axillary artery, and advanced until the first distal end 990 is at, adjacent to, or within any of the foregoing arteries (e.g., an iliac or femoral artery) or any other of the vessels or classes of vessels described herein.

In one embodiment, the cannula 970 is configured so that the length of the first lumen 982 from the proximal end 986 to the first distal end 990 is between about 60 and about 90 cm. In another one embodiment, the cannula 970 is configured so that the length of the first lumen 982 from the proximal end 986 to the first distal end 990 is between about 30 and about 60 cm. In one embodiment, the first lumen 982 is about 74 cm long. The length of the second lumen 984 from the proximal end 986 to the second distal end 992 is between about 10 and about 30 cm in one embodiment. In one embodiment, the second lumen 984 is about 20 cm long.

As discussed in greater detail below, it may be beneficial to reduce the flow resistance in one or more of the first and the second lumens 982, 984. One technique for reducing the effect of flow resistance is to increase the cross-sectional area of at least one of the first and second lumens 982, 984. As discussed more fully below, this may be accomplished by providing the main cannula portion 972 with a transition portion 994 wherein the size of the first lumen 982 increases from proximal to distal. In this embodiment, the first lumen 982 has a first cross-sectional area within the proximal portion 978 and a second cross-sectional area within the distal portion 980, wherein the second cross-sectional area is greater than the first cross-sectional area. The first and second lumens 982, 984 may have constant cross-sectional profiles throughout the length of the proximal portion 978 and may have a constant cross-sectional area through the length of the distal portion 980. In various embodiments, the first and second lumens 982, 984 may have non-constant cross-sectional profiles in at least one of the proximal and distal portions 978, 980.

As discussed more fully below, this arrangement reduces the effect of flow resistance within at least one lumen, e.g., in the first lumen 982. Reducing the flow resistance has corresponding benefits, including: (a) enabling the cannula 970 to be made smaller with flow corresponding to a larger cannula not configured to reduce the effects of flow resistance; (b) enabling pumps with lower power requirements to be used in a blood supplementation system; (c) reducing the detrimental effect of wall shear on blood flowing in the lumen; and other benefits described herein. The flow resistance reducing strategies described hereinbelow may be deployed on one or more lumens of a multilumen cannula (e.g., on one or both of the first and second lumens 982, 984) or on a lumen of a single lumen cannula. Other arrangements for reducing the flow resistance in a lumen and other features that may be incorporated into the cannula 970 or any other of the cannulae described herein are discussed hereinbelow in connection with FIGS. 26-32B.

As discussed above, the connector 976 of the cannula 970 is provided in some embodiments. The connector 976 has a Y shape in some embodiments and is sometimes referred to herein as a Y connector. The connector 976 provides a convenient way to connect the cannula 970 to other components of a system, e.g., a pump. The cannula 970 may be combined with any suitable pump useful in performing a treatment, e.g., any of the pumps described herein. In one embodiment, the connector 976 includes a first connector 996 and a second connector 998. The first connector 996 is in fluid communication with the first lumen 982 and the second connector 998 is in fluid communication with the second lumen 984. In one arrangement, a lumen is provided in each of a first hub 1000 and a second hub 1002 of the connector 976. The lumens in the connector 976 communicate with the first and second lumens 982, 984 of the main cannula portion 972. In use, each of the first and second connectors 996, 998 is coupled with another component of a system for treating a patient, e.g., directly to inlet and outlet ports of a pump, or to one or more lengths of tubing provided between the connector 976 and a pump or other component.

The tip portion 974 may extend from the main cannula portion 972 or form a part thereof and may take any suitable form. In one embodiment, the tip portion is similar to the tip portion of FIGS. 23A-23D, except as set forth below.

FIG. 25 shows that in one embodiment, the tip portion 974 has a transition portion 1006 and a redirecting member 1008. The transition portion 1006 is similar to the transition portions discussed above (e.g., in connection with FIGS. 17A, 18A, 19A, and 23D). The transition portion 1006 is configured to position a portion of the tip portion 974 at a selected location. For example, the transition portion 1006 may be configured to position the discharge opening 988 at a selected distance from a vessel wall. The transition portion 1006 is configured to reposition the discharge opening 988 at a selected location within the same vessel in which the distal portion 980 of the main cannula portion 972 resides in one application. The transition portion 1006 is preformed in one embodiment. In another embodiment, the transition portion 1006 comprises a shape that is induced in the tip portion 974 after the cannula 970 is applied to the patient. Where the tip portion 1006 is preformed, a device may be used to straighten the tip portion 1006 to give it a lower profile for introduction into the vasculature. The spacing provided by the transition portion 1006 may protect the vessel wall from damage caused by outflow. The spacing provided by the transition portion 1006 may ensure that the tip portion can be fully deployed (e.g., ensuring that the redirecting member 1008 is able to open fully). In some, embodiments, the redirecting member 1008 is configured (e.g., made sufficiently stiff) so that the expansion of the redirecting member 1008 causes the opening 988 to be spaced from a vessel wall. In other embodiment, the tip portion 974 is similar to or incorporates at least one feature of any of the other tip portions described herein.

The redirecting member 1008 is similar to the redirecting member 914 discussed above. In particular, the redirecting member 1008 preferably is arranged to expand under the pressure a lumen (e.g., the first lumen 982) of the cannula 970 to uncover openings (which may be discharge openings 988) in the tip portion 974. In one embodiment, the redirecting member 1008 has a range of degrees of expansion, similar to the range of degrees of expansion of a balloon. In another embodiment, the redirecting member 1008 is actuatable between discrete configurations, e.g., between a collapsed configuration and an expanded configuration, in a manner similar to an umbrella. The pressure in the lumen may be generated by any suitable pump coupled with the cannula 970. The pressure causes the member 1008 to expand from a first configuration, which may be a low-profile configuration, shown in FIG. 25A to a second configuration, which may be an operating configuration, shown in FIG. 25B. In one application, blood flow is directed through the openings 988 in the cannula 970 in the second configuration. The blood flow may further be discharged through the discharge opening and directed proximally along the cannula 970, as indicated by the arrows in FIG. 25B. The redirecting member 1008 also is collapsible to cover the discharge openings 988 during insertion of the cannula 970.

FIGS. 26-32B illustrate further cannulae that may be used in connection with any of the systems described herein. Any of the features of any of these cannulae may be combined with any of the features of any of the foregoing cannulae.

Figure 26:
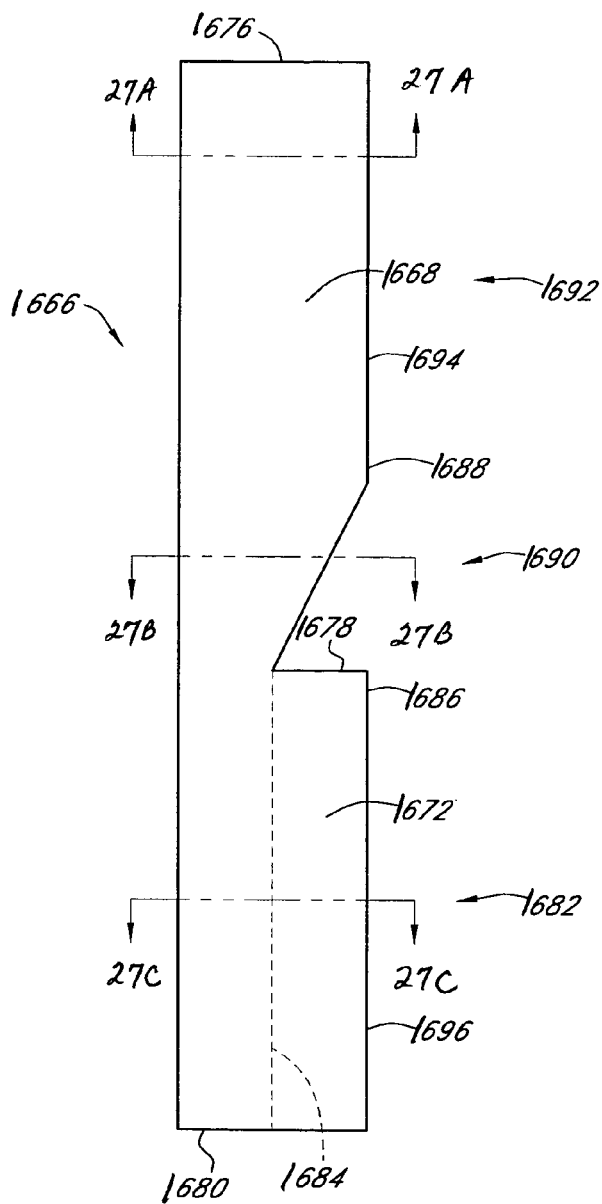
FIG. 26 is a schematic view of one embodiment of a multilumen cannula having a variable size lumen.
Figure 27A:
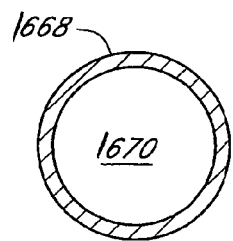
FIG. 27A is a cross-section view of the multilumen cannula of FIG. 26 taken along section plane 27A-27A.
Figure 27B:
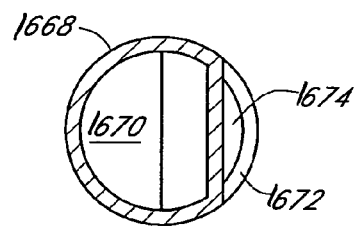
FIG. 27B is a cross-section view of the multilumen cannula of FIG. 26 taken along section plane 27B-27B.
Figure 27C:
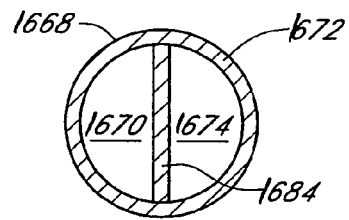
FIG. 27C is a cross-section view of the multilumen cannula of FIG. 26 taken along section plane 27C-27C.

Referring to FIGS. 26-27C, one embodiment of a multilumen cannula 1666 that includes a first elongate portion 1668 defining a first lumen 1670 and a second elongate portion 1672 defining a second lumen 1674. The first elongate portion 1668 extends between a first distal end 1676 and a proximal end 1680. The second elongate portion 1672 extends between a second distal end 1678 and the proximal end 1680. The first distal end 1676 of the first elongate portion 1668 extends distally farther from the proximal end 1680 of the multilumen cannula 1666 than does the second distal end 1678.

The multilumen cannula 1666 includes a proximal portion 1682 wherein the first and second elongate portions 1668, 1672 extend generally side-by-side, at least partially separated by a wall 1684. As shown in FIG. 27C, the elongate portions 1668, 1672 and the wall 1684 in the proximal portion 1682 of the multilumen cannula 1666 form two lumens with D-shaped cross-sections 1670, 1674. Although the lumens 1670, 1674 are shown as having approximately the same size, other relative sizes are possible. For example, the shorter lumen 1674 could be made smaller than the longer lumen 1670. Other arrangements of side-by-side lumens are also possible, e.g., where the lumens have shapes other than that shown in FIG. 27C. For example, the lumens 1670, 1674 could be circular in cross-section (or any other suitable shape) rather than D-shaped.

With reference to FIGS. 27A and 27B, the inner cross-sectional size of the first lumen 1670 expands distal the second distal end 1676 compared to the inner cross-sectional size of the first lumen 1670 in the proximal portion 1682 of the multilumen cannula 1666. The expanded size of the first lumen 1670 makes the inner cross-sectional area of the first lumen 1670 greater at the first distal end 1676 than at the proximal end 1680. In one embodiment, the elongate portion 1668 of the multilumen cannula 1666 increases from about a seven French size in the proximal portion 1682 to about a twelve French size in the distal portion 1692. In other embodiments, at least about a one hundred percent increase in the size of the lumen 1670 in the elongate portion 1668 at the distal end 1676 compared to the proximal end 1680 is provided. The length of the transition portion 1690 may be any suitable length, e.g., one that provides gradual increase distally to prevent abrupt changes in aspects of the flow of the blood (e.g., the flow direction). In one embodiment, the length of the transition portion 1690 is about one inch. In one embodiment, the length of the transition portion 1690 is about one inch or less. In another embodiment, the length of the transition portion 1690 is about one-half inch. As previously discussed, increasing the inner cross-section size of the first lumen 1670 at any point along the length of the cannula 1666 will decrease the overall flow resistance of a heart-assist system employing the cannula 1666. It is expected that the decrease in flow resistance would be most significant when the inner cross-section of the first lumen 1670 is increased for as much of the length as is possible.

The cannula 1666 has a transition portion 1690 wherein the cross sectional size of the first elongate portion 1668 expands. The transition portion 1690 preferably extends from proximate the second distal end 1678 of the second elongate portion 1672 to a location 1688 distal the second distal end 1678. The cross-sectional size of the cannula 1666 distal the location 1688 preferably is about equal to the cross-sectional size of the proximal portion 1682 at a location 1686 just proximal the second distal end 1678.

With reference to FIG. 27B, the cross-section size of the lumen 1670 increases from proximal to distal within the transition portion 1690. The increase in cross-section size of the lumen 1670 may be achieved in any suitable manner. Preferably, the location of the wall 1684 in the transition portion 1690 gradually moves transversely from proximal to distal such that the D-shape of the lumen 1670 in the proximal portion 1682 of the cannula 1666 transitions gradually to a more circular cross-sectional shape toward the distal end of the transition portion 1690. Distal the location 1688 (e.g., at a location 1694) the inner cross-sectional shape of the first lumen 1670 preferably becomes circular, as illustrated in FIG. 27A.

The cannula 1666 preferably comprises a distal portion 1692 wherein the cross-sectional size of the cannula 1666 is substantially the same as the cross-sectional size of the cannula 1666 in the proximal portion 1682, and the interior cross-section of the first lumen 1670 is circular.

The multilumen cannula 1666 is also configured in an advantageous manner for insertion into the vasculature of a patient. The proximal and distal portions 1682, 1692 of the multilumen cannula 1666 provide a substantially constant outer cross-sectional profile. In particular, the outer cross-sectional size of the multilumen cannula 1666 is substantially the same at the location 1686, immediately proximal the second distal end 1678 and at the location 1688, immediately distal the transition portion 1690.

In some embodiments, it may be desirable to minimize the length of the transition portion 1690 to ease insertion of the cannula 1666 into the vasculature of a patient. Minimizing the transition portion 1690 is further advantageous because the length of the distal portion 1692 may be increased to further reduce the overall flow resistance of the cannula 1666. However, factors such as the amount of blood flow through the second distal end 1678 and the flow of blood through the lumen 1670 within the transition portion 1690 may place a lower limit on the length of the transition portion 1690.

In order to minimize the flow resistance in the cannula 1666, it is desirable to design the cannula so that the distal portion 1692 comprises as much of the total length of the cannula 1666 as is possible, given other constraints on the cannula 1666. Thus, the length of the proximal portion 1682, and therefore the length of the second lumen 1674, will be minimized as much as is possible. The flow resistance will thus be decreased both because the portion of the first lumen 1670 that is increased in size is increased and the portion of the first lumen 1670 that is decrease in size is decreased.

Figures 28, 29A, 29B, 29C:
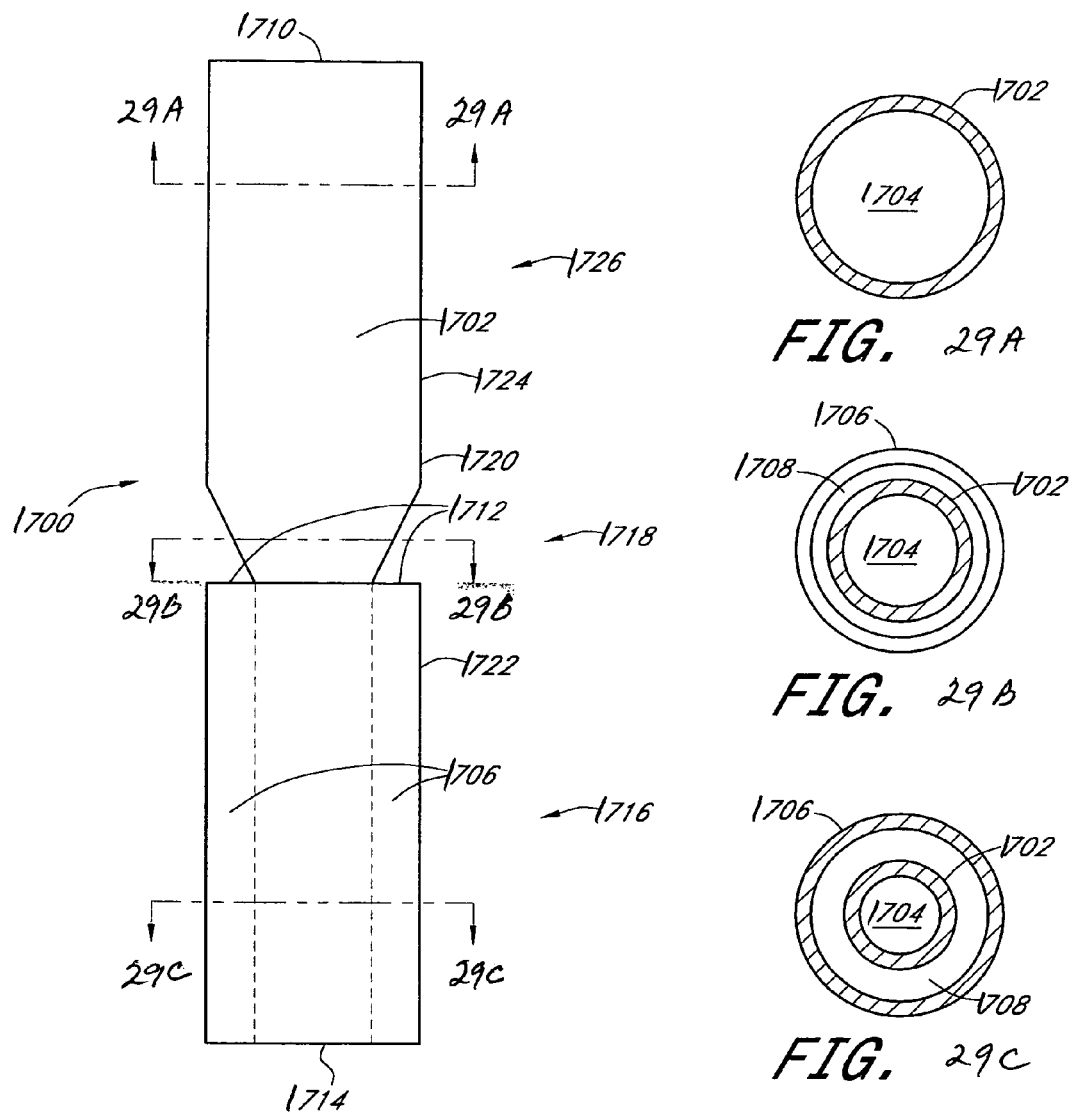
FIG. 28 is a schematic view of another embodiment of a multilumen cannula having a variable size lumen.
FIG. 29A is a cross-section view of the multilumen cannula of FIG. 28 taken along section plane 29A-29A.
FIG. 29B is a cross-section view of the multilumen cannula of FIG. 28 taken along section plane 29B-29B.
FIG. 29C is a cross-section view of the multilumen cannula of FIG. 28 taken along section plane 29C-29C.

Referring to FIG. 28, another embodiment of a multilumen cannula 1700 includes a first elongate portion 1702 defining a first lumen 1704 and a second elongate portion 1706 defining a second lumen 1708. The lumens 1704, 1708 are shown more clearly in FIGS. 29A-29C. The first elongate portion 1702 extends between a first distal end 1710 and a proximal end 1714. The second elongate portion 1706 extends between a second distal end 1712 and the proximal end 1714. The first distal end 1710 of the first elongate portion 1702 extends distally farther from the proximal end 1714 of the multilumen cannula 1700 than does the second distal end 1712.

In this embodiment, the multilumen cannula 1700 includes a proximal portion 1716, a transition portion 1718, and a distal portion 1726. In the proximal portion 1716 of the cannula 1700, the first and second elongate portions 1702, 1706 extend generally parallel to each other. In the illustrated embodiment, the first elongate portion 1702 extends through the second lumen 1708 defined in the second elongate portion 1706. In this arrangement, the first and second elongate portions 1702, 1706 form two concentric circles in cross-section, as shown in FIGS. 29B-29C.

The transition portion 1718 of the multilumen cannula 1700 preferably extends from a location proximate to the second distal end 1712 of the second elongate portion 1706 to a location 1720 longitudinally between the second distal end 1712 and the first distal end 1710. The first elongate portion 1702 generally expands distally in the transition portion 1718. In one embodiment, the transition portion 1718 expands distally continuously. In another embodiment, the transition portion 1718 expands distally continuously and at a constant rate. The expansion of the first elongate portion 1702 corresponds to an increase in the girth of the elongate portion 1702, e.g., to an increase in the outer diameter thereof. In one embodiment, the thickness of the wall defining the elongate portion 1702 is held constant from proximal to distal through the transition portion 1718. Because the wall thickness is constant, and the outer size of the elongate portion 1702 in the transition portion 1718 is expanding, the first lumen 1704 in the transition portion correspondingly increases from proximal to distal. In one embodiment, the elongate portion 1702 increases from about a seven French size in the proximal portion 1716 to about a twelve French size in the distal portion 1726. In other embodiments, at least about a one hundred percent increase in the size of the lumen 1704 in the elongate portion 1702 at the distal end 1712 compared to the proximal end 1714 is provided. The length of the transition portion 1718 may be any suitable length, e.g., one that provides gradual increase distally to prevent abrupt changes in aspects, of the flow direction of the blood (e.g., the flow direction). In one embodiment, the length of the transition portion 1718 is about one-half inch. In one embodiment, the length of the transition portion 1718 is about one inch or less. In another embodiment, the length of the transition portion 1718 is about one inch. As discussed above, this increase advantageously increases the cross-sectional area of the lumen through which blood may flow, which reduces the magnitude of fluid-dynamic losses due to flow resistance. Of course, the thickness of the wall defining the elongate portion 1702 in the transition portion 1718 need not remain constant. Rather the wall can thicken or become thinner as desired.

In one embodiment, the cross-section shape of the first lumen 1704 in the transition portion 1718 is the same as the cross-sectional shape of the first lumen 1704 in the proximal portion 1716. In one embodiment, the cross-sectional shape of the first lumen 1704 in the transition portion 1718 and in the proximal portion 1716 is circular.

The distal portion 1726 of the cannula 1700 is that portion residing distal the transition portion 1718. The size of the distal portion 1726 of the cannula 1700 (e.g., the outer diameter) preferably is substantially the same as the size of the proximal portion 1716 of the cannula 1700. The shape of the second lumen 1704 in the distal portion 1726 preferably is the same as the shape of the second lumen 1704 in the transition portion 1718, e.g., circular. The circular cross-sectional shape of the second lumen 1704 in the distal portion 1726 is shown in FIG. 29A.

With reference to FIGS. 29A and 29B, the inner cross-sectional size of the first lumen 1704 expands distal the second distal end 1712 compared to the inner cross-sectional size of the first lumen 1704 in the proximal portion 1716 of the multilumen cannula 1700. The expanded size of the first lumen 1704 makes the inner cross-section of the first lumen 1704 greater at the first distal end 1710 than at the proximal end 1714. As previously discussed, this configuration is advantageous in that the cannula 1700 has lower flow resistance compared to a cannula of comparable length with a constant inner cross-sectional size equal to inner cross-sectional size of the lumen 1704 in the proximal portion 1716 of the cannula 1700.

The multilumen cannula 1700 is also configured in an advantageous manner for insertion into the vasculature of a patient. In the illustrated embodiment, both the proximal portion 1716 and the distal portion 1726 provide a substantially constant outer cross-sectional profile. In particular, the outer cross-sectional size of the multilumen cannula 1700 is substantially the same at a location 1722 immediately proximal the second distal end 1712 and at a location 1720 immediately distal the transition portion 1718.

As discussed above in connection with FIG. 26, minimizing the length of the transition portion 1718 may be advantageous. Also, it is desirable for the distal portion 1724 of the first elongate portion 1702 to be as long as possible and for the proximal portion 1716 of the first elongate portion 1702 to be as short as possible, given other constraints on the cannula design.

Figures 28A, 28B:
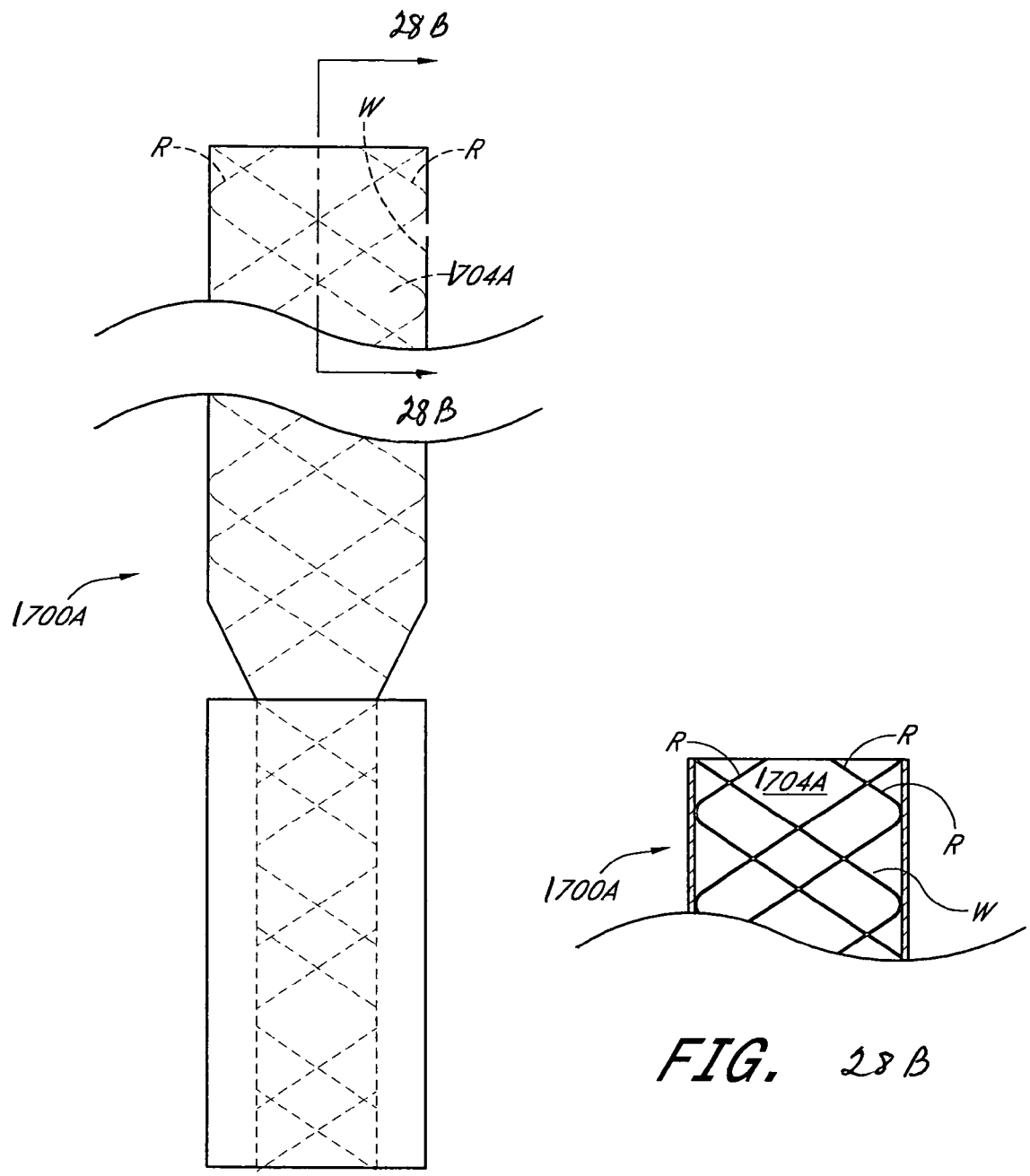
FIG. 28A is a schematic view of another embodiment of a multilumen cannula configured to impart a rotational component to the flow of fluid in a lumen.
FIG. 28B is a cross-sectional view of the multilumen cannula of FIG. 28A taken along section plane 28B-28B.

Referring to FIG. 28A, another embodiment of a multilumen cannula 1700A is configured to impart a rotational component to the flow of fluid therein (e.g., a vortex flow). The cannula 1700A is similar to the cannula 1700, except as set forth below. In one embodiment, the walls W that surround a lumen 1704A of the cannula 1700A are configured to impart a rotation component to the flow of fluid in the lumen 1704A. Any suitable structure may be employed to impart the rotational component to the flow. One benefit of imparting a rotational component to the flow is that resistance to flow may be reduced, providing some or all of the benefits of reduced resistance flow, including those described herein.

In one embodiment, the walls W of the cannula 1700A is configured to impart a rotational component of the flow of fluid therein. In the illustrated embodiment, the walls W of the cannula 1700A are provided with at least one ridge R formed thereon. Any suitable configuration of the ridge R may be employed. The ridge R may be arcuate, spiraled, helical, or any other suitable shape that will impart a rotational component to the flow. In the spiraled embodiment, the density of the spiral may be any suitable density. For example, the spiral ridge R may extend about once around (e.g., about 360 degrees around) the lumen 1704A of the cannula 1700A per inch of length of the cannula 1700A. In another embodiment, the spiral ridge R may extend as many as about ten times around the lumen 1704A of the cannula 1700A per inch of length, or more. In another embodiment, the spiral ridge R may extend about once around the lumen 1704A per ten inches of the cannula 1700A, or less.

In the illustrated embodiment, a plurality of ridges R is provided. In particular, with reference to FIG. 28A, four ridges R are provided in the lumen 1704A. Other numbers of ridges may also be provided to create vortex flow, e.g., more than four, three, two, or one ridge may be provided. In one embodiment, a plurality of ridges R is provided wherein the ridges R are off-set from each other about the circumference of the lumen 1704A. For example, two ridges R may be located directly across the lumen 1704A from each other (e.g., spaced 180 degrees apart). In one embodiment, at least one of the ridges R extends from the proximal end to the distal end of the lumen 1704A. In another embodiment, at least one of the ridges R extends less than the entire length of the lumen 1704A. The ridges R and the internal structure of a portion of the lumen 1704A of the cannula 1700A are shown in greater detail in FIG. 28B.

As discussed herein, providing a cannula with a lumen that transitions to a larger size in at least a portion of a distal portion compared with a proximal portion can reduce flow resistance in the lumen compared to non-distally increasing lumen cannula. Configuring the lumen 1704A to impart a rotational component to the flow of fluid therein similarly reduces the resistance to the flow of fluid in the lumen 1704A. The cannula 1700A combines the benefits of increased lumen size, as discussed above in connection with the cannula 1700, with the benefits of providing the ridge(s) R. In some embodiments, the cannula 1700A may be have one or more ridges R as shown in FIG. 28A, but not have an increased lumen size. Such an arrangement can provide advantageous flow resistance reduction in some applications.

Referring to FIG. 30, another embodiment of a multilumen cannula 1730 is similar to the cannula 1700, except as set forth below. The cannula 1730 includes a first elongate portion 1732 defining a first lumen 1734 and a second elongate portion 1736 defining a second lumen 1738, which lumens are shown in FIGS. 31A-31C.

The first elongate portion 1732 extends between a first distal end 1740 and a proximal end 1744. The second elongate portion 1736 extends between a second distal end 1742 and the proximal end 1744. The first distal end 1740 of the first elongate portion 1732 extends distally farther from the proximal end 1744 of the multilumen cannula 1730 than does the second distal end 1742.

The multilumen cannula 1730 includes a proximal portion 1746, a transition portion 1748, and a distal portion 1756. In the proximal portion 1746, the first and second elongate portions 1732, 1736 extend generally parallel to each other, and the first elongate portion 1732 is coupled with the interior of the second elongate portion 1736. In one embodiment, the first elongate portion 1732 is attached to the second elongate portion 1736 within the second lumen 1738. In one embodiment, the first and second elongate portions 1732, 1736 form two non-concentric circles, one within another, as shown in FIG. 31C. The distal portion 1756 of the cannula 1730 has a cross-sectional size that is substantially the same as in the proximal portion 1746. The interior cross-section shape of the first lumen 1734 preferably is circular.

In the transition portion 1748 of the cannula 1730, the cross-sectional size of the first elongate portion 1732 expands in a manner similar to the first elongate portion 1702. Preferably the transition portion 1748 provides an increase in size of the first elongate portion 1732 such that at a location 1750 distal the transition portion 1748, the first elongate portion 1732 has a outer size (e.g., an outer diameter) that is about the same as the outer size of the second elongate portion 1736 at a location 1752 proximal the second distal end 1742. In one embodiment, the elongate portion 1732 increases from about a seven French size in the proximal portion 1746 to about a twelve French size in the distal portion 1754. As shown in FIGS. 31A-31C, the cross-sectional shape of the lumen 1734 preferably is circular at points within the proximal portion 1746, the transition portion 1748, and the distal portion 1754. In one embodiment, the cross-sectional shape of the second lumen 1734 is circular along the entire length of the first elongate portion 1732.

With reference to FIGS. 31B and 31C, the inner cross-sectional size of the first lumen 1734 expands compared to the inner-cross-sectional size of the first lumen 1734 in the proximal portion 1746 of the multilumen cannula 1730 distal a location corresponding to the second distal end 1742. In some embodiments, it is beneficial to provide at least about a one hundred percent increase in the size of the lumen 1734 in the elongate portion 1732 at the distal end 1740 compared to the proximal end 1744. The length of the transition portion 1748 may be any suitable length, e.g., one that provides gradual increase distally to prevent abrupt changes in flow direction of the blood. In one embodiment, the length of the transition portion 1748 is about one-half inch. In one embodiment, the length of the transition portion 1748 is about one inch or less. In another embodiment, the length of the transition portion 1748 is about one inch. The expanded size of the first lumen 1734 through the transition portion 1748 and in the distal portion 1754 may make the inner cross-section of the first lumen 1734 greater at the first distal end 1740 than at the proximal end 1744. As previously discussed, this configuration is advantageous in that the cannula 1730 has lower flow resistance compared to a cannula of comparable length with a constant inner cross-sectional size equal to inner cross-sectional size of the proximal end of the cannula 1730.

The multilumen cannula 1730 is also configured in an advantageous manner for insertion into the vasculature of a patient. In the illustrated embodiment, both the proximal portion 1746 and the distal portion 1756 provide a substantially constant cross-sectional profile. As discussed above, the outer size of the multilumen cannula 1730 is substantially the same at the location 1752 and at the location 1750. As discussed above in connection with FIG. 26, in some embodiments minimizing the length of the transition portion 1748 is advantageous.

As discussed previously, it is desirable to design the cannula 1730 so that the distal portion 1754 comprises as large a fraction of the total length of the cannula as is possible, given other constraints on the cannula design.

Figure 32A:
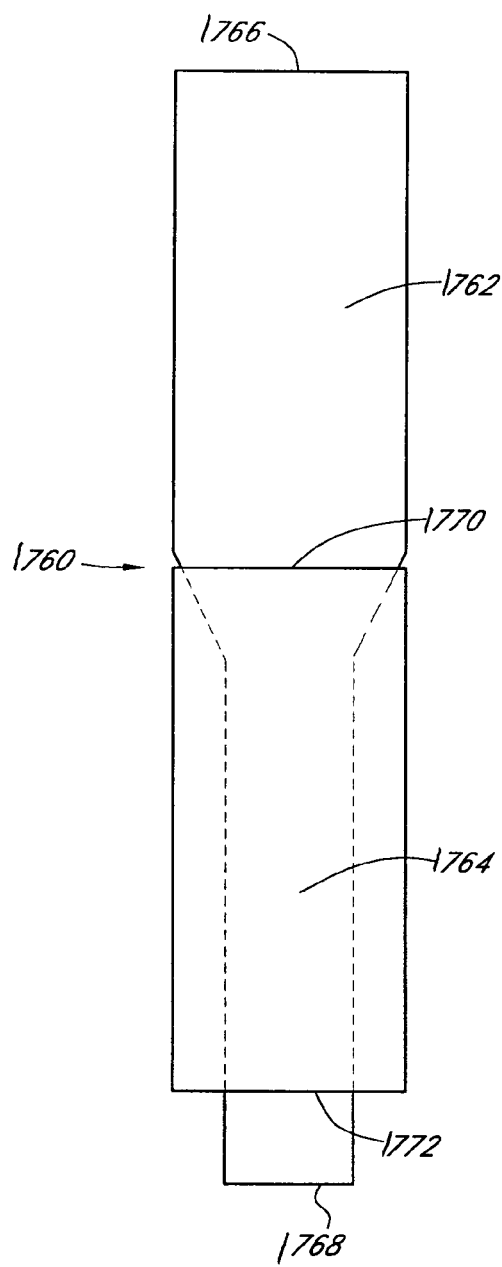
FIG. 32A is a schematic view of another embodiment of a multilumen cannula having a configuration for insertion and a configuration for operation, the configuration for insertion shown.
Figure 32B:
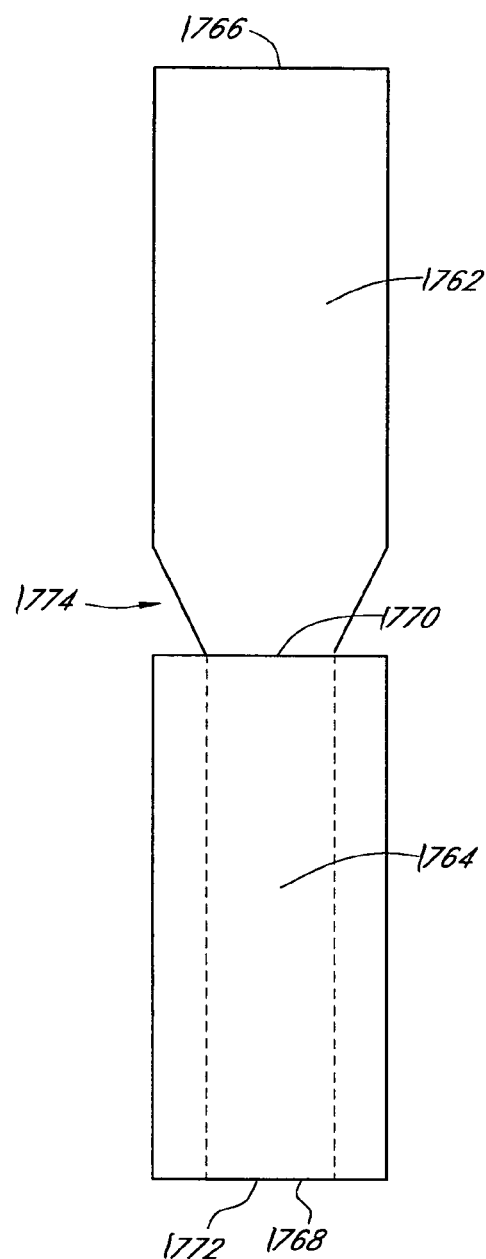
FIG. 32B is a schematic view of the multilumen cannula of FIG. 32A, showing the configuration for operation.

Referring to FIGS. 32A-32B, another embodiment of a multilumen cannula 1760 provides relative movement of two portions thereof. The cannula 1760 is similar to the cannula 1700 shown in FIGS. 27-29C, except as set forth below. The cannula 1760 has a first elongate portion 1762 and a second elongate portion 1764. The first elongate portion 1762 extends between a first distal end 1766 and a first proximal end 1768. The second elongate portion 1764 extends between a second distal end 1770 and a second proximal end 1772. The first elongate portion 1762 has a transition portion 1774, wherein the first elongate portion 1762 expands, as discussed above.

The first elongate portion 1762 and the second elongate portion 1764 of the cannula 1760 are configured to translate relative to each other. In one embodiment, the first and second elongate portions 1762, 1764 are configured to couple in a manner that permits longitudinal translation. Longitudinal translation permits the first proximal end 1768 and the second proximal end 1772 to be positioned in a variety of positions such that the distances between the first and second proximal ends 1768, 1772 varies. As discussed more fully below, the relative motion advantageously permits the second distal end 1770 to be positioned selectively at the same longitudinal position as the distal end of the transition portion (as shown in FIG. 32A) or at any suitable position proximally thereof. With reference to FIG. 32B, in one such position, the second distal end 1770 is about at the same longitudinal location as the proximal end of the transition portion 1774.

In some applications, the length of the cannulae hereinbefore described can be substantial. In such arrangements, flow resistance within the longer lumens can become significant. One detriment of increased flow resistance is a corresponding decreases in the flow (e.g., volumetric flow rate) at the distal end of the higher resistance lumen. One approach to maintain the flow at the distal end of the lumen is to increase the size of the lumen to overcome the flow reducing effect of flow resistance. However, the systems described herein often are deployed in relatively small vessels. For such applications, it is desirable to maintain the flow at the distal end of the lumen and to keep the cannulae relatively small. Reducing the resistance is one approach to maintain the flow at the distal end without greatly increasing the size of the cannulae. Another detriment of increased flow resistance is a corresponding increase in the power required to pump the blood through the cannulae. This increased power requirement may necessitate a larger pump, more frequent battery changes where the system is battery powered (e.g., for a portable system), or more frequent pump replacement. In many arrangements, e.g., where the pump is to be implanted into the patient, or the patient is desired to be ambulatory, it is desirable to minimize both the size and power consumption of the pump.

It is believed that power consumption can be reduced by reducing the flow resistance in these cannulae. The flow resistance of a cannula can be reduced by decreasing the overall length of the cannula, decreasing the viscosity of the fluid, or increasing the cross-sectional size of the cannula lumen or interior, as discussed above. The total cross-sectional size of the cannula is restricted by the size of the blood vessel into which the cannula is inserted. However, it is believed that an increase in the cross-sectional size of the lumens defined in the cannulae for at least a portion of the total length of the cannulae will result in a decrease in the overall flow resistance of the cannulae. Thus, the cannulae described herein are configured in this manner to reduce resistance to flow in relatively long lumens.

Reducing the resistance to the flow of blood in a lumen of a cannula can have additional benefits. For example, higher flow resistance in the lumen corresponds to a higher shear force being exerted on the blood flowing in the lumen. The exertion of higher shear force on the blood tends to increase the likelihood that the blood will be damaged, e.g., by hemolysis. Reducing the shear force being exerted on the blood tends to reduce the likelihood that the blood will be damaged, e.g., by hemolysis. The shear force being exerted on the blood advantageously may be reduced by reducing the resistance to blood flow in the lumen. As discussed herein, such flow resistance reduction may be accomplished by at least one of configuring the lumen to induce a rotation flow in the blood and increasing the size of at least a portion of the lumen.

Also, the longer the blood is subject to higher shear force, the greater the damage that may result to the blood. Accordingly, further benefit may be achieved by reducing the shear force being exerted on the blood for as much of the length of the lumen as possible. Accordingly, as discussed above, a greater benefit may be achieved by at least one of providing over as much of the lumen as possible a configuration that induces a rotational component in the flow of blood and by keeping the lumen as large as possible over most if not all of its length. Another benefit of keeping the lumen as large as possible and of reducing flow resistance is the resulting increase in the volume of flow in the lumen. Higher blood flow through the cannula(e) can increase the effectiveness thereof in a given treatment.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

What is claimed is:

1. A percutaneous cannula for the exchange of blood within a patient's vasculature, the cannula comprising:
    a main cannula portion comprising a proximal portion, a distal portion, a first lumen, and a second lumen extending through the proximal portion, the first lumen having a first perimeter at a location within the proximal portion and a second perimeter at a location within the distal portion, the second perimeter being greater than the first perimeter; and
    a tip portion extending from the main cannula portion to a distal end of the cannula, the tip portion comprising:
        a discharge opening configured to discharge blood externally to the cannula; and
        a redirecting member configured to direct blood flow being discharged through the discharge opening along the cannula toward the proximal portion of the main cannula portion.

2. The cannula of claim 1, wherein the first lumen is longer than the second lumen.

3. The cannula of claim 1, wherein the tip portion is connected to the first lumen.

4. The cannula of claim 3, wherein the first lumen is longer than the second lumen.

5. The cannula of claim 3, wherein the tip portion further comprises a surface extending across the first lumen, the surface configured to direct blood through the discharge opening.

6. The cannula of claim 5, wherein the surface is curved.

7. The cannula of claim 6, wherein the surface is spherical or parabolic.

8. A system comprising:
    the cannula of claim 1; and
    a pump configured to fluidly communicate with the first lumen and to fluidly communicate with the second lumen.

9. The system of claim 8, wherein the pump is configured to pump blood through the patient at subcardiac rates.

10. A method of treating a patient, comprising:
    providing a percutaneous cannula comprising
        a main cannula portion comprising a proximal portion, a distal portion, a first lumen, and a second lumen extending through the proximal portion, the main cannula portion comprising an inlet for one of the first and second lumens, and at least one of the first and second lumens is configured to reduce the effect of flow resistance therein; and
        a tip portion extending from the main cannula portion to a distal end of the cannula, the tip portion comprising:
            a discharge opening fluidly coupled to the inlet through one of the first and second lumens and located distally of the inlet; and
            a redirecting member configured to direct blood flow being discharged through the discharge opening along the cannula toward the proximal portion of the main cannula portion; and
    inserting the cannula into the vasculature of the patient such that the redirecting member is located in the vasculature.

11. The method of claim 10, wherein the first lumen is longer than the second lumen.

12. The method of claim 10, wherein the tip portion is connected to the first lumen.

13. The method of claim 12, wherein the first lumen is longer than the second lumen.

14. The method of claim 10, further comprising coupling a pump with the cannula such that positive pressure is applied to the first lumen.

15. The method of claim 10, further comprising
    drawing blood into the second lumen;
    directing blood into the first lumen toward the discharge opening.

16. The method of claim 10, wherein the first lumen has a first cross-sectional area at a location within the proximal portion and a second cross-sectional area at a location within the distal portion, the second cross-sectional area being greater than the first cross-sectional area.

17. The method of claim 10, further comprising drawing blood from the vasculature into the inlet and discharging blood through the discharge opening at a location distal of the inlet.

18. A percutaneous cannula for the exchange of blood within a patient's vasculature, the cannula comprising:
    a main cannula portion comprising a proximal portion, a distal portion, a first lumen, and a second lumen extending through the proximal portion, the main cannula portion comprising an inlet for one of the first and second lumens; and
    a tip portion extending from the main cannula portion to a distal end of the cannula, the tip portion comprising:
        a discharge opening fluidly coupled to the inlet through one of the first and second lumens and located distally of the inlet; and
        a redirecting member configured to direct blood flow being discharged through the discharge opening along the cannula toward the proximal portion of the main cannula portion;
    wherein at least one of the first and second lumens is configured to reduce the effect of flow resistance therein.

19. The cannula of claim 18, wherein the effect of flow resistance is reduced by configuring the first lumen with a first cross-sectional area at a location within the proximal portion and a second cross-sectional area at a location within the distal portion, the second cross-sectional area being greater than the first cross-sectional area.

20. The cannula of claim 18, wherein the effect of flow resistance is reduced by configuring the first lumen to induce a rotational component in the flow of blood therein.

21. The cannula of claim 20, further comprising a ridge extending into the lumen.

22. The cannula of claim 21, wherein the ridge is a spiral ridge extending about the lumen.

23. The cannula of claim 18, wherein the redirecting member comprises an expandable member configured to expand under the pressure of the blood flow directed through the discharge opening such that at least a portion of the expandable member is spaced from the discharge opening by a greater amount than prior to such expansion, the expandable member presenting a concave redirecting surface to blood flowing through the discharge opening when expanded.

24. The cannula of claim 23, wherein the expandable member has a proximal end with a perimeter, the expandable member having a contracted configuration in which the perimeter has a first length and an expanded configuration in which the perimeter has a second length, the second length being greater than the first length.

25. The cannula of claim 18, wherein the redirecting member is collapsible to cover the discharge opening during insertion.

26. The cannula of claim 18, wherein the redirecting member is collapsible to partially cover the discharge opening during insertion.

27. The cannula of claim 18, wherein the redirecting member is actuatable to a pre-defined shape.

28. The cannula of claim 18, wherein the tip portion comprises a plurality of discharge openings.

29. The cannula of claim 28, wherein the tip portion further comprises a plurality of redirecting members configured to direct blood flow being discharged through the discharge openings proximally along the cannula.

30. The cannula of claim 29, wherein at least one of the redirecting members comprises an expandable member having a distal end and a proximal end adjacent to a proximal end of a corresponding discharge opening, at least two sides of the expandable member being connected to the tip portion.

31. The cannula of claim 28, wherein the discharge openings are uniformly spaced radially around the tip portion.

* * * * *

UNITED STATES PATENT AND TRADEMARK OFFICE
CERTIFICATE OF CORRECTION

PATENT NO. : 7,445,592 B2
APPLICATION NO. : 10/866535
DATED : November 4, 2008
INVENTOR(S) : Robert Pecor It is certified that error appears in the above-identified patent and that said Letters Patent is hereby corrected as shown below:

Title Page 2, in Column 1, Line 11, Item (56) under U.S. Patent Documents, change "Colney" to --Conley--, therefor.

Title Page 2, in Column 1, Line 33, Item (56) under U.S. Patent Documents, change "Mahukar" to --Mahurkar--, therefor.

Title Page 2, in Column 2, Line 51, Item (56) under U.S. Patent Documents, change "Klien" to --Klein--, therefor.

Title Page 3, in Column 2, Line 50, Item (56) under Other Publications, change "205;" to --2005;--, therefor.

Title Page 3, in Column 2, Line 66, Item (56) under Other Publications, change "Auxillar" to --Auxiliar--, therefor.

Title Page 4, in Column 1, Line 13, Item (56) under Other Publications, change "Venticular" to --Ventricular--, therefor.

Title Page 4, in Column 1, Line 15, Item (56) under Other Publications, change "Auxillary" to --Auxiliary--, therefor.

Title Page 4, in Column 1, Line 18, Item (56) under Other Publications, change "1998," to --1988,--, therefor.

Signed and Sealed this

Twenty-second Day of June, 2010

David J. Kappos
*Director of the United States Patent and Trademark Office*

Title Page 4, in Column 1, Line 18, Item (56) under Other Publications, change "Hagertstown" to --Hagerstown--, therefor.

Title Page 4, in Column 2, Line 9, Item (56) under Other Publications, change "Reltan" to --Reitan--, therefor.

Title Page 4, in Column 2, Line 20, Item (56) under Other Publications, change "Treatement" to --Treatment--, therefor.

In Column 4, Line 31, change "operation;" to --operation.--, therefor.

In Column 11, Line 23, change "decomperisation" to --decompensation--, therefor.

In Column 15, Line 8, change "specification" to --specification.--, therefor.

In Column 16, Line 35, change "FIG. 14-16" to --FIGS. 14-16--, therefor.

In Column 17, Line 17, change "intrasvascular" to --intravascular--, therefor.

In Column 17, Line 42, change "intrasvascular" to --intravascular--, therefor.

In Column 17, Line 48, change "intrasvascular" to --intravascular--, therefor.

In Column 17, Line 50, change "intrasvascular" to --intravascular--, therefor.

In Column 18, Line 23, change "off of" to --of--, therefor.

In Column 18, Line 46, change "aorta" to --aorta.--, therefor.

In Column 26, Line 46, change "mutilumen" to --multilumen--, therefor.

In Column 30, Line 29, change "15 A," to --15A,--, therefor.

In Column 31, Line 28, change "902'" to --902--, therefor.

In Column 36, Line 5, change "some," to --some--, therefor.

In Column 38, Line 62, change "aspects," to --aspects--, therefor.